(12) United States Patent
Laughlin, II et al.

(10) Patent No.: US 11,771,637 B2
(45) Date of Patent: Oct. 3, 2023

(54) SKIN CARE COMPOSITION AND METHOD OF USING THE SAME

(71) Applicant: The Procter & Gamble Company, Cincinnati, OH (US)

(72) Inventors: Leo Timothy Laughlin, II, Mason, OH (US); Michael Joseph Flagler, Anderson Township, OH (US); Bradley Bryan Jarrold, Union Township, OH (US); Lisa Ann Mullins, West Chester, OH (US); Joseph Daniel Sherrill, Loveland, OH (US); Makio Tamura, Cincinnati, OH (US)

(73) Assignee: The Procter & Gamble Company, Cincinnati, OH (US)

(*) Notice: Subject to any disclaimer, the term of this patent is extended or adjusted under 35 U.S.C. 154(b) by 93 days.

(21) Appl. No.: 17/155,327

(22) Filed: Jan. 22, 2021

(65) Prior Publication Data
US 2022/0241175 A1 Aug. 4, 2022

(51) Int. Cl.
*A61K 8/67* (2006.01)
*A61K 8/64* (2006.01)
*A61Q 19/08* (2006.01)

(52) U.S. Cl.
CPC .............. *A61K 8/675* (2013.01); *A61K 8/64* (2013.01); *A61Q 19/08* (2013.01)

(58) Field of Classification Search
CPC .................................................... A61K 8/675
See application file for complete search history.

(56) References Cited

U.S. PATENT DOCUMENTS

| | | |
|---|---|---|
| 3,755,560 A | 8/1973 | Dickert et al. |
| 4,421,769 A | 12/1983 | Dixon et al. |
| 5,011,681 A | 4/1991 | Ciotti et al. |
| 5,872,112 A | 2/1999 | Blank |
| 5,939,082 A | 8/1999 | Oblong et al. |
| 5,972,359 A | 10/1999 | Sine et al. |
| 6,174,533 B1 | 1/2001 | Sanogueira, Jr. et al. |
| 6,492,326 B1 | 12/2002 | Robinson |
| 6,524,598 B2 | 2/2003 | Sunkel et al. |
| 6,696,049 B2 | 2/2004 | Vatter |
| 8,568,751 B1 | 10/2013 | Goldsberry et al. |
| 9,192,558 B2 | 11/2015 | Chen et al. |
| 9,446,265 B2 | 9/2016 | Jansen et al. |
| 9,511,010 B2 | 12/2016 | Van Den Nest et al. |
| 9,597,274 B2 | 3/2017 | Idkowiak-baldys et al. |
| 9,795,552 B2 | 10/2017 | Tanner et al. |
| 9,833,405 B2 | 12/2017 | Xu et al. |
| 10,265,348 B2 | 4/2019 | Soley Astals et al. |
| 10,668,000 B2 | 6/2020 | Peschard et al. |
| 2002/0022040 A1 | 2/2002 | Robinson et al. |
| 2003/0049212 A1 | 3/2003 | Robinson et al. |
| 2004/0175347 A1 | 9/2004 | Bissett |
| 2006/0018860 A1 | 1/2006 | Chen et al. |
| 2006/0275237 A1 | 12/2006 | Bissett |
| 2007/0196344 A1 | 8/2007 | Osborne et al. |
| 2008/0095732 A1 | 4/2008 | Osborne |
| 2008/0181956 A1 | 7/2008 | Ha et al. |
| 2008/0206373 A1 | 8/2008 | Millikin et al. |
| 2009/0111731 A1 | 4/2009 | Imfeld et al. |
| 2010/0092408 A1 | 4/2010 | Breyfogle |
| 2010/0098752 A1 | 4/2010 | Pinsky |
| 2010/0189669 A1 | 7/2010 | Hakozaki |
| 2010/0227011 A1* | 9/2010 | Kuhlman ............. A61K 36/906 424/756 |
| 2010/0239510 A1 | 9/2010 | Ha et al. |
| 2010/0272667 A1 | 10/2010 | Kyte, III et al. |
| 2011/0097286 A1 | 4/2011 | Swanson |
| 2011/0262025 A1 | 10/2011 | Jarrold et al. |
| 2011/0262570 A1 | 10/2011 | Finlay et al. |
| 2011/0300199 A1 | 12/2011 | Garcia et al. |
| 2011/0305737 A1 | 12/2011 | Alexiades-armenakas |
| 2012/0028916 A1 | 2/2012 | Fournial et al. |
| 2012/0076842 A1 | 3/2012 | Fournial et al. |
| 2012/0121675 A1 | 5/2012 | Garcia et al. |
| 2012/0128683 A1 | 5/2012 | Shantha |
| 2012/0148515 A1 | 6/2012 | Hakozaki et al. |
| 2012/0156146 A1 | 6/2012 | Hakozaki et al. |
| 2012/0197016 A1 | 8/2012 | Laughlin, II |
| 2012/0301410 A1 | 11/2012 | Ali |

(Continued)

FOREIGN PATENT DOCUMENTS

| | | |
|---|---|---|
| CN | 103767971 A | 5/2014 |
| CN | 104688622 A | 6/2015 |

(Continued)

OTHER PUBLICATIONS

Neogenlab, Sur.medic+ Perfection 100 All in One Facial Eye Cream, publication date: Nov. 20, 2020, date acquired from the Wayback Machine (Year: 2020).*
Soko Glam, Sur.medic+ Perfection 100 All in One Facial Eye Cream, downloaded in Jan. 2023 (Year: 2023).*
Silke Karin Schagen, Topical Peptide Treatments with Effective Anti-Aging Results, Cosmetics 2017, 4, 16 (Year: 2017).*
15964 PCT Search Report and Written Opinion for PCT/US2022/070277dated May 16, 2022, 11 pages.
Database GNPD [Online] 1 MINTEL; Aug. 13, 2021 (Aug. 13, 2021), anonymous: "Serum", XP055915466, Database accession No. 8935135, the whole document, 5 pages.

(Continued)

*Primary Examiner* — Mark V Stevens
*Assistant Examiner* — Alparslan Asan
(74) *Attorney, Agent, or Firm* — Alexandra S. Anoff

(57) ABSTRACT

A skin care composition that contains a combination of a vitamin $B_3$ compound, palmitoyl pentapeptide-4, acetyl tetrapeptide-11, and a dermatologically acceptable carrier. The combination of vitamin $B_3$ compound, palmitoyl pentapeptide-4, and acetyl tetrapeptide-11 increases activation of a cell's Antioxidant Response Element (ARE), (e.g., synergistically) to improve a visible sign of skin aging.

14 Claims, No Drawings
Specification includes a Sequence Listing.

(56) References Cited

U.S. PATENT DOCUMENTS

| | | |
|---|---|---|
| 2012/0315235 A1 | 12/2012 | Weisenfluh et al. |
| 2013/0017239 A1 | 1/2013 | Viladot et al. |
| 2013/0022557 A1 | 1/2013 | Swanson et al. |
| 2013/0064876 A1 | 3/2013 | Viladot et al. |
| 2013/0101662 A1 | 4/2013 | Carreno et al. |
| 2013/0216596 A1 | 8/2013 | Viladot et al. |
| 2013/0302261 A1 | 11/2013 | Courtois et al. |
| 2014/0370098 A1 | 12/2014 | Terrisse et al. |
| 2015/0017269 A1 | 1/2015 | Fournial et al. |
| 2015/0071974 A1 | 3/2015 | Ferrer Montiel et al. |
| 2015/0098989 A1 | 4/2015 | Ferrer Montiel et al. |
| 2015/0140046 A1 | 5/2015 | Ferrer Montiel et al. |
| 2015/0183823 A1 | 7/2015 | Garca et al. |
| 2015/0196464 A1 | 7/2015 | Jansen et al. |
| 2016/0074291 A1 | 3/2016 | Tamura et al. |
| 2016/0074301 A1 | 3/2016 | Tamura et al. |
| 2016/0074309 A1 | 3/2016 | Kessler-becker et al. |
| 2016/0120794 A1 | 5/2016 | Liu et al. |
| 2016/0317419 A1 | 11/2016 | Hakazaki et al. |
| 2017/0319462 A1 | 11/2017 | Marchant et al. |
| 2018/0264245 A1 | 9/2018 | Edwards et al. |
| 2018/0311358 A1 | 11/2018 | Marchant et al. |
| 2018/0332951 A1 | 11/2018 | Jang et al. |
| 2018/0369579 A1 | 12/2018 | Jang et al. |
| 2019/0099362 A1 | 4/2019 | Ringenbach et al. |
| 2019/0153030 A1 | 5/2019 | Peschard et al. |
| 2020/0297654 A1 | 9/2020 | Marchant et al. |
| 2021/0069088 A1 | 3/2021 | Jiang et al. |

FOREIGN PATENT DOCUMENTS

| | | |
|---|---|---|
| CN | 105342927 A | 2/2016 |
| CN | 105560078 A | 5/2016 |
| CN | 105640845 A | 6/2016 |
| CN | 105748319 A | 7/2016 |
| CN | 107184459 A | 9/2017 |
| CN | 107375041 A | 11/2017 |
| CN | 107802561 A | 3/2018 |
| CN | 108309919 A | 7/2018 |
| CN | 108670896 A | 10/2018 |
| CN | 109330964 A | 2/2019 |
| CN | 109394612 A | 3/2019 |
| CN | 109453095 A | 3/2019 |
| CN | 109464307 A | 3/2019 |
| CN | 109846804 A | 6/2019 |
| CN | 109953927 A | 7/2019 |
| CN | 109984952 A | 7/2019 |
| CN | 110074990 A | 8/2019 |
| CN | 110123729 A | 8/2019 |
| CN | 110179725 A | 8/2019 |
| CN | 110269831 A | 9/2019 |
| CN | 110302077 A | 10/2019 |
| CN | 110302089 A | 10/2019 |
| CN | 110384629 A | 10/2019 |
| CN | 110420160 A | 11/2019 |
| CN | 110522711 A | 12/2019 |
| CN | 110585055 A | 12/2019 |
| CN | 110585056 A | 12/2019 |
| EP | 1790330 A2 | 5/2007 |
| JP | 2003040724 A | 2/2003 |
| JP | 2004238354 A | 8/2004 |
| JP | 2004238355 A | 8/2004 |
| JP | 2013053147 A | 3/2013 |
| JP | 2014114289 A | 6/2014 |
| KR | 20090062226 A | 6/2009 |
| KR | 101769416 B1 | 8/2017 |
| KR | 20190116693 A | 10/2019 |
| WO | 0062743 A2 | 10/2000 |
| WO | 2012164488 A2 | 12/2012 |
| WO | 2018236069 A1 | 12/2018 |

OTHER PUBLICATIONS

Database GNPD [Online] 1 MINTEL; Jun. 21, 2021 (Jun. 21, 2021), anonymous: "Eye Cream", XP055915464, Database accession No. 8749319, the whole document, 5 pages.

Database GNPD [Online] MINTEL; Oct. 23, 2020 (Oct. 23, 2020), anonymous: "Cream", XP055917310, Database accession No. 8209161 the whole document, 5 pages.

All Office Actions; U.S. Appl. No. 17/155,357, filed Jan. 22, 2021.

Generation of a Stable Antioxidant Response Element-Driven Reporter Gene Cell Line and Its Use to Show Redox-Dependent Activation of Nrf2 by Cancer Chemotherapeutic Agents. Cancer Res 2006; 66(22): Nov. 15, 2006; pp. 10983-10994.

He M. et al, "The role of sterol-C4-methyl oxidase in epidermal biology." Biochim Biophys Acta. Mar. 2014; 1841(3), pp. 331-335.

Lopez-Leon, S et al. "Sports genetics: the PPARA gene and athletes' high ability in endurance sports. A systematic review and meta-analysis." Biology of sport vol. 33.1 (2016): pp. 3-6.

Silke Karin Schagen, "Topical Peptide Treatments with Effective Anti-Aging Results", Cosmetics, 2017—mdpi.com , retrieved from htttps://doi.org/10.3390/cosmetics4020016, May 22, 2017, pp. 1-14.

U.S. Appl. No. 17/155,357, filed Jan. 22, 2021, to Leo Timothy Laughlin et. al.

All Office Actions; U.S. Appl. No. 18/149,728, filed Jan. 4, 2023.

U.S. Appl. No. 18/149,728, filed Jan. 4, 2023, to Leo Timothy Laughlin et al.

Osborne et al."J Am Acad Dermatol in vitro skin structure benefits with a new antiaging peptide, Pal-KT", Feb. 2008, pp. 1.

\* cited by examiner

SKIN CARE COMPOSITION AND METHOD OF USING THE SAME

FIELD

The present disclosure is directed generally to improving skin health with a synergistic combination of skin care actives. More specifically, the present disclosure is directed to a combination of vitamin $B_3$ and two or more peptides that synergistically stimulates cellular anti-oxidancy and repair processes.

BACKGROUND

Skin is the first line of defense against environmental insults that would otherwise damage sensitive underlying tissue and organs, and skin plays a key role in a person's physical appearance. The tell-tale signs of aging, such as wrinkles and age spots on the skin, are an undesirable reminder of the disappearance of youth. As a result, treating the signs of aging in skin has become a booming business in youth-conscious societies.

Skin is made up of a variety of different cells that function together in a dynamic, complex relationship to maintain the health of the skin. However, as skin cells age or become damaged, they generally lose their ability to function at the level needed to maintain young, healthy looking skin. Skin cells can be damaged by a variety of endogenous and exogenous stressors (e.g., ultraviolet radiation, pollution, smoking). In some instances, these stressors cause the production of reactive oxygen species (ROS), which interfere with normal cellular processes. In response, human cells have evolved defenses to combat ROS, but the cell's defenses can be overwhelmed by spikes of stressor-induced ROS, leading to not just acute but also chronic alterations in cellular homeostasis. As ROS accumulate over time, they cause oxidative stress at the cellular level, which can ultimately manifest as visible signs of aging (e.g., fine lines, wrinkles, hyperpigmented spots, thinning skin).

The antioxidant defense system of most cells is typically controlled by a master switch referred to as the antioxidant response element (ARE). The ARE is a cis-acting enhancer sequence located in the regulatory regions of antioxidant and detoxifying genes. The ARE is activated by redox-cycling phenols and electrophiles. Some studies have shown that a protein called nuclear factor erythroid 2-related factor 2 (Nrf2) may be the principal transcription factor necessary for ARE activation, even though many other transcription factors also bind to the ARE sequence.

When the ARE is activated in response to damage from ROS, the corresponding genes signal the cell to begin producing reduction/oxidation regulators and/or ROS quenching proteins and enzymes. In addition to modulating the production of redox regulators and ROS quenching compounds, the ARE can also signal the cell to begin repair processes. Thus, it would be desirable to boost activation of the ARE in aging skin cells to combat the signs of skin aging caused by oxidative stress.

A number of compounds have been discovered that boost activation of the ARE. For example, US20160317419 provides data showing that a combination of niacinamide and nicotinamide riboside boosts ARE activation. However, there is still a need to identify compounds and methods that improve cellular anti-oxidancy by boosting ARE activation. There is also a need to identify compounds and methods that beneficially modulate genes involved in cellular anti-oxidancy and repair.

SUMMARY

The present disclosure relates to a skin care composition, comprising a combination of a vitamin $B_3$ compound, palmitoyl pentapeptide-4 (pal-KTTKS) [SEQ ID NO: 1], acetyl tetrapeptide-11 (ac-PPYL) [SEQ ID NO: 2], and a dermatologically acceptable carrier. The combination of vitamin $B_3$ compound, pal-KTTKS [SEQ ID NO: 1], and ac-PPYL [SEQ ID NO: 2]. This combination of compounds has been found to activate a cell's Antioxidant Response Element (ARE) and/or beneficially modulate genes involved in cellular anti-oxidancy and repair, in some instances synergistically. The present disclosure also relates to methods of using the foregoing compositions.

DETAILED DESCRIPTION

Improving cellular anti-oxidancy and repair is important for improving the health and/or appearance of skin. Thus, there is a long felt need to identify new ingredients for use in topical skin care compositions that provide these benefits. In particular, there is a need to identify compounds that boost ARE activation in skin cells, which tend to be more at-risk from oxidative stress than some other types of cells due to their high exposure to ultraviolet radiation and other exogenous stressors. It has now been surprisingly discovered that combining a vitamin $B_3$ compound, palmitoyl pentapeptide-4 [SEQ ID NO: 1], and acetyl tetrapeptide-11 [SEQ ID NO: 2] can stimulate anti-oxidancy and cell repair processes. In particular, this combination of ingredients has been found to synergistically boost ARE activation and/or modulate certain genes believed to be involved in cellular anti-oxidancy and repair.

Reference herein to "embodiment(s)" or the like means that a particular material, feature, structure and/or characteristic described in connection with the embodiment is included in at least one embodiment, optionally a number of embodiments, but it does not mean that all embodiments incorporate the material, feature, structure, and/or characteristic described. Furthermore, materials, features, structures and/or characteristics may be combined in any suitable manner across different embodiments, and materials, features, structures and/or characteristics may be omitted or substituted from what is described. Thus, embodiments and aspects described herein may comprise or be combinable with elements or components of other embodiments and/or aspects despite not being expressly exemplified in combination, unless otherwise stated or an incompatibility is stated.

In all embodiments, all ingredient percentages are based on the weight of the cosmetic composition, unless specifically stated otherwise. All ratios are weight ratios, unless specifically stated otherwise. The number of significant digits conveys neither a limitation on the indicated amounts nor on the accuracy of the measurements. All numerical amounts are understood to be modified by the word "about" unless otherwise specifically indicated. Unless otherwise indicated, all measurements are understood to be made at approximately 25° C. and at ambient conditions, where "ambient conditions" means conditions under about 1 atmosphere of pressure and at about 50% relative humidity. All numeric ranges are inclusive and combinable to form narrower ranges not explicitly disclosed. For example, delineated upper and lower range limits are interchangeable to create further ranges.

The compositions of the present invention can comprise, consist essentially of, or consist of, the essential components as well as optional ingredients described herein. As used herein, "consisting essentially of" means that the composition or component may only include additional ingredients that do not materially alter the basic and novel characteristics of the claimed composition or method. As used in the description and the appended claims, the singular forms "a", "an", and "the" are intended to include the plural forms as well, unless the context clearly indicates otherwise.

SEQUENCE LISTING

A sequence listing that sets forth the amino acid sequences for SEQ ID NOS: 1 and 2 and the nucleotide sequences for SEQ ID NOS: 3 to 7, which are primary sequences and include conservatively modified variants thereof, is being filed concurrently with the present application as an ASCII text file titled "15964_seq_list_ST25". This ASCII text file was created on Jan. 19, 2021 and is 201 KB in size. An ASCII text file titled "15964-Sequence_Listing_2023_07_25" was created on Jul. 25, 2023 and is 202 KB in size. In accordance with MPEP § 605.08 and 37 CFR § 1.52(e), the subject matter in the ASCII text files are incorporated herein by reference.

Definitions

"About" modifies a particular value by referring to a range equal to plus or minus twenty percent (+/−20%) or less (e.g., less than 15%, 10%, or even less than 5%) of the stated value.

"Apply" or "application," as used in reference to a composition or material herein, means to place or spread the composition onto a human skin surface such as the epidermis.

"Cosmetic composition" means a composition comprising a cosmetic agent and intended for non-therapeutic (i.e., medical) use. Examples of cosmetic compositions include color cosmetics (e.g., foundations, lipsticks, concealers, and mascaras), skin care compositions (e.g., moisturizers and sunscreens), personal care compositions (e.g., rinse-off and leave on body washes and soaps), hair care compositions (e.g., shampoos and conditioners).

"Derivative" means an amide, ether, ester, amino, carboxyl, acetyl, or alcohol derivative of a given compound.

"Effective amount" means an amount of a compound or composition sufficient to significantly induce a positive benefit to keratinous tissue over the course of a treatment period. The positive benefit may be a health, appearance, and/or feel benefit, including, independently or in combination, the benefits disclosed herein.

"Modulate" and variations thereof mean upregulating or downregulating gene expression.

"Skin care" means regulating and/or improving a skin condition (e.g., skin health, appearance, or texture/feel). Some nonlimiting examples of improving a skin condition include improving skin appearance and/or feel by providing a smoother, more even appearance and/or feel; increasing the thickness of one or more layers of the skin; improving the elasticity or resiliency of the skin; improving the firmness of the skin; and reducing the oily, shiny, and/or dull appearance of skin, improving the hydration status or moisturization of the skin, improving the appearance of fine lines and/or wrinkles, improving skin exfoliation or desquamation, plumping the skin, improving skin barrier properties, improve skin tone, reducing the appearance of redness or skin blotches, and/or improving the brightness, radiancy, or translucency of skin.

"Skin care active" means a compound or combination of compounds that, when applied to skin, provide an acute and/or chronic benefit to skin or a type of cell commonly found therein. Skin care actives may regulate and/or improve skin or its associated cells (e.g., improve skin elasticity, hydration, skin barrier function, and/or cell metabolism).

"Skin care composition" means a composition that includes a skin care active and regulates and/or improves skin condition.

"Skin cell" refers to the types of cells commonly found in human skin. Non-limiting examples of skin cells are keratinocytes, fibroblasts, melanocytes, Langerhans cells, and Merkel cells.

"Synergy" and variations thereof mean that the cellular anti-oxidancy and repair effect provided by a combination of niacinamide, palmitoyl pentapeptide-4 [SEQ ID NO: 1], and acetyl tetrapeptide-11 [SEQ ID NO: 2] is more than the predicted additive effect of these ingredients alone. For example, synergy is demonstrated when the combination of niacinamide, palmitoyl pentapeptide-4 [SEQ ID NO: 1], and acetyl tetrapeptide-11 [SEQ ID NO: 2] increases ARE activation by a more than the calculated additive effects of these three ingredients individually. ARE activation level can be quantitated using the ARE Assay described in more detail below.

"Treatment period," as used herein, means the length of time and/or frequency that a material or composition is applied to a target skin surface.

"Upregulation" and variations thereof mean increasing gene expression. Conversely, "downregulation" and variations thereof mean decreasing gene expression. Gene expression can be quantitated using conventional methods (e.g., microarray analysis, rt-PCR, Western blot).

Skin Care Composition

The novel skin care compositions herein are intended for topical application to human skin to provide a cellular anti-oxidancy and/or repair benefit. The present skin care compositions contain a safe and effective amount of a vitamin B3 compound, palmitoyl pentapeptide-4 (pal-KTTKS) [SEQ ID NO: 1], and acetyl tetrapeptide-11 (ac-PPYL) [SEQ ID NO: 2]. An effective amount of these three ingredients in combination can synergistically boost activation of the antioxidant response element, which is important for combating oxidative stress and reducing the visible signs of skin aging.

The combination of vitamin B3 compound, pal-KTTKS [SEQ ID NO: 1], and ac-PPYL [SEQ ID NO: 2] may also synergistically modulate one or more genes selected from Nuclear Factor Erythroid2-Related Factor 2 (NFE2L2) [SEQ ID NO: 3] (the primary sequence) and conservatively modified variants thereof, Schlafen Family Member 5 (SLFN5) [SEQ ID NO: 4] (the primary sequence) and conservatively modified variants thereof, Glycerophosphodiester Phosphodiesterase 1 (GDE1) [SEQ ID NO: 5] (the primary sequence) and conservatively modified variants thereof, Multiple Inositol-Polyphosphate Phosphatase 1 (MINPP1) [SEQ ID NO: 6] (the primary sequence) and conservatively modified variants thereof, and 3-Hydroxy-3-Methylglutaryl-CoA Lyase (HMGCL) [SEQ ID NO: 7] (the primary sequence) and conservatively modified variants thereof. It is believed, without being limited by theory, that these genes play important roles in cellular anti-oxidancy and/or repair, and it has been shown that these genes are downregulated as a result of chronological aging and/or photoaging in the epidermis and/or dermis. For example, NRF2 is believed to play an important role in activating the ARE (*Annu Rev Pharmacol Toxicol.* 2013; 53: 401-426). In another example, it is believed that SLFN5 plays a role in controlling extracellular matrix (ECM) remodeling enzymes. Conditions of oxidative stress stimulate ECM degradation by up-regulating metalloproteinases (MMPs). Up-regulation of SLFN5 turns down the expression of these MMPs thus enhancing ECM integrity.

With respect to boosting ARE activation and/or modulating the expression of one or more of the genes described above, the combination of vitamin $B_3$ compound, pal-KTTKS [SEQ ID NO: 1], and ac-PPYL [SEQ ID NO: 2] may exhibit a synergy of factor of 1.2 or more (e.g., greater than 1.3, 1.4, 1.5, 1.6, 1.7, 1.8, 1.9, or even 2.0) relative to the sum of the responses from niacinamide, pal-KTTKS, and ac-PPYL treatments individually, such as a vehicle control or predetermined threshold value. In some instances, the composition may contain a weight ratio of vitamin B3 compound to pal-KTTKS [SEQ ID NO: 1] to ac-PPYL [SEQ ID NO: 2] of between 500:1:2 and 1:1:0.5 (e.g., between 50:1:2 and 1:1:1). A method for determining synergy factor is described in more detail below.

The skin care compositions herein may be cosmetic compositions, pharmaceutical compositions, or cosmeceutical compositions, and may be provided in various product forms, including, but not limited to, solutions, suspensions, lotions, creams, gels, toners, sticks, sprays, aerosols, ointments, cleansing liquid washes and solid bars, pastes, foams, mousses, shaving creams, wipes, strips, patches, electrically-powered patches, hydrogels, film-forming products, facial and skin masks (with and without insoluble sheet), make-up such as foundations, eye liners, and eye shadows, and the like. In some instances, the composition form may follow from the particular dermatologically acceptable carrier chosen. For example, the composition (and carrier) may be provided in the form of an emulsion (e.g., water-in-oil, oil-in-water, or water-in-oil-in water) or an aqueous dispersion.

The combination of vitamin B3 compound, pal-KTTKS [SEQ ID NO: 1], and ac-PPYL [SEQ ID NO: 2] may also synergistically modulate one or more genes selected from Nuclear Factor Erythroid2-Related Factor 2 (NRF2) [SEQ ID NO: 3] (the primary sequence) and conservatively modified variants thereof, Schlafen Family Member 5 (SLFN5) [SEQ ID NO: 4] (the primary sequence) and conservatively modified variants thereof, Glycerophosphodiester Phosphodiesterase 1 (GDE1) [SEQ ID NO: 5] (the primary sequence) and conservatively modified variants thereof, Multiple Inositol-Polyphosphate Phosphatase 1 (MINPP1) [SEQ ID NO: 6] (the primary sequence) and conservatively modified variants thereof, and 3-Hydroxy-3-Methylglutaryl-CoA Lyase (HMGCL) [SEQ ID NO: 7] (the primary sequence) and conservatively modified variants thereof. It is believed, without being limited by theory, that these genes play important roles in cellular anti-oxidancy and/or repair, and it has been shown that these genes are downregulated as a result of chronological aging and/or photoaging in the epidermis and/or dermis. For example, NRF2 is believed to play an important role in activating the ARE (*Annu Rev Pharmacol Toxicol.* 2013; 53: 401-426). In another example, it is believed that SLFN5 plays a role in controlling extracellular matrix (ECM) remodeling enzymes. Conditions of oxidative stress stimulate ECM degradation by up-regulating metalloproteinases (MMPs). Up-regulation of SLFN5 turns down the expression of these MMPs thus enhancing ECM integrity.

Vitamin $B_3$ Compound

The compositions herein include a safe and effective amount of a vitamin $B_3$ compound. In some instances, the present compositions may contain 0.01% to 10%, by weight, of the vitamin $B_3$ compound, based on the weight or volume of the composition (e.g., 0.1% to 10%, 0.5% to 5%, or even 1% to 3%).

As used herein, "vitamin $B_3$ compound" means a compound having the formula:

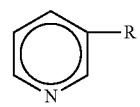

Where: R is $CONH_2$ (i.e., niacinamide), COOH (i.e., nicotinic acid) or $CH_2OH$ (i.e., nicotinyl alcohol); derivatives thereof; and salts of any of the foregoing.

Exemplary derivatives of vitamin $B_3$ compounds include nicotinic acid esters, including non-vasodilating esters of nicotinic acid (e.g., tocopheryl nicotinate, myristyl nicotinate) nicotinamide riboside, nicotinyl amino acids, nicotinyl alcohol esters of carboxylic acids, nicotinic acid N-oxide, and niacinamide N-oxide.

Pentapeptide

The compositions herein include a safe and effective amount of the palmitoylated pentapeptide, pal-KTTKS [SEQ ID NO: 1] (INCI: Palmitoyl Pentapeptide-4). In some instances, pal-KTTKS may be present in the present compositions at 0.0001% to 3% (e.g., 0.001% to 2%, 0.01% to 1% or 0.1% to 0.5%). Pal-KTTKS is available as PROMATRIXYL from Sederma (France).

Tetrapeptide

The compositions herein include a safe and effective amount of the acetylated tetrapeptide, ac-PPYL [SEQ ID NO: 2] (INCI: Acetyl Tetrapeptide-11). In some instances, ac-PPYL may be present in the present composition at 0.0001% to 3% (e.g., 0.001% to 2%, 0.01% to 1% or 0.1% to 0.5%). Ac-PPYL is available as SYNIORAGE from BASF Care Creations (New Jersey).

Dermatologically Acceptable Carrier

The compositions herein include a dermatologically acceptable carrier (which may be referred to as a "carrier"). The phrase "dermatologically acceptable carrier" means that the carrier is suitable for topical application to the keratinous tissue, has good aesthetic properties, is compatible with the actives in the composition, and will not cause any unreasonable safety or toxicity concerns. In one embodiment, the carrier is present at a level of from about 50% to about 99%, about 60% to about 98%, about 70% to about 98%, or, alternatively, from about 80% to about 95%, by weight of the composition.

The carrier can be in a wide variety of forms. In some instances, the solubility or dispersibility of the components (e.g., extracts, sunscreen active, additional components) may dictate the form and character of the carrier. Non-limiting examples include simple solutions (e.g., aqueous or anhydrous), dispersions, emulsions, and solid forms (e.g., gels, sticks, flowable solids, or amorphous materials). In some instances, the dermatologically acceptable carrier is in the form of an emulsion that has a continuous aqueous phase (e.g., an oil-in-water or water-in-oil-in-water emulsion) or a continuous oil phase (e.g., water-in-oil or oil-in-water-in-oil emulsion). The oil phase of the emulsion may include silicone oils, non-silicone oils such as hydrocarbon oils, esters, ethers, and mixtures thereof. The aqueous phase may include water and water-soluble ingredients (e.g., water-soluble moisturizing agents, conditioning agents, anti-microbials, humectants and/or other skin care actives). In some instances, the aqueous phase may include components other than water, including but not limited to water-soluble moisturizing agents, conditioning agents, anti-microbials, humectants and/or other water-soluble skin care actives. In some instances, the non-water component of the composition comprises a humectant such as glycerin and/or other polyol(s).

In some instances, the compositions herein are in the form of an oil-in-water ("O/W") emulsion that provides a sensorial feel that is light and non-greasy. Suitable O/W emulsions herein may include a continuous aqueous phase of more than 50% by weight of the composition, and the remainder being the dispersed oil phase. The aqueous phase may include 1% to 99% water, based on the weight of the aqueous phase, along with any water soluble and/or water miscible ingredients. In these instances, the dispersed oil phase will typically be present at less than 30% by weight of composition (e.g., 1% to 20%, 2% to 15%, 3% to 12%, 4% to 10%, or even 5% to 8%) to help avoid some of the undesirable feel effects of oily compositions. The oil phase may include one or more volatile and/or non-volatile oils (e.g., botanical oils, silicone oils, and/or hydrocarbon oils). Some nonlimiting examples of oils that may be suitable for use in the present compositions are disclosed in U.S. Pat. No. 9,446,265 and U.S. Publication No. 2015/0196464.

The carrier may contain one or more dermatologically acceptable diluents. As used herein, "diluent" refers to materials in which the skin care actives herein can be dispersed, dissolved, or otherwise incorporated. Some non-limiting examples of hydrophilic diluents include water, organic hydrophilic diluents such as lower monovalent alcohols (e.g., $C_1$-$C_4$) and low molecular weight glycols and polyols, including propylene glycol, polyethylene glycol (e.g., molecular weight of 200 to 600 g/mole), polypropylene glycol (e.g., molecular weight of 425 to 2025 g/mole), glycerol, butylene glycol, 1,2,4-butanetriol, sorbitol esters, 1,2,6-hexanetriol, ethanol, isopropanol, sorbitol esters, butanediol, ether propanol, ethoxylated ethers, propoxylated ethers and combinations thereof.

Conditioning Agents

The compositions herein may include 0.1% to 50% by weight of a conditioning agent (e.g., 0.5% to 30%, 1% to 20%, or even 2% to 15%). Adding a conditioning agent can help provide the composition with desirable feel properties (e.g., a silky, lubricious feel upon application). Some non-limiting examples of conditioning agents include, hydrocarbon oils and waxes, silicones, fatty acid derivatives, cholesterol, cholesterol derivatives, diglycerides, triglycerides, vegetable oils, vegetable oil derivatives, acetoglyceride esters, alkyl esters, alkenyl esters, lanolin, wax esters, beeswax derivatives, sterols and phospholipids, salts, isomers and derivatives thereof, and combinations thereof. Particularly suitable examples of conditioning agents include volatile or non-volatile silicone fluids such as dimethicone copolyol, dimethylpolysiloxane, diethylpolysiloxane, mixed C1-30 alkyl polysiloxanes, phenyl dimethicone, dimethiconol, dimethicone, dimethiconol, silicone crosspolymers, and combinations thereof. Dimethicone may be especially suitable, since some consumers associate the feel properties provided by certain dimethicone fluids with good moisturization. Other examples of silicone fluids that may be suitable for use as conditioning agents are described in U.S. Pat. No. 5,011,681.

Rheology Modifiers

The compositions herein may include 0.1% to 5% of a rheology modifier (e.g., thickening agent) to provide the composition with suitable rheological and skin feels properties. Some non-limiting examples of thickening agents include crosslinked polyacrylate polymers, polyacrylamide polymers, polysaccharides, gums and mixtures thereof. In a particularly suitable example, the composition may include a superabsorbent polymer thickening agent such as sodium polyacrylate, starch grafted sodium polyacrylate, or a combination of these. Some non-limiting examples of superabsorbent polymer thickeners are described in, for example, U.S. Pat. No. 9,795,552.

Some consumers find compositions that use silicone fluids as conditioning agents to be undesirably greasy or heavy feeling. Thus, it may be desirable to provide a composition that is free of or substantially free of silicone fluid. It may also be desirable to tailor a superabsorbent polymer thickener to provide the composition with a light, airy feel, for example, by adjusting the amount of water in the composition, the water:oil ratio (e.g., 12:1 to 1:1), and/or the ratio of water to thickener or oil to thickener.

Emulsifiers

When the dermatologically acceptable carrier is in the form of an emulsion, it may be desirable to include an emulsifier to provide a stable composition (e.g., does not phase separate). When included, the emulsifier may be present at an amount of 0.1% to 10% (e.g., 1% to 5%, or 2%-4%). Emulsifiers may be nonionic, anionic or cationic. Some non-limiting examples of emulsifiers that may be suitable for use herein are disclosed in U.S. Pat. Nos. 3,755,560; 4,421,769: and McCutcheon's Detergents and Emulsifiers, North American Edition, pages 317-324 (1986).

Other Optional Ingredients

The present composition may optionally include one or more additional ingredients commonly used in cosmetic compositions (e.g., colorants, skin care actives, anti-inflammatory agents, sunscreen agents, emulsifiers, buffers, rheology modifiers, combinations of these and the like), provided that the additional ingredients do not undesirably alter the skin health or appearance benefits provided by the present compositions. The additional ingredients, when incorporated into the composition, should be suitable for use in contact with human skin tissue without undue toxicity, incompatibility, instability, allergic response, and the like. Some nonlimiting examples of additional actives include vitamins, minerals, peptides and peptide derivatives, sugar amines, sunscreens, oil control agents, particulates, flavonoid compounds, hair growth regulators, anti-oxidants and/or anti-oxidant precursors, preservatives, protease inhibitors, tyrosinase inhibitors, anti-inflammatory agents, moisturizing agents, exfoliating agents, skin lightening agents, sunless tanning agents, lubricants, anti-acne actives, anti-cellulite actives, chelating agents, anti-wrinkle actives, anti-atrophy actives, phytosterols and/or plant hormones, N-acyl amino acid compounds, antimicrobials, and antifungals. Other non-limiting examples of additional ingredients and/or skin care actives that may be suitable for use herein are described in U.S. Publication Nos. 2002/0022040; 2003/0049212; 2004/0175347; 2006/0275237; 2007/0196344; 2008/0181956; 2008/0206373; 2010/00092408; 2008/0206373; 2010/0239510; 2010/0189669; 2010/0272667; 2011/0262025; 2011/0097286; US2012/0197016; 2012/0128683; 2012/0148515; 2012/0156146; and 2013/

0022557; and U.S. Pat. Nos. 5,939,082; 5,872,112; 6,492,326; 6,696,049; 6,524,598; 5,972,359; and 6,174,533.

When including optional ingredients in the compositions herein, it may be desirable to select ingredients that do not form complexes or otherwise undesirably interact with other ingredients in the composition, especially pH sensitive ingredients like niacinamide, salicylates and peptides. When present, the optional ingredients may be included at amounts of from 0.0001% to 50%; from 0.001% to 20%; or even from 0.01% to 10% (e.g., 50%, 40%, 30%, 20%, 10%, 5%, 4%, 3%, 2%, 1%, 0.5% or 0.1%), by weight of the composition.

Method of Use

The present method includes identifying a target portion of skin where treatment is desired and applying a composition comprising an effective amount of vitamin $B_3$ compound, pal-KTTKS [SEQ ID NO: 1], and ac-PPYL [SEQ ID NO: 2], and optionally one or more additional skin care actives, to the target portion of skin. The target portion of skin may be on a facial skin surface such as the forehead, perioral, chin, periorbital, nose, and/or cheek) or another part of the body (e.g., hands, arms, legs, back, chest). The person or target portion of skin in need of treatment may be one that exhibits a telltale sign of aging skin (e.g., fine lines, wrinkles, hyperpigmented spots). In some instances, a target portion of skin may not exhibit a sign of skin aging, but a user may still wish to treat the portion of skin if it is one that commonly exposed to higher levels of exogenous stressors (e.g., sun exposed skin such as facial skin and arm skin). In this way, the present methods and compositions may be used prophylactically to help delay skin aging.

The composition may be applied to a target portion of skin and, if desired, to the surrounding skin at least once a day, twice a day, or on a more frequent daily basis, during a treatment period. When applied twice daily, the first and second applications are separated by at least 1 to 12 hours. Typically, the composition is applied in the morning and/or in the evening before bed. The treatment period herein is ideally of sufficient time for the vitamin $B_3$ compound, pal-KTTKS [SEQ ID NO: 1], and ac-PPYL [SEQ ID NO: 2] to improve the appearance of the skin. The treatment period may last for at least 1 week (e.g., about 2 weeks, 4 weeks, 8 weeks, or even 12 weeks). In some instances, the treatment period will extend over multiple months (i.e., 3-12 months). In some instances, the composition may be applied most days of the week (e.g., at least 4, 5 or 6 days a week), at least once a day or even twice a day during a treatment period of at least 2 weeks, 4 weeks, 8 weeks, or 12 weeks.

The step of applying the composition may be accomplished by localized application. In reference to application of the composition, the terms "localized", "local", or "locally" mean that the composition is delivered to the targeted area (e.g., a hyperpigmented spot or portion thereof) while minimizing delivery to skin surfaces where treatment is not desired. The composition may be applied and lightly massaged into an area of skin. The form of the composition or the dermatologically acceptable carrier should be selected to facilitate localized application. While certain embodiments herein contemplate applying a composition locally to an area, it will be appreciated that compositions herein can be applied more generally or broadly to one or more skin surfaces. In certain embodiments, the compositions herein may be used as part of a multi-step beauty regimen, wherein the present composition may be applied before and/or after one or more other compositions.

ARE Assay

This method provides a way to quantitate ARE activation using the ARE-32 reporter cell line available from CXR Biosciences. The ARE-32 cell line is a stable MCF7 cell line containing pGL8x-ARE (8 copies of the rat GST ARE linked to the luciferase gene) and pCDNA3.1, which contains the neomycin selectable marker. A detailed description of the ARE-32 cell line and its development and use can be found in "Generation of a Stable Antioxidant Response Element-Driven Reporter Gene Cell Line and Its Use to Show Redox-Dependent Activation of Nrf2 by Cancer Chemotherapeutic Agents." Cancer Res 2006; 66(22): 10983-94. A general schematic for how an ARE reporter assay operates to identify agents that promote transcription off the ARE is described in U.S. Publication No. 2011/0262570.

Summary of the Method:

The ARE Assay uses expanded and cryopreserved passaged stocks. The cells are expanded over 4-5 days in culture flasks and passaged every 3-4 days, when cells are approximately 80% confluent. When cells are >70% confluent or ready to seed into 96 well plates, the cells are trypsinized, seeded and grown in 96-well plates. After growing for 1 day in 96-well plates, the media is replaced with fresh treatment media (phenol red free, no FBS) and cells are treated with compounds and incubated overnight (24 hours). Post treatment, cells are rinsed with 1×PBS, lysed and receive the luciferase kit reagent and luminescence is measured.

Equipment:
 Biological Safety Cabinet
 Multi-channel pipette
 Inverted Microscope
 Water Bath
 Bench top centrifuge
 Incubator
 Plate Reader (that can read luminescence)
 Corning 3275 cell culture flask (or comparable)
 Pipets and pipette controller (ex/Pipet Boy, Drummond Pipet)
 Aspirator that uses pipet tips and hooks to house vacuum
 96-well plate (Costar, Cat #3903 or 3610)

Reagents and Materials:
 Dulbecco's Modified Eagle Medium (DMEM) (Gibco, Cat #11054-020)
 Fetal Bovine Serum One Shot, Heat Inactivated (Gibco, Cat #A31604)
 Geneticin G418 sulphate (G418) (Gibco, Cat #10131-027)
 Penicillin-Streptomycin 100× (Gibco, Cat #15140-148)
 GlutaMAX Supplement 100× (Gibco 35050-061)
 0.25% Trypsin EDTA (Gibco 25200-056)
 0.4% Trypan Blue if using hemocytometer to count cells
 1×PBS
 Luciferase Assay System including lysis buffer (Promega, Cat #E4530)

Plating Media:
 500 ml DMEM (Gibco, Cat #11054-020)
 0.8 mg/ml G418
 5 ml GlutaMAX
 50 ml FBS
 5 ml Pen/Strep Treatment Media:
 500 ml DMEM (Gibco, Cat #11054-020)
 5 ml GlutaMAX
 5 ml Pen/Strep Starting New Cultures:
 Frozen AREC32 cells (frozen in 90% FBS and 10% DMSO) are quickly thawed and placed in a 50 ml conical tube with 25 ml plating media. Centrifuge at 1500-2000 RPM for 5 minutes. Remove media without disturbing cell pellet. Re-suspend cells in 12 ml media and add to T-75 tissue culture flask. Cells should be at >80% confluency in 4-5 days and can be split 1:3 into T-150 flasks to grow cells for seeding plates if more cells are needed.

Maintaining and Sub-Culturing Cells:

Cells are maintained and plated in 96-well plates with plating media. Subculture (passage cells) every 3-4 days or when ~75-80% confluent. To passage cells, aspirate media from flask and add 6 ml 0.25% trypsin. Tilt flask in all directions to distribute the trypsin over the bottom of the flask and place in incubator. After 2-3 minutes observe cells under microscope to see if detached. If cells have not detached completely place in incubator for an additional 2-3 minutes. Once detached, add 6 ml maintenance media to neutralize trypsin and pipet into centrifuge tube. Centrifuge at 1200 RPM for 5 minutes. Remove media without disturbing cell pellet. Re-suspend pellet in 12 ml maintenance media and add to flask. If splitting or detaching cells from a T-150 flask double all volumes and follow same procedures.

Plating Cells:

Aspirate media from flask and add appropriate volume of 0.25% trypsin depending on size of flask (6 ml for T-75 and 12 ml for T-150 flask). Swirl flask to distribute trypsin on bottom of flask and return to incubator for 2-3 minutes. Observe cells under microscope. If cells have not detached completely place in incubator for an additional 2-3 minutes. Once cells are detached add DMEM equal to the volume of trypsin, mix gently and place in centrifuge tube. Centrifuge at 12000 RPM for 5 minutes. Aspirate media without disturbing cell pellet. Re-suspend pellet in 10 ml DMEM. Dilute the cells 1:5 using 50 µl cells+200 µl DMEM. Use 20 µl of this dilution and 20 µl 0.4% trypan blue. Mix and add 10 µl/chamber to disposable hemocytometer and insert into Countess II Instrument. Non-viable cells will be blue, viable cells will be unstained. Cell seeding density may vary from ~10,000 cells/well or more depending on cell passage growth. Cell density should be approx. 70-80% on day of treatment/dosing. On day 2, replace plating media with treatment media, but do not add the pen/strep. Media must be free of phenol red.

Positive Control:

Tert-Butylhydroquinone (tBHQ) (Aldrich, Cat #11,294-1). Prepare 100 mM stock (1M=166.21 mg/ml; 100 mM=16.62 mg/ml). Dilute to 750 µM (1:133) using 30 µl of 100 mM tBHQ and 3.62 ml treatment media. 2 µl of positive control should yield a final concentration of 7.5 µM in the test well.

Test Materials:

Test materials may be prepared in DMSO or water, with a final concentration of DMSO not to exceed 1%.

Procedure:

Cell Preparation and Treatment:
1. In a 96 well-plate, seed $1.5 \times 10^4$ cells/well in 100 µl plating media.
2. After sitting for 15 minutes at room temperature, place the cells in the incubator.
3. Incubate the cells at 37° C., 5% CO2, and 95% humidity for 24 hrs.
4. Replace the media with 99 µl of treatment media and treat with test compounds (2 µl/well), vehicle control (2 µl/well) and positive control tBHQ (2 µl/well).
5. Add 99 µl of media after treatment, final assay volume 200 µl: Adding half the media after dosing insures better distribution of the materials.
6. Incubate the cells at 37° C., 5% CO2, and 95% humidity for another 24 hrs.
7. Remove media and wash the cells once with 100 µl 1×PBS buffer. Remove PBS and follow instructions for luciferase assay.

Luciferase Assay:
1. Prepare 1× lysis reagent by adding 4 volumes of water to 1 volume of 5× lysis reagent.
2. Add 20 µl of lysis buffer per well. Gently shake plate to distribute buffer in well. Place plate in 80° C. freezer for 15 minutes to facilitate lysis. Thaw plate completely and confirm lysis under microscope.
3. Prepare Luciferase Assay Reagent by adding Luciferase Assay Buffer to the vial of lyophilized Luciferase Assay Substrate according to the manufacturer's instructions. Mix gently. Add 100 µl Luciferase Assay Reagent per well. Ensure there are no air bubbles.
4. Read plate immediately with plate reader (e.g., a Synergy™ Neo2 brand microplate reader available from BioTek).

Calculation of Data:

ARE activation value=Test sample luminescence/ (luminescence of average of vehicle controls)

Vehicle Control=Average cells+DMSO or water (n=8)

Gene Modulation Assay

This method provides a way to measure the ability of a compound or material to modulate the expression of a target gene.

Cells: tert keratinocytes (tKC)
BJ Fibroblasts

Plating: Cells are plated the day before treatment.
For tert keratinocytes: 100,000 cells/well in 2 ml volume of medium/well for 12-well plates (e.g., Collagen I coated plates, Corning cat #356500), or 50,000 cells/well in 1 ml volume of medium/well for 24-well plates.
For BJ fibroblasts: 88,000 cells/well in 2 ml volume of medium/well for 12-well plates (e.g., Corning cat #3512), or 44,000 cells/well in 1 ml volume of medium/well for 24-well plates.

Medium: For tert keratinocytes: EpiLife (e.g., Thermo Fisher Scientific cat #MEPI500CA+HKGS (e.g., Thermo Fisher Scientific cat #S-001-5).
For BJ Fibroblasts: EMEM (e.g., ATCC cat #30-2003)+ 10% FBS (e.g., HyClone cat #SH30071.02).

Wafergen Process: Total RNA Purification and qPCR

Cell lysates are thawed at 4° C. and then isolated using the Biomek FxP and the RNAdvance Tissue Isolation kit (Beckman Coulter, p/n A32646). The resulting RNA is quantified using the Nandrop 8000 (Nanodrop, ND-8000). cDNA is generated using 500 ng of Total RNA and Applied Biosystems High Capacity cDNA with Reverse Transcription kit (Applied Biosystems p/n 4368814). cDNA, assays, and dilutions of PrimeTime GeneExpression MasterMix (IDT, p/n 1055771) are plated onto a Wafergen MyDesign SmartChip (TakaraBio, p/n 640036) using the Wafergen Nanodispenser. The chip is then loaded into the SmartChip cycler and qPCR performed using the following PCR conditions:

Hold stage: 50° C. for 2 minutes (warm up), then 95° C. for 10 minutes;
PCR stage (40 cycles): 95° C. for 15 seconds, then 60° C. for 1 minute. Export data in .txt file format for analysis.

EXAMPLES

Example 1: Formulations

Table 1 below provides examples of the present skin care compositions. The exemplary compositions are made by blending the A phase components with a suitable mixer (e.g., Tekmar RW20DZM or equivalent) and heating to a temperature of 70-80° C. and maintaining the temperature while stirring. Separately, the B phase components are blended with a suitable mixer and heated to 70-75° C., while maintaining temperature during mixing. Phase B is added to Phase A while mixing well to form an oil-in-water (O/W) emulsion. The emulsion is then milled using a suitable mill (e.g., Tekmar T-25 or equivalent) for 5 minutes. When the emulsion is at 60° C., phase C is added while continuing to mix. At 40° C., the ingredients of phase D and E are added to the emulsion. The emulsion is then milled for 5 minutes to provide a uniform composition.

Example 2: Vitamin B3 Compound, Pal-KTTKS [SEQ ID NO: 1], and Ac-PPYL [SEQ ID NO: 2] Synergistically Upregulate NRF2 [SEQ ID NO: 3]

This example demonstrates the ability of a combination of niacinamide, pal-KTTKS [SEQ ID NO: 1], and ac-PPYL [SEQ ID NO: 2] to synergistically activate the ARE Test compositions and control compositions were prepared as described above in the ARE Assay and tested accordingly. The vitamin $B_3$ compound used in this example is niacinamide [Sigma cat #N5535], the pal-KTTKS is PROMA-TRIXYL from Sederma (France), and the ac-PPYL is SYNIORAGE from BASF Care Creations (New Jersey). The results of the test are summarized below in Table 2. N+P+A refers to the combination of niacinamide (N), pal-KTTKS (P) [SEQ ID NO: 1], and ac-PPYL (A) [SEQ ID NO: 2].

TABLE 1

| Component | I | II | III | IV | V | VI | VII | VIII | IX |
|---|---|---|---|---|---|---|---|---|---|
| Phase A | | | | | | | | | |
| Water | qs | qs | qs | qs | qs | qs | qs | qs | qs |
| Glycerol | 5.00 | 7.00 | 3.00 | 15.0 | 7.00 | 5.00 | 5.00 | 3.00 | 5.00 |
| Disodium EDTA | 0.10 | 0.05 | 0.10 | 0.10 | 0.05 | 0.05 | 0.05 | 0.05 | 0.10 |
| Phase B | | | | | | | | | |
| Dimethicone 5 cSt | — | — | — | — | — | — | — | 10.0 | 15.0 |
| Dimethicone and Dimethicone Crosspolymer | — | — | — | — | — | — | — | 13.0 | 15.0 |
| Laureth-4 | — | — | — | — | — | — | — | 0.25 | 0.35 |
| Polysorbate 20 | — | — | — | — | — | — | — | 0.15 | 0.25 |
| Tapioca Starch and Polymethylsilsesquioxane | — | — | — | — | — | — | — | 2.50 | 3.50 |
| Avobenzone | — | — | — | 3.00 | — | 3.00 | — | — | — |
| Homosalate | — | — | — | 15.0 | — | 10.0 | — | — | — |
| Octisalate | — | — | — | 5.00 | — | 5.00 | — | — | — |
| Octocrylene | — | — | — | 2.60 | — | 9.00 | — | — | — |
| Isopropyl Isostearate | 5.00 | 2.50 | 1.00 | — | — | — | — | — | — |
| Isohexadecane | 1.00 | 1.50 | 3.00 | — | — | — | — | — | — |
| Cetyl Alcohol | 0.25 | 0.50 | 0.32 | 0.40 | 0.40 | 0.30 | 0.50 | — | — |
| Tocopherol Acetate | | 0.50 | 0.25 | 1.00 | 0.25 | 0.25 | 0.25 | — | — |
| PEG-100 Stearate | 0.20 | 0.10 | 0.10 | 0.30 | 0.10 | 0.20 | 0.10 | — | — |
| Stearyl Alcohol | 0.50 | 1.50 | 0.40 | 0.60 | 0.50 | 0.40 | 0.60 | — | — |
| Behenyl Alcohol | 0.40 | 1.00 | 0.50 | 0.50 | 0.40 | 0.35 | 0.50 | — | — |
| Ethyl Paraben | 0.20 | 0.15 | 0.20 | 0.25 | — | — | — | — | — |
| Propyl Paraben | 0.10 | 0.15 | 0.10 | 0.15 | — | — | — | — | — |
| Polymethylsilsesquioxane | 1.25 | 2.50 | 1.00 | — | — | — | — | — | — |
| Phase C | | | | | | | | | |
| Titanium Dioxide | — | 0.50 | — | 0.25 | — | — | — | — | — |
| Tapioca Starch and Polymethylsilsesquioxane | — | — | — | — | — | 12.0 | — | — | — |
| Vinyl Dimethicone/Methicone Silsesquioxane Crosspolymer | 1.50 | — | 1.50 | 3.50 | 5.00 | — | 7.50 | — | — |
| Sodium Polyacrylate Starch | — | — | — | — | 1.50 | 1.00 | 1.50 | — | — |
| Hydroxyethyl acrylate/sodium acryloyldimethyltaurate copolymer | 2.00 | 1.50 | 2.50 | 2.00 | | | | 1.25 | 2.00 |
| Phase D | | | | | | | | | |
| Water | 5 | 10 | 10 | 5 | 10 | 10 | 10 | 5 | 10 |
| Pal-KTTKS [SEQ ID NO: 1] | 0.0001 | 1 | 0.5 | 0.25 | 0.1 | 0.05 | 0.025 | 0.01 | 0.001 |
| Ac-PPYL [SEQ ID NO: 2] | 0.0001 | 2 | 0.5 | 0.5 | 0.05 | 0.1 | 0.0125 | 0.005 | 0.002 |
| Niacinamide | 0.05 | 1 | 3.5 | 2 | 4 | 5 | 10 | 5 | 0.5 |
| Dexpanthenol | 0.5 | 0.5 | 0.5 | 1 | 1 | 1.5 | 0.25 | 1 | 0.5 |
| Phase E | | | | | | | | | |
| Benzyl alcohol | 0.25 | 0.40 | 0.25 | 0.50 | — | — | — | — | — |
| Hexanediol and Caprylyl Glycol | — | — | — | — | 0.70 | 0.80 | 0.70 | 0.70 | 1.00 |
| Phenoxyethanol | — | — | — | — | 0.3 | 0.4 | 0.5 | 0.20 | 0.25 |
| Dimethicone/dimethiconol | 0.5 | 1.00 | 2.00 | 1.00 | 2.00 | 2.00 | 1.00 | 1.75 | 1.00 |

Synergy Factor is calculated as:

$$\frac{\text{Observed luminescence for the combination of ingredients}}{\text{Sum of the individual ingredient luminscence values}}$$

A synergy factor greater than 1.00 with p-value ≤0.05 indicates a statistically significant synergistic effect. Preferred synergy factors are greater than 1.3.

TABLE 2

Synergistic ARE activation

| Concentration (ppm) | | | Average Net Luminescence | | | | | |
|---|---|---|---|---|---|---|---|---|
| N | Pal-KTTKS | Ac-PPYL | N | Pal-KTTKS | Ac-PPYL | N + P + A (observed) | N + P + A (expected) | Synergy Factor | p-value |
| 500 | 1 | 2 | 53 | 24.3 | 61 | 200.3 | 138.3 | 1.45 | 0.0011 |
| 500 | 1 | 1 | 53 | 24.3 | 51 | 193.3 | 128.3 | 1.51 | 0.0025 |
| 500 | 1 | 0.5 | 53 | 24.3 | 26 | 182.3 | 103.3 | 1.77 | 0.0017 |
| 500 | 1 | 0.1 | 53 | 24.3 | 22 | 174.7 | 99.3 | 1.76 | 0.0009 |
| 500 | 1 | 0.05 | 53 | 24.3 | 12 | 106.7 | 89.3 | 1.19 | 0.1568 |
| 50 | 1 | 2 | 45 | 24.3 | 64 | 171.3 | 133.3 | 1.29 | 0.0208 |
| 50 | 1 | 1 | 45 | 24.3 | 56 | 184.0 | 125.3 | 1.47 | 0.0027 |
| 50 | 1 | 0.5 | 45 | 24.3 | 14.7 | 172.0 | 84 | 2.05 | 0.0040 |
| 50 | 1 | 0.1 | 45 | 24.3 | 15.7 | 145.7 | 85 | 1.71 | 0.0014 |
| 50 | 1 | 0.05 | 45 | 24.3 | 19.4 | 104.0 | 88.7 | 1.17 | 0.1316 |
| 10 | 1 | 2 | 12 | 24.3 | 61 | 138.3 | 97.3 | 1.42 | 0.0028 |
| 10 | 1 | 1 | 12 | 24.3 | 51 | 128.7 | 87.3 | 1.47 | 0.0041 |
| 10 | 1 | 0.5 | 12 | 24.3 | 26 | 88.7 | 62.3 | 1.42 | 0.0188 |
| 10 | 1 | 0.1 | 12 | 24.3 | 22 | 83.3 | 58.3 | 1.43 | 0.0054 |
| 10 | 1 | 0.05 | 12 | 24.3 | 12 | 63.0 | 48.3 | 1.30 | 0.1095 |
| 1 | 1 | 2 | 8 | 24.3 | 64 | 125.0 | 96.3 | 1.30 | 0.0146 |
| 1 | 1 | 1 | 8 | 24.3 | 56 | 116.0 | 88.3 | 1.31 | 0.0398 |
| 1 | 1 | 0.5 | 8 | 24.3 | 14.7 | 71.7 | 47 | 1.52 | 0.0304 |
| 1 | 1 | 0.1 | 8 | 24.3 | 15.7 | 63.3 | 48 | 1.32 | 0.0719 |
| 1 | 1 | 0.05 | 8 | 24.3 | 20 | 56.0 | 52.3 | 1.07 | 0.6529 |

As can be seen in Table 2, the data suggest that ratios of niacinamide to pal-KTTKS [SEQ ID NO: 1] to ac-PPYL [SEQ ID NO: 2] (N:P:A) of between 500:1:2 and 1:1:0.5 synergistically activate the ARE. However, ratios of N:P:A of 500:1:0.05, 50:1:2, 10:1:0.05, 1:1:2, and 1:1:0.05 do not appear to provide a synergy factor of greater than 1.3. Thus, it can be important to select the right combination of vitamin B₃ compound, pal-KTTKS [SEQ ID NO: 1] to ac-PPYL, as illustrated in Table 2, to provide the desired synergistic effect.

Example 3: Tetrapeptide Specificity Needed for Synergy

This example demonstrates the importance of selecting a specific tetrapeptide to provide the desired synergistic activation of the ARE. In this test, the amino acids from ac-PPYL [SEQ ID NO: 2] were rearranged to form a new tetrapeptide, ac-YPLP. Test compositions and control compositions were prepared as described above in the ARE Assay and tested accordingly. The results of the test are summarized in Table 3 below.

TABLE 3

ARE activation and Specificity of Ac-PPYL to Ac-YPLP

| Concentration (ppm) | | | | Average Net Luminescence | | | | | | |
|---|---|---|---|---|---|---|---|---|---|---|
| N | Pal-kttks | Ac-ppyl | Ac-yplp | N | Pal-kttks | Ac-ppyl | Ac-yplp | N + P + A (expected) | N + P + A (observed) | Synergy Factor | p-value |
| 500 | 1 | 2 | 0 | 45 | 21 | 57 | | 123 | 184 | 1.50 | 0.0018 |
| 500 | 1 | 0 | 2 | 45 | 21 | | 39 | 105 | 96 | 0.91 | 0.3476 |

Surprisingly, as can be seen in Table 3, a tetrapeptide with the same amino acids as ac-PPYL [SEQ ID NO: 2], but arranged in a different order, does not provide the desired synergistic effect. These data suggest that the specific peptide sequence is important for providing the desired synergy.

Example 4: Synergistic Upregulation of Genes Involved in in Cellular Anti-Oxidancy and Repair This example demonstrates the ability of a combination of niacinamide, pal-KTTKS [SEQ ID NO: 1] and ac-PPYL [SEQ ID NO: 2] to synergistically upregulate SLFN5 [SEQ ID NO: 4], GDE1 [SEQ ID NO: 5], MINPP1 [SEQ ID NO: 6] and HMGCL [SEQ ID NO: 7], which are involved in cellular anti-oxidancy and repair processes. Test compositions and control compositions were prepared as described above in the Gene Modulation Assay and tested accordingly. The pal-KTTKS used in this example is PROMATRIXYL brand pal-KTTKS from Sederma (France), and the ac-PPYL is SYNIORAGE brand tetrapeptide from BASF Care Creations (New Jersey). The results of the test are summarized below in Table 4. Fold change shown in Table 4 is based on the combination (N+P+A) versus the sum of individual treatments (N, P and A). A p-value of 0.05 or less is considered significant.

TABLE 4

Synergistic Upregulation of Selected Biomarkers

| Niacinamide (ppm) | Pal-KTTKS (ppm) | Ac-PPYL (ppm) | Biomarker | Fold Change | p-value |
|---|---|---|---|---|---|
| 500 | 1 | 1 | GDE1 | 1.4228 | 0.0198 |
| 500 | 1 | 1 | HMGCL | 1.4687 | 0.0368 |
| 500 | 1 | 1 | MINPP1 | 1.3572 | 0.0195 |
| 500 | 1 | 1 | SLFN5 | 1.6198 | 0.0011 |

Example Combinations

A. A skin care composition, comprising:
 1) a combination of a vitamin B3 compound, palmitoyl pentapeptide-4 (pal-KTTKS) [SEQ ID NO: 1], and acetyl tetrapeptide-11 (ac-PPYL) [SEQ ID NO: 2], wherein the combination of vitamin B3 compound, pal-KTTKS and ac-PPYL increases activation of a cell's Antioxidant Response Element (ARE) according to the ARE Assay; and
 2) a dermatologically acceptable carrier.

B. The skin care composition of paragraph A, wherein the combination of vitamin B3 compound, pal-KTTKS and ac-PPYL synergistically boosts activation of the ARE.

C. The composition of paragraph A or B, wherein the combination of vitamin B3 compound, pal-KTTKS [SEQ ID NO: 1], and ac-PPYL [SEQ ID NO: 2] exhibit a synergy factor of at least 1.3.

D. The composition any preceding paragraph, wherein the combination of vitamin B3 compound, pal-KTTKS [SEQ ID NO: 1], and ac-PPYL [SEQ ID NO: 2] synergistically upregulates at least one gene selected from the group consisting of Nuclear Factor E2-Related Factor 2 (NRF2) [SEQ ID NO: 3], Schlafen Family Member 5 (SLFN5) [SEQ ID NO: 4], Glycerophosphodiester Phosphodiesterase 1 (GDE1) [SEQ ID NO: 5], Multiple Inositol-Polyphosphate Phosphatase 1 (MINPP1) [SEQ ID NO: 6], and 3-Hydroxy-3-Methylglutaryl-CoA Lyase (HMGCL) [SEQ ID NO: 7].

E. The composition of any preceding paragraph, wherein the vitamin B3 compound is present at 0.05% to 10% by weight of the composition.

F. The composition of any preceding paragraph, wherein the vitamin B3 compound is selected from the group consisting of niacinamide, nicotinic acid, nicotinyl alcohol, and combinations thereof.

G. The composition of paragraph F, wherein the vitamin B3 compound is niacinamide.

H. The composition of any preceding paragraph, wherein the pal-KTTKS [SEQ ID NO: 1] is present at 0.0001% to 2% by weight of the composition.

I. The composition of any preceding paragraph, wherein the ac-PPYL [SEQ ID NO: 2] is present at 0.0001% to 2% by weight of the composition.

J. The composition of any preceding paragraph, wherein a ratio of vitamin B3 compound to pal-KTTKS [SEQ ID NO: 1] to ac-PPYL [SEQ ID NO: 2] is between 500:1:2 and 1:1:0.5.

K. The composition of any preceding paragraph, further comprising at least one additional ingredient selected from vitamins, minerals, peptides, sugar amines, sunscreen agents, oil control agents, flavonoid compounds, anti-oxidants, protease inhibitors, tyrosinase inhibitors, anti-inflammatory agents, moisturizing agents, exfoliating agents, skin lightening agents, anti-acne agents, anti-wrinkle agents, phytosterols, N-acyl amino acid compounds, antimicrobials, antifungals, pH adjustors, thickening agents, preservatives, and combinations thereof.

L. A method of treating oxidative stress in skin, comprising: identifying a target portion of skin where treatment is desired; and
 applying the skin care composition of any preceding paragraph thereto.

M. The method of paragraph L, wherein the composition improves the appearance of a visible sign of skin aging.

N. A method of upregulating NRF2 [SEQ ID NO: 3] in a skin cell, comprising: contacting a skin cell with an effective amount of a vitamin B3 compound, pal-KTTKS [SEQ ID NO: 1], and ac-PPYL [SEQ ID NO: 2] in combination, wherein the effective amount of vitamin B3 compound, pal-KTTKS [SEQ ID NO: 1], and ac-PPYL [SEQ ID NO: 2] synergistically increases activation of the Antioxidant Response Element according the ARE Assay.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A skin care composition, comprising:
   a) a combination of vitamin B$_3$, palmitoyl pentapeptide-4 (pal-KTTKS) [SEQ ID NO: 1], and acetyl tetrapeptide-11 (ac-PPYL) [SEQ ID NO: 2], wherein the combination of vitamin B$_3$, pal-KTTKS and ac-PPYL synergistically increases activation of a cell's Antioxidant Response Element (ARE) according to the ARE Assay and exhibit a synergy factor of at least 1.3; and
   b) a dermatologically acceptable carrier;
   wherein a ratio of the vitamin B$_3$ to the pal-KTTKS [SEQ ID NO: 1] and to the ac-PPYL [SEQ ID NO: 2] is between 500:1:1 and 1:1:0.5.

2. The composition of claim 1, wherein the combination of vitamin B$_3$, pal-KTTKS [SEQ ID NO: 1], and ac-PPYL [SEQ ID NO: 2] synergistically upregulates at least one gene selected from the group consisting of Nuclear Factor E2-Related Factor 2 (NRF2) [SEQ ID NO: 3], Schlafen Family Member 5 (SLFN5) [SEQ ID NO: 4], Glycerophosphodiester Phosphodiesterase 1 (GDE1) [SEQ ID NO: 5], Multiple Inositol-Polyphosphate Phosphatase 1 (MINPP1) [SEQ ID NO: 6], and 3-Hydroxy-3-Methylglutaryl-CoA Lyase (HMGCL) [SEQ ID NO: 7].

3. The composition of claim 1, wherein the vitamin B$_3$ is present at about 0.05% to about 10% by weight of the composition.

4. The composition of claim 1, wherein the vitamin B$_3$ is selected from the group consisting of niacinamide, nicotinic acid, nicotinyl alcohol, and combinations thereof.

5. The composition of claim 4, wherein the vitamin B$_3$ is niacinamide.

6. The composition of claim 1, wherein the pal-KTTKS [SEQ ID NO: 1] is present at about 0.0001% to about 2% by weight of the composition.

7. The composition of claim 1, wherein the ac-PPYL [SEQ ID NO: 2] is present at about 0.0001% to about 2% by weight of the composition.

8. The composition of the claim 1, further comprising at least one additional ingredient selected from vitamins, minerals, peptides, sugar amines, sunscreen agents, oil control agents, flavonoids, anti-oxidants, protease inhibitors, tyrosinase inhibitors, anti-inflammatory agents, moisturizing agents, exfoliating agents, skin lightening agents, anti-acne agents, anti-wrinkle agents, phytosterols, N-acyl amino acids, antimicrobials, antifungals, pH adjustors, thickening agents, preservatives, or mixtures thereof.

9. A method of treating oxidative stress in skin:
   a) identifying a target portion of skin where treatment is desired; and
   b) applying the skin care composition according to claim 1 to the target portion of skin during a treatment period.

10. The method of claim 9, wherein the vitamin $B_3$ is present at about 0.05% to about 10% by weight of the composition.

11. The method of claim 9, wherein the pal-KTTKS [SEQ ID NO: 1] is present at about 0.0001% to about 2% by weight of the composition.

12. The method of claim 9, wherein the ac-PPYL [SEQ ID NO: 2] is present at about 0.0001% to about 2% by weight of the composition.

13. The method of claim 9, wherein the method improves the appearance of a visible sign of skin aging.

14. A method of upregulating NRF2 [SEQ ID NO: 3] in a skin cell, comprising:
   contacting a skin cell with an effective amount of the skin care composition according to claim 1.

* * * * *

SEQUENCE LISTING

```
<160> NUMBER OF SEQ ID NOS: 7

<210> SEQ ID NO 1
<211> LENGTH: 5
<212> TYPE: PRT
<213> ORGANISM: Artificial Sequence
<220> FEATURE:
<223> OTHER INFORMATION: Description of artificial sequence: palmitoyl
      pentapeptide-4 (pal-KTTKS)

<400> SEQUENCE: 1

Lys Thr Thr Lys Ser
1               5

<210> SEQ ID NO 2
<211> LENGTH: 4
<212> TYPE: PRT
<213> ORGANISM: Artificial Sequence
<220> FEATURE:
<223> OTHER INFORMATION: Desription of artificial sequnence: acetyl
      tetrapeptide-11 (ac-PPYL)

<400> SEQUENCE: 2

Pro Pro Tyr Leu
1

<210> SEQ ID NO 3
<211> LENGTH: 34829
<212> TYPE: DNA
<213> ORGANISM: Homo sapiens

<400> SEQUENCE: 3
aaatcaggga ggcgcagctc ctacaccaac gcctttccgg ggctccgggt gtgtttgttc       60
caactgttta aactgtttca aagcgtccga actccagcga ccttcgcaaa caactctttg      120
tctcgcgggc gagagcgctg cccttatttg cgggggaggg caaactgaac gccggcaccg      180
gggagctaac ggagacctcc tctaggtccc ccgcctgctg ggaccccagc tggcagtccc      240
ttcccgcccc cggaccgcga gcttcttgcg tcagcccggg cgcgggtggg ggattttcgg      300
aagctcagcc cgcgcggccg gcggggaag gaagggcccg gactcttgcc ccgcccttgt       360
ggggcgggag gcggagcggg gcaggggccc gccggcgtgt agccgattac cgagtgccgg      420
ggagcccgga ggagccgccg acgcagccgc caccgccgcc gccgccgcca ccagagccgc      480
cctgtccgcg ccgcgcctcg gcagccggaa cagggccgcc gtcggggagc cccaacacac      540
ggtccacagc tcatcatgat ggacttggag ctgccgccgc cgggactccc gtcccagcag      600
gtgctgcctc ggccctctgg gccctgcggt ggtgccggga cggggcggg ggagctaggg       660 aaccgcggcc cgggagggac agccgcaacc ggcttccccc acgtctggcc agagccagga      720
ccgcggcgct gggtagagcc gccgcgcttg cgccggggca gggcggggag gggcagcggg      780
gacgcggccg ggtgatccga ccgaccacga gcccgagggc gaacgggtgg gaagttgcgg      840
```

```
gaaggtctgg ggactgagcc cgctcgcgtg ggccttgggg gagaatccag ccgcgtcccc      900
gggcccgaga gctgggactc cggagcccct aagtttgagc ggcccggtgg gcggcggggc      960 aagaggggc ggacgctggc cgtctgagcc ggcgcggccc ggcccttccg gggctgcgcg      1020
gctcccccgc ctcggtgccg gcaaaaatgt gcctagtcac ggggccgctc tcggggggaac     1080 tgaggtcgcc ttcgggctgg gacccggagc cccttcgccg cgccccaaga cctccttgag     1140
tgcgggctgc gacgcgctca cccgctgggg ccgtctgtgg gcgcggcttt gcgaagtcat     1200
ccatctctcg gatcactctc tggcagcctt gagctctctt gaaagcccag ccccgggacg     1260
agggaggagc gccttaagtg cccagcgggc tcagaagccc cgacgtgtgg cggctgagcc     1320
gggccccgcg cactttctcg gccggggagg ggttcgggct cgggcacccg gagttggccc     1380
ctcgtaacgc cgcgggaaag tgcgggcgag ggcagtggac tctgaggccg gagtcggcgg     1440
cacccggggc ttctagttcg gacgcggtgc ccctggtgg cgctcaccgc gcgcgtggcc      1500
ttggcttccg tgacagcgct cggttggccg tcacagcagc cctcggttgg ccctttcctg     1560
ctttatagcg tgcaaacctc gccgcgccag ggccaaggga caggttggag ctgttgatct     1620
gttgcgcaat tgctatttc cccagagcgg cttttgtcttt ggatttagcg tttcagaatt     1680
gcaattccaa aatgtgtaag acgggatatt ctcttctgtg ctgtcaaggg taagagttgc     1740
gagtgtagat tagaatttct gttgcttta gtctgttagt aattttttgc tttcagctat     1800
tatttctccc ctgagtactt tatatatgtt ccttttcag ttgagaattt gcctcaattt     1860
cttaacatgt tccccctctt ctgcaggggc agagagtgga acgcttgcgt ttcaaaacac     1920
ttgctaattt ctgtgaattg ttataaaagt gaaagaagt ttctgctcat cctttgtaga      1980
aactttaaaa gtagatattt atatttctaa cttctttgt aaatgaattt taggaaaaaa     2040
attggaattc aaggaaatgt gtacttgatg tacagtaaat acgtttatgc tgttaaatgt     2100
aaagttttcg gttaattcca aagatctatt gtaaagtttt aagttatgga caatgtatta    2160
attgtgcttt ttccccctt taaagttgtt tgtcttgaac ttttccccag tcttcattgg     2220
gattgtattc ttctggttcc aactagtgaa gaattaaatt gtaccttccg atttatttaa    2280
tagctgctgt tcaagagtta tctataggaa tgcttgtttg actgaaggat atatgataaa     2340
aatgaacttt agttttctg atttccggaa ttgtctacag ccctctatta ttttgaatt     2400 tttctttctt tgctgtgtaa tataacattc cttatacaaa aatgcgtgaa acatatgtac     2460
cgcattaagt gtgtatttc caattacgtt tgataaaaat aactgcttt ctacctttgt      2520 aatcagacat cgatttgcat atttgaaaac agaaaaagaa caagaaaatt tagaattgat    2580
tttgtttatg attcatatta gattgttgtc atccataaag atttgaacag agtcaaacat    2640
tttcttgacc ttttgtcaaa aaaaactctc caggtgtgaa gtggtagtag gatatagttt    2700
ttcaccttct gtgcagagga tgtgttgata aacagggcag taaggagagc cttagattca    2760
gtatctccat taggtggaag gaaccatcca ttactctttt caagggtgtc ttggagagat     2820
aaagcacttt cctagatgag ggatgaagtt gatattgaaa tagaccgatg agattattt     2880 taagtcaaac aaaagaaaaa taggacaggc ctctcatctc ctgaatgaat gttaagcaaa    2940
gaacaacttg acttttaga tatgtgaaaa atctcttgag aggttgtgga agcagcatgt     3000
aggaggataa atgcataact cacatcagtc ttttacgcat taaaaataac ttgggccatt    3060
ttgaaatctt tctttcttgc cctgggttct tataagcaat gttgggggga aaactgactc    3120 tgtcttagg attaccagga aaagttgaaa gccaaatgca tcatttttct taatatttgt    3180
ttttattgag gataaatcat gtttaacaaa gctgcatgaa aaaaaggaac ccaacaagta    3240
```

```
cattttttttt tctgggaatt tcctctgtcc tgactgaaga catttaaagg gggttttgtg    3300
tcaatatttc ctccttaact gttcctcaag cctgggttaa cttttcagta tgcaggaaga    3360
atttggcact aagataataa tagataagtt actgggcacg tccctgggtg ccagacataa    3420
ttgcttcaca tgcataattt tacagtaacc tcacggaaa tattattatc cctggtttcc     3480
aggttgggaa aaccaggcat aatagttaga tcaggcatta ggttaggaaa ggttaggaga    3540
gaggcataga gaaaggccag gacctgctaa ggtgaccata ctattgagtg ccaaggtag    3600 cattcaaaca ggtttgactc ctgggggctt ctaatcacca cttccagact gtaccaaaac    3660
tccttaaact ctaaatagga agaaaagctc acactttaaa aagtgggtaa gttgagattt    3720
gcctattctg ggggaaggag aggccggaat ataaagatt aatgtctgca gcttttccat     3780
ttagcaagac atttaatcac tgtatgtgac gtggggaggt ggaccttgtt aaatacaggg    3840
agagtgaata caatccatca atggtaccca ctgtggtcct tttaaggaag acacagaggc    3900
ctcggtggat tcaatttaga aaggcaggac tgttttttgt tttttgtttt tttttttttt    3960
tgagatgaag tcttgttctg ttgcccaggc tggaatgcag tggcctgatc ttggctcact    4020
gcagcctcta cttcccgggt tcaagtgatt ctcctgcttc agcctcccga gtagctggga    4080
ttataggcac ccactgcccg gctaattttt gtattttag tagagatggg gttttaccat     4140
gttggccagg ctgggctggt ctcgaactcc tgacctcagg tgatccaccc gcctcggcct    4200
cccaaagtgt tgggattaca ggtgtgagcc actgcgccag tctgtttctt aatataataa    4260
tagttttaaa aatttctgat gtttggcaat gtccaagatt ctgcctcaca ttttcagaa     4320 actgcttttt ttcttaatta aatctcttag ctactggagt ctttgccttt gtttgccttg    4380
ctacttggta catttcttct gttccattgg ctctttttgt tttgaagtag tgctcaaaaa    4440
taagtttggt agtaagaata tggtgaagag tgtgacagac agggttaaac caggctgaag    4500
gaaagagagc agaatgggga aaatttgagt tgaaaacagc tagcagaaag ctgatggcgc    4560
aaattcaacc ctaatctcat gttttggcac ttctgaacta tagcaagcat aagggctcaa    4620
ctcttatcta gttgaagctt acttgggtct ttgagaatag tacatctcaa aattaaacac    4680
tttcttagtc cttattgtta agttgttttt ggaattattg tcttatttgt ctgaattaag    4740
tgtgctgcag gacttatagg atctgatgga tgatttgcct aaaagttggt ccaggtcaac    4800
ctcagggcat ttaaatgctt ggtccagcca ctttctgaaa gttgactgaa atatgttgca    4860
cagcagggta gaggaggaca agtttactag atgtcatttt taacctgctt gtcttcatct    4920
ctgactgtag aaatgtatat tcattataag tttgccacaa atagagaata gagtttattc    4980
tttgatcatc taatttctag gagctattga aatttcactg ctacctgctt ttaaataagc    5040
gccaacaaac atttattaaa agggctttaa ggtataggcc aagatttatt caattgctaa    5100
tggtatgttt tctgtaaatg aaagcaaaaa tatgttcaag tgtataatat taaatattaa    5160
cattcagaaa cttggagaaa tacagatggc ttttttttt gagacgcagt cttgctctgt    5220
cgcccaggct ggagtgcagt ggcatgatct ccgctcactg caagctccac ctcccgggtt    5280
cacgccattc tcctgcccca gcctcccgag tagctggtac tacaggcacc cgccaccacg    5340
cctggctaat ttttgtatt tttagtagag atggggtttc actgtgttag ccaggatgat    5400
ctcgatctcc tgacctcatg atccgcctgc ctcagcctcc caaagtgctg ggattacaag    5460
cttaagccac cgcgcctggc ctagatggat ttccttgtacc agactatacc ctagacatga    5520
aaacaagact gttaaacaaa atcctgtgct acctaaagtt tgagccttct gtgtgtcagt    5580
```

```
ttctgccata taaataact cttaactatg attattaagt atattaagaa ctttgagtag   5640
gggaggcacg tttaatcatt cgttttacg gcatatgtac tataatacct gtgtgttgca    5700
aatcctggta tttaaaagtc ttttgtgta tttgagcatg taagtttatt tggtccaaac    5760
tgctggtact agtaaagaca agtccagggc ataagtagga cttacagcac caagttcgtc   5820
tttttttttt gagacagagt ctcagtcggt cacccaggct ggagtgcatt ggtacagtct   5880
gggctcactg caccctccac ctcccgagtt caagcgattc tcctgcctca gcctcccaag   5940
tagctgggat tacaagtgtg tgccgccacg cccggttaat ttttgtattt ttagtagaga   6000
tggagtttca ctatgttggc caggctgatc ccgacctcag gtgatgtgcc cacctttggtc  6060 tccgaaagtg ctgggattat aggcgtgagc cactgcgcct gacctccaag tccatctttc   6120
aaaggctctg ttgataattg actcttgaga gtcattacag tccatcaaca gcctgtattc   6180
tgaatatttg ttttaattc taagacaatg ctaaatagcc attccaaata aggtgagaac     6240
tgagacttta gggcctgtat tatcagctgt acactgacaa gctctgaact ctattgcttt    6300
ttcaaatcag agaagaaaaa tgagtaagaa agaaaaata tggatcactt aggctttgat    6360
gcctcctctg agtttatagt gtttaccttc tgtattactt aggtgatcct ctctaatggc   6420
attttaaatc tctgttgata cttgtcttac ttatgtatct gttttttttt cctctatagt   6480
agatagaatt tatagatata tatgtatttt aaagtaagat acaatttacg taccttacaa   6540
tttacccatt taatctaatt cagggttatg caacccctatg aatttagtag tttattcata  6600
gagttatgca accatcactg taatcaattt tcaacaccct caaaagaaac cccatatcca   6660
ttagcagtca cttcccatt ccctcaact ctcctggccc ctggtaacta ctcagttatt     6720
ttctgtacct atggatttgc ctattctgga catatcatgt aaatggaata gcatgtaaat   6780
ggaatcatac agtatttatc cttctgttgc tggcttcttt cacagcaata tgttttcaag   6840
gtttaaaaat gttgcaacgt atatcaatag cgtcattcct ttttatggct gcatactatt   6900
ccattgtatg gctataccac attttatta tccagttgat gatcatttga gttgtttcca    6960 cttttatgt ttctgtttgt ttcttacagc agtggttctc aaactgttgt atattagact    7020
caccatcagt atttaaaaaa ctaatgccca ggccatatcc ctcatgaaat caaaatctct   7080
gggggtgggg cccaggcatc actattttt aaagattctg aggggattct aacgagcagt    7140
caggtttgag agccagtgcc ctagggcagc agtccacaac ctttttagca ccagggacta   7200 gtttgtgga agacagtttt tccatagaag gaggtagagg atggtttcag gatgaaactg     7260
ttccacctca gatcatcagg cattagattg tcctaaggag ctgcaacct acatcccttg     7320 catactcagt ttacaacagg gttccggctt ctctgataaa ctaatgctgc tgctaatctg    7380
acaggaggtg gagctcaggc gggaatgctc gcctactgct cacctcctgc tgtgcggcct   7440
ggttcctaat gggccactga cccctccgca gccagcaggt ggggacccct gccctagggg   7500
acccacctca gtgcttggta tccattgaag tatatagtga tttagaaaat ctggttagga   7560
tgtcttattt aaatcatgaa agcaagtgct tttgtctttg atcattgccc ttcacagcct   7620
tacagttaac acctacattc aggaactgtg tttcaaagtg cctggcgagt gtttgaaact   7680
cactaaatat atataacctg ggctcattaa accctccag aagatttggg taactttgtt    7740
atgaaagggc ttccctgaag tgggtcagca ggattgctct gtgttttttc aggaatgtgg   7800
cctgtgataa cttgcaatct agattatttg gaaatagcac tgagagaagc cagtgaggac   7860
agaatgctca gaagctttggg ataggtgttg aacatcctgg aggccaggac ggaacactgt   7920
cttactctag gaagctgtgt tcctgggcct cattatcttc ctccgttaaa aacaaaagac   7980
```

```
ttaaatctcc acagcagctt tcagcaactt catttttttgg ttctctgtat ctgcctgata   8040
aagtcccact ttgtagtggc tcccacttat atttacctga atggcttttg ggttgacata   8100
tttggaaact ggggctaact tccaaactgt tggcaacttg tgtgtgggtg tgcgtgccac   8160
agcacagcag tcccacttga gagacttgat ggtgtggtgg tggttggggg gcttctgaag   8220
ctggcttagc cccagcccta tacacccacc ccacagatgg tgggaacaag cccagaagag   8280
agtgggtaac tctgtccact gtggcctcca cagccaaggt tgccaggcag agctcgcaag   8340
gcccaattcc agtcttgtct ttgaccgttg cccctttgtg ttgggggggt gtatttagtc   8400
acctttctgg aagcatgctt ttctaattct agtcatcagt agtttgttgc tttaagattt   8460
tgaaaatggt atcctgttat tttacttagg agtttcgtat tgaatggtgt acataatgtg   8520
attcaagtac ctcaaaacag aaggacttca gttaagattt aggctctatg caacatacac   8580
ttcttgcatt ttctcattca atgtcctttc cttttttttt ttttttttttt ttgcaagaat   8640 gtagctgaca ttcagagtag attagtacct tcaatgtctg tgtgaaagaa atgaccttaa   8700
tatgaggaca atattgactg tgtatttagg gggcccactg ttaaggcata tagaattttg   8760
ctttatttca gacctgacaa tctccttgtct gctctgcttc cgcataaaat tataatactg   8820
cacatggatg taaaacccaa cctattccct gcctgaggga ctagaataga gggaagaatg   8880
actatagttc tttgttgcct tttgtgaagg taacaggcac agaggtatga tgcatgatgg   8940
aattatatac ctcttcttga ggtgtttgag ggctgactaa ggacctgtac ttttttttttg   9000 gtttgttttg cagtactggg gccagggagc cttgctgttg tgtctagaga gtgttgaaga   9060
accatgaata tttcgcaaaa agaaaataat tttttttaacc attaaaattc ctggtagtga   9120
cttcctctgg caagtaaaaa actctcattt tccttaaaaa atgagagttt tttacttgca   9180
ataggaaaac ttgccaattt ttcaagttat ttttattctt gatgattctc aatgagacat   9240
aattaaaata cacatagaaa aaacaaccgt aggccaggtg cagtggctca ccagtaat    9300 cccaacactt tgggaagtca aggtgggagg atcactagag accaggagtt tgagatgagc   9360
ctgggcaaca tattgagaca ctgtctcctc aaaaaattaa aaaaattagc tggatccagt   9420
ggtgcacacc tgcaattgta gctatttggg aggctaaggt ggaagaatag cttgagccca   9480
ggagtttgaa ggtgcagtga gccataatca tgccactgta ctccagccca ggcaacagag   9540
taagatcatg tctcaatgaa aaaagaaaa atcaaccctaa gtggactgga acagggctgg    9600
tttactttgt gtcagctgca gtgcccccac tcgccaaccc acatgttctt ctcctgctgg   9660 tcccaagca gagaccagaa ccaagaatga gaatcatcct gtgggtgcag gttgtatctt    9720
atcctccaga gacagcactt caccctctgt tagaaacttc tttaccacac tgcctgtttg   9780
gtgaaatcct tagggcagtg acttccaaac tgtgatccag gggccaccct tggtgggagg   9840
atcaggaagg aggggggaatg tatcttaaga aaagttgggg gaagctcata tctcttctcg   9900
ttgatcctga gaagtaaagt ctttcctcct cagagagatg cgggtagaca tgactcgcct   9960
agatagaagc tcattcatct ccctcccttc tgcctctgca ggactcttgg aagtctgggt   10020
ccccgggagt atgcggctct tgctctgtgc tacaggtttc caaagttcac ttgataacag   10080
tacaattgtg ctgtaaattg tgcagtaatg agactgagg aaacaattag tctttcatct   10140
tcattcatgt taccagctca cttcctatgg tgtgaaaaga gccagacttt ggagttagga   10200
gacatctgaa tacagacaga actggcaaga ttatggggaa gaaaagggaa aagtaatgaa   10260
tattttcaaa gaggttaagc catttggcca ggacaacact gcttgcaggt agcagaactg   10320
```

```
ggattttgac tgtccataat ccctattctc tgcttgtttt actccttccc tctcttcttt    10380
cttttttcat tgtctaatga cctacagaca ttctgtcagc tgctaaagaa tgagggactc    10440
ctttataaag attgatagga cagtgtcgct acttaaggag ttccttccat gtggaccagt    10500
gggggcgctg ttgacgcatg gggctggact tctctttgga gcagagtcct gttccacgga    10560
tcgctgtgac aagcagaaag tgccccaccc cacctccata caattcctaa tgctcctggg    10620
tgatacaacc gccccagtgg aagcacggtg gtgcatggac ttctagagac catttgaagc    10680
caggacattg ctgcttgttc ttaggaaatg gcagaatatt actttcttgt tttttgtagg    10740
gaagcctgcc atctcaccag gtggcagctt gtttatacct tttatcctaa cctgaagcag    10800
gtgatgggac agaggtcatc gaatataatg aaagtgccac aaaggtagag tctgggtata    10860
ttttatttat gcaggtagag tgacttgtcc agatcccttc acacagagca acatttaata    10920
tggtaattgt tactgctgaa gttggccatt tctcggacct acagctgcaa ggaattggta    10980
acaaaaggat aaactaaaca ttgttactat tttaattttc aaggagatga agttaaaatc    11040
atatatgtca tatctctctg gggcttagcc acctttctg ctgggcactt tttgaagaag    11100
tctgaatact gagataggag agtaaagggg ggaaagtaag tttgcccact tctcatcctt    11160
tttctgacca tcagcctgag ggaagtaact agaatccgct aagaaaattc acttaatcag    11220
cagttgattg attgttatat tgtccacatt gcaaaattct ttaaaggata tttgaagata    11280
ttatcacatt tgttctctta caatctattg tattgtttat ttgaaggggt gagtgttaat    11340
agttcttaag atatcgtact ttatttccgg tagcatatcc aagaaataat ttagaagtat    11400
tgttaatggg aatgatgtta ataattttt ctatgactag tagttgggac atatatgata    11460
taaaacatgg tatctttgtt acttaagtaa tttgaactct aaccccatat atcttaggta    11520
gacaatgaaa atactgaatt gttagtctaa ataatataca cgtactcatt ccgcaaatat    11580
ttattaggta tctacacacc ctaggaatct ttcagggcat gaagctgttt taatcttcca    11640
agataatgca gcacgtatcc cccttgaggg acatttgttt ttcaaattgc tcctctgtgt    11700
ctcctctgct taggatatga gttcctctaa gactgtattt taatctttg tgtaattctg    11760 atgtctagcg ccatgcctgg tgcttacgta atagttgctc agtcagtttg agggtgagtc    11820
cattaactgc cctctaggag cttgatattt aatataaact agtctgtgat acatgacaat    11880
gctgtgacag tgcagatgag aaaatgtgac ttctaactgg ggtgctcaga gaggatatcc    11940
tggaggaact gccattttaa ctagacttt ctttttaagca ggtagatttt gtttggttca    12000
ggcttcagct ggaagcccaa gcaatggtgc agatatgagc tggactatga cagactattg    12060
ggccagtggg gctgacaagg ttaacttggg ggttgccata gagggccttc agtgctcatg    12120
tgcactgttt caagtttgta cagggcatct ggaaaccatg gaagaagatt ctggaaaggg    12180
cagggcaggt aaactggatg tggataggaa gttactgtgg caggtgaatt ggaagatgga    12240
caggttggag gcagggagat ggtgagcggg ctcctgccaa ggtgtaggtc tgagcattgt    12300
tgtgacggct tagttggttt gacatcagca cacagattga ggatctgtca ttgtaactct    12360
aaattgtatc cttgttagac atgtaaaaat aactttttag agcctccgtt tttaaggagg    12420
gaagtggatt gtgctcaagc ttgcatgctc cgctgttcct gtgctttaaa aatactcatc    12480
caccagtgtg gtcactgatg aaaggggagg aaaaactagc cagaagttgc cattttgctt    12540
aaagaatgga ttcatttctt cctcaaggtg gcacagagag agtttctctc ttttttgcccc    12600 tctcttagat tgatttacta ttttagtaa attctaacag tctgatcctt gcttccaatt    12660
acaatgatta gcaatatttg cccaagacaa gaaaaaacaa tttcctctct tttctctcct    12720
```

```
atgagctttt cctgtgagcc ccaagcagac agatgtggac atctagcaat gctgttaaca    12780
acagctgcag tccgttggac tctctgcaac actgggcacg gtacaaagtg ctctgacaaa    12840
ctcttctgcc ctttgcaatc cttactacgc cctgtgaggt gaggagtatt cttcctgttt    12900
tgtaggtgaa gaactgaggc aaagagaggt tatgtcatta gatttcacaa tagggtgtgt    12960
ttccgtttca tcatctttag attgatgtta ctgtgacatc atcttcctag aattaacaaa    13020
gtgaactggg cacaggaaat agcacatggc acaccttcag caaatggtgg ttgtgatcat    13080
tttcatcatt ccatttcttc ttgaaaaaaa tcccttttt ttttttttt tgagacagag       13140 tctcactctg tcgcccaggc tggactggtg tgatctcggc tcactgcaag ctccgcctcc    13200
cgggttcacg ccattcttct gcctcagcct cctgagtagc tgggactaca ggcacgggcc    13260
accacgcctg gctaattttt ttgtattttt agtagagacg gagtttcacc gtgttagcca    13320
ggatggtctc gaactcctga cctcgtgatc cgcccacctc ggcctcccaa agtgctggga    13380
ttacaggcat gagccaccac gcctggcaaa atcccctcga gttccagtgt aaacactcac    13440
gccctttttt gctgtttgct ataaacctct cattctcctt ggtcttcttg tccttgtgtg    13500
aggtcctggt tgttgtggag actgaggtct tctgagacag aaaaccaacc ccatagcagg    13560
cctggtgtgt gccctagaat ggcagaggcc ccacacgttg ccccggctcc tctggaagac    13620
cctccagcct gtctgctgga ttccttgtac ttatgaggat tgttaaacca tctcatagga    13680
ttcctttcca gactcagccc ttcacttgtg gcagcatttc ttactctgag gttctgggcc    13740
tagaaaccca gtgtccatag gcaaggtcta gggacagaga gagtttgtag aaagtgggaa    13800
tgcatcagtg gaaggctaaa tccaaacagg aactgagctg gcctgggtgg ctttgtcctt    13860
ttgccatctt cgtaaccctt taaaggcttt aagacacttc ttttgtaata actaccccaa    13920
ctaaatttgg ccagagctgt gaagggaaag aaaatctaag acccttgagg gagatgacag    13980
ccgaacgttt tacattttta ccaccttttgt tgttgccatg cacagctgat acataaacaa    14040
gtaatggcct catcttctat tcttttattt actggttaga cccagaaccc taaaaggtag    14100
atgcttctca tggtcatttg gcatttgcaa caggagctga atttattaat agtactaata    14160
cctcatcctt ggacatcctt gggttgtccg atatttttaa ggggcattta catcctttgt    14220
ttttcatatg gaaaacttt ccgtaagggc tggtatcatc ttggccttcc attgcaggaa     14280
cagcacaggg aggttcggtg gctaggccac agttacccac gcagctaggt agcagcagag    14340
gccccacctg gcaccccctg gcttcctaag cacatcgcac tgtgcagcct ccctgaggaa    14400
gcctcgagtg gataggaact ctggttcttt aagataaacc tgagttggat ctcactgtca    14460
ccatttatca gatggggcga tgtcttcagg caaaagtact taacctctct gtttttgttt    14520
ccttactcca aaatggtaat gatcatacta ctacccacct gggtggattg gtgtgcatat    14580
gaaggaggtc atgggacaa gtggttggaa gagtgttgag cacatagaaa gtacaagata     14640
aatggtggcc attatgttac tactagact atatcatact tgtctttatc tgggcttaga     14700
atcttgacac tgagatcttt cattctcaga tcttaatatg aaagcttacc aggtaaacac    14760
taccccaaca taattattta gtgggttcat acatgtgaaa gcagttgaaa tacaatttct    14820
gaactccggg ttaatttata tccttagttg gaacaggtag taccctccca gcacctaagg    14880
cctctcactt ctatccattc ttcagatgac ctttgcaata atcatggtaa ttgaatagca    14940
tctgcaccat aacattgttg aataacatca aaatgatcca tttagccatc atgagccttc    15000
ctagtaattc agactcacac cagttctttc aggttattga gtagctttta caaataattg    15060
```

```
ctaacagtac aaatactgtc tcaggtattt tggaagggtg aattttccca ttgatttcag   15120
tgtatcttta ggaggtaatt tgcaaaaccg aagagtttgg ttccgtcaaa gtcacccta    15180 aggagtgtgg aggaccacat tgtaggttta tactgcactg tccctcatgc ttgaaatttg   15240
gctcatgcaa ccaaggaact gaatttttaa tttcgttaaa ttttgattta aattttaaaa   15300
cagaaatagt ataaaatatt tttctgttaa atataccttg tagtgttggc aagactacat   15360
ttcgtgttac catgctgggt aagatttctt gtagtgtgta ttgtgttttg tcacctcgtt   15420
aataattttc ttattttggt tgcatgttaa aataatttg gatatattgg gttaaataaa    15480
tatattgtta aaattaaatt cacttgttta ttttttttgtt ggtgaggcta ggctactaaa  15540
aaatttaaaa ttacccatgt ggattgcatt atatttctat tagtgctgct ttagctgcaa   15600
gtagcctatt taaaaaaaat cattattttc agacttatgg acttcataga atcagaggta   15660
tttagaggaa aggatcttgg gggtcaccta atccagctcc aacattttgc aagtgataag   15720
accaaggcca gaggctacaa taaaatgact gacctcctcc cagatgggga ctggatccca   15780
gtggctttat agcctttgcc ttggatcctg gttttacttg gaaacatagc agacatcaga   15840
gctgcagaga acttctacca gatccggagt gaagaaaatg ccttatttat ttatttattt   15900
atttatttat ttatgagac cgggtattgc tgtggcctag gctgtagtat agtggcagaa    15960
acatggttca ctgcagcctc aacctcctgg gctccaggat cctcatgcct caaccttctg   16020
agtagccggg gccacaggta cgcgccacca cgcctggcta tttttttttt tctcttttgt   16080
agagactgcg tcttccatgt tggccaggct gatatcaaaa ctcctgggct caagtggtcc   16140
tcctaccttg gtcccccaaa gtgctgggat aacaggtgtg agccatcatg cctgttttgg   16200
cagtttttag gggcccacgc taattttgag ccaggtttgc gcttgataat gtaatgctgg   16260
aggctgggca ggggacatga tctgcctgaa agggctgaga actgggaggc tcttattcct   16320
atagtattga gagcaaaggc acagtcttac agaaccacac aatattcaga gcttgtgggt   16380
tggagaagga aagtccctctg aaaaataaaa aaaagagtac agaggccaga ggcggtggct   16440
catgcctgta atgccagcac tttgggaggc ccaggcaggc ggatcaccta aggtgaggag   16500
atcgagacca gcctgaccaa catggagaaa ccctgtctct actaaaaatg caaaattggc   16560
caggcatggt ggcgcatgcc tgtaatccaa gctactggg aggctgaggc aagagaatcg    16620
cttgaacccg ggaggcggcg gttgcggtga gctgagatca cgccattgca ctccagcctg   16680
ggcaacaaga gtgaaactct gtctcaaaaa aaaagaaac agagtacagg tcagacattg    16740
ggcaattttc tcataacaat ttcataggcc attaatttgg ttacagactt gaatagcaca   16800
caacagttct ctaagggtca gtttccaaag taattcctaa tatttaatga attttaagt    16860 gatagaaatt gcagtaggaa agtctagctt gaaatctaat ttgtgttagg ttgaccaggt   16920
gacaaccacc caccctgga ttctgctcag ttaggtcaga cctggggcca gttgcccatt    16980
tagcatctca ggcctcagga tcctcattta taaacctggg gtttgaactg cggtctccac   17040
gatcactgtc agctctcctt agtcagttgg ttgttctaaa tgtagtttag tggccagtaa   17100
acacctgttc ctgagtgata catctttaag gagccggtag atgggtcaac ctggctggac   17160 ttgcttttc aagtctgcct tgtctattag aaaggctgag cttactgatt ttgcctgtca   17220
cgtttgagtg ttcctgagac tttgcccagc ctcggtctta tctgcgggta ccccagcctc   17280
tgcattcctt gccctacaa aatgtgctgc cagttccaaa ggcacaaatg aaaattagct    17340
tggctggagc atggctaggc acacaccagt ggttaaagaa atgctgtttg ctggctgaca   17400
cttctggagt ggaagtttat tctttttttct tttttttttt ttttttgcg gggtggggca   17460
```

```
gagttttgct cttgttgccc aggttggagt gcaatggcac gatctcggct tggagcgatc    17520
ttgggtcacc ataacctccg cctcctgggt tcaagcgatt ctcttgcctc agcctctgga    17580
gtagctgaga ttataggctc ccgctaccac gcccggctaa ttttttgtat ttttagtaga    17640
gacagggttt caccatgttg gccaggctgg tcttgaactc ctgaccttac gatccacctg    17700
cctcggcctc ccaaagtgct gggattacag gcttgagcca cggcgccggc cctttattcc    17760
tttctttggc tcaattttta ttgttaagag atagtgggaa gggcccaatt ttgaaatgat    17820
cctggaatta atgtaggagg ccttgtataa gcagttaatg tgtatttatt gagtgggtac    17880
cctgtgccaa tatgatacaa ggtgtgaagg acacatgagt tgggaaaggc atggggaaat    17940
gcacgctcac actgctggtg cgagtgtaaa aggtacagtc tctatgtagg gctatttggc    18000
agtatatact ctttgaccca gcaactccac ttttaagtat ttatcttagg gataccctca    18060
cacatttatg aaatgattta tatacaagga tattcattat agcaatattt gtaatggcaa    18120
aaagaaacaa aagtcagatg ggggactgat taaataatta tgttattaag taatactgtt    18180
tcagtacatc tgtgtaatga aataatgtcc agtcattaaa aatagtgagg caaagtctgg    18240
gtgcagtggc tcacgcctgt aatcccagca ccttgggagg ctgaagccgg aggattgctt    18300
gagaccagcc tgggcaacat agtgagaccc tgtctgtaca aaaaaaaaa aaaaaaagta    18360 aaatattagc caggcatagt ggcacatgcc tgtaatctca gctattcagg aggctgaggt    18420
gggaagattg cttgagccca ggaggttgag gctgcagtga gctgtgattc tgccactgca    18480
ctccagcctg ggcaacagaa caagacccta tcttagaaaa aaagaaaaaa aagaaaaagg    18540
gacaacttac aactctgtgc cctgatgtag aaccatctcc aaaatatatt aaatgagtgt    18600
gggatactat gcttatatgc gattgtgtgt atttaatggc ttcctaagaa aacaaaaaaa    18660
aacctgatac tagtgattgc cttggaggag ggtaactggg aaattacttt tgcaacttt    18720 aaatcttata ccatgtacac ctggtatcta ttttttaaaa gccatttca tgccctaaat    18780 gagtttagtc agaccatagt aagaaaatcc tgtaagacat acaaagtatg gggtaattac    18840
tggctttatg ggaagactga tttcaatgca aaactctccc tatgcaaggg agttgtcctg    18900
atttcaatgc taagctctct ttaggcaagt tacgttggcc tgatttgcct gttaagtcgt    18960
atggggcagg caagtctgag tgtccagagg gcagacctt aactcttagt ttcctgcctt    19020
gggagaaggc acagggctaa agtggtttcc agaacgtgtc tgttgtggtg tgaacaccaa    19080
ggagcagtgg acaagcttcc caggctcaag gtcagaaggt ctggactgga gtcctgcctc    19140
tgctacttgg tgaatatgtg atttggggca ggttgcttaa tccccgaagc ctcaacgtgt    19200
tcatctagaa atgaagatta caggctggac gcagtggctc atgcctgtaa tcccagcact    19260
ttgggaggct gaggcaggca gatcatctga ggtcaggagt cgagaccag cttggccaac    19320 atggcaaaac cccatcccta ctaaaaatac aaaaattagc tgggcatggt ggcaggtgcc    19380
tgtaatccca actactcggg aggctgaggc aggagaatca cttcaaccca ggaggtggag    19440
gttgcagtga gctgagattg tgccactgca ctccagccta ggcaacagag tgagactctg    19500
tctcaaaaaa aaaaaagact acaataccctg gcccaactcc ctcatgctac tgtagtgagg    19560
ctcaaatgag atagcaccca tgaacactcc tgtaaaccat gaagtatgca aacaccaggt    19620
gtaatagaag ctgttaggta cctgtgaggc cagcagacaa gagcaagaga tgctaattta    19680
aaaagaatta aggtgaagca aagatctttt ccctctgcca aataacttgg caagagttgt    19740
aaaattagaa aagtagaccc ttagtagttt gataatcctt tgacctctga ccctgcacaa    19800
```

```
atgatctcac cctttagacc tgttccctta tttgcaaaac aagaggggct gtctgggtga   19860
ttcctgtggt cccttccagt tgtagcgttc cgtgacagtg tggcattaac agtaattccc   19920
atcttggctg agatggatga gtcatactaa ctgaaaagtc aaaatacgag gaagaagtct   19980
ctttatgtat gagaattttc cttgagctag agactcagag cctcttgggg aggagatgag   20040
ggaaaacatt gccaccacca agaagggaga cgaaggatgt ataaagagaa tggagatgta   20100 tttactttt tttttttttt tttttttttg agacagagtc tcactctgtc cttctggctg   20160
gagtgcagtg gcacgatctt gggttactgc aatctccacc tcccaggttc acgccattct   20220
cctgcctcag cctcccaagt agctgggaca caggcgccca ccaccacgcc cagctaattt   20280
tttgtgtttt tagtagagat gggtttcac cgttagccag gatggtctcc atctcctgac   20340
ctcgtgatcc gcccgcctcg gcctcccaaa gtgctgggat tacaggcgtg tgccaccgca   20400
cccagccgag attatttact tcttgtgtgt tcttgccatc tccatagcct cctttgcttt   20460
caaatgccca cttgggctgg gccttttgaa aatagattta acccttgttt attggaagga   20520
tattcacaca gtaggccagt tatacacttt gtggcagtcg ttacctcttc tgtgaggtct   20580
ttctgtgcag atttagtggc acctcctcca tgctgcctgg gcttctactt gcttctcatc   20640
actttgtctc ataactcaga tcagagactg tgtcttactc atctttgtat ccctggcatc   20700
tgagggggtg gtatctgatg ggtagatgga ttagtgatcc acttagggta tttacactaa   20760
tcttgttgat cttgactact acctttataa ccaccaccat tctacaagtt ttaacttttt   20820 ttttttttg agacagagtt ttgctcttgt cacccaggct ggagtgcaat ggcgcgatct   20880
tggctcactg caacctctgc ctccccgggt tcaagcgatt ctcctgcctc agcctcccga   20940
gtagctggga ctacaggcac ccgccaccat gcctggctaa ttttttttgta tttttagtag   21000 agacggggtt tcaccgtgtt agccaggatg gtctcaatct cctgatcctg tgatccacct   21060
acctcagcct cctaaagtgc tgggattaca ggcgtgagcc accgcaccca gcaaggatct   21120 ttttttttt tttaaagct aagtgttta tacatataat aatattgtta ataaaatgta   21180
tctaaaattc ataccaccag cacacaaggt ctccggctag cagcagtaaa tggcatttag   21240
tacttactta gccccaagc ctggatgact gactatactg acttattatt acttttagct   21300
atttgtaggt agttacatct gaaaattgac caggcacagt ggttcatgcc tgtaatctca   21360
gcactttggg agaccaaggc aggaggatca gttgggccca agaatttgag accagcatga   21420
gtaacatagc aagaaccatc tctacaaaaa ataaaaatta accaggcatg gtgatgcatg   21480
ctacttggga ggccaaggtg ggaggatcac ttgagcctgg gaattagaag ctgcagtgag   21540
ctaggaaggt gccactgcac tccagcctgg gcaacagagc aagactctta atctctttta   21600 aaaaaaaat ctgaaaagga ccccaaggat tgaactttat ctttacattt atctttacaa   21660
atccaggatc aaaagagagg gtaaaggatc acttggggag tttagaagtg gcagaagtat   21720
ctgtagaagc cttacggtgt gaatgtgctg gattgtgtgt gcccaccctc atggggact   21780 tccttggagg atgagggtac accagcatgg gcagcaaagc tgtttgacct caaggtggag   21840
atctgagcca cctggtcagt ccatgcccag ttaatttcta tggaggtttg gtaaagtagg   21900
ttagggagtt ggatccaatg ttcctgaagt ttctgttggt aatatggcag gggtcgggtc   21960
gggtgtgggg agggttggat cattctaagg gcagtacaag acctaatccc aaaggtgaga   22020
agttcctctc tgtggaggac agcatttaga actcaataca tacatggctt gttcaaaaat   22080
ggggaagaga ttagaaaaat ttatcctaat gtttgcttgt caaaccaagc cattctctca   22140
gcaaagtagt gaaacccctta cataagtcct ttgaagccta gcagcagtat cctactcaaa   22200
```

```
cacaaaccac caaaaaaaaa acaaaaaaaa aacaaaacct ccttggggac tcagatgtga   22260
acctctcatg gaaaattcag taccatgtgc tttttgtagc aggtaggatc acctgctgtt   22320
ttggaaatta acttttttc tgacatcttt ttgaccgaac tctgcatgtg cctcttgaga   22380
aaataatcca aattcttgct ttcttcactt tccagttttg ctttatcttt gcatcatgct   22440
ctgcagttta cagacaagca taatgggtga gagttccagt aaattggctg gatcatattt   22500
cttagattga gtcatgactg aggaacttgt ttgggaacag gaagcagccc atgaaaatgg   22560
ctgcacatag taacctgcca gattgaagaa accggaccac tttctagtgg aaagataaaa   22620
gggcagaaaa atggttctat aactcaggga atggtaaatt tgtgaactag gttttaact   22680 tgttgaataa tacgtctttg tgtgtatttg gcttttttta tgctgttaaa agtctctagt   22740
tattcaagat aagggaaagg aaaacttgga ttcgtggtaa ctgttgctac ctcttaaatg   22800
tctctgctga tgtatacaac atgttgctag gccagttatt tttttaagg cactgtagtt   22860 acatagaaat aaacctggca acatttacac ttggcctcga taggctgtaa ggcccctttt   22920
gtctccagta ttctgtgttt ctgtatttta atcacctact ttacacttac tgtagcaaca   22980
caatcaagat agcaaatcag tctaataaaa ccaaaagtac tggaatgtgg gaaatagaaa   23040
gaatgaccta gaattcttgc tgagaaaaca attggtattg ctatattctt gtaatgcagt   23100
gtgagagaag ccagagaagt aaataggcag atacatatct atgaaatgta attagtcatc   23160
agcaagatgt attttaaaaa cacatctgct tggtgtcatt ttgctttatc taataaggat   23220
tacgactgca aggcagagat ttgtaaatga aggagatctc tgttgttttt gttttgtttt   23280
tgcttttgtt ttgttttaag acagggctgg agggcagtac atgatcatgg ctcactgcaa   23340
ccttcatctc ctgggctcaa gtgatcctcc cacatcagtt tcccaagtag ctgggactac   23400
agcagtgtct caccatgtct ggctaatttt taaatttttt tgtagagttg aggcctgtgt   23460
tgcccaggct ggtctcaaac tcctgggctc aagtgattct cacacctcag cctcccaaag   23520
agctgggatt acaggtgtga gccaccgtgc ctggctgtta ttttatcaat tcctcaaaat   23580
tcaagcatgc cctcaaatat ttttgcagcc tcatatagct cttaatttgg tttatattca   23640
tccagatggt aggatatgat tcatgttcca cctggttttc ttcagaaata cttagacagt   23700
gtctatggaa aaaacattg aaccagattt agcttttagg taaataatat aatcacctgg   23760
gaataatatg aagaatgaaa tgaaagaaag aaaaatataa tcaagtgtaa cttagactct   23820
gaatgctggt aactaagatt tggatgaagg aaggatctca ggggaataac attaaaataa   23880
gatttttttt aaatggaaat acatgatttt aagaaggaat aacttaagac attccaactt   23940
tatactacat gaaagtaaaa agatcaagga tcagttttct ctttggagca aggctcagtt   24000
tcgctttctg ttgagagtta gtagtgtgta taattaattt ttttttaacag tttattgatg   24060 aaatttattt ttagaaggaa atctcccacc accttcctgt cattctcagg gcaagataga   24120
gggtaggaga gggaagggag actcggggga atgggaggtg caagccttaa ttagacattt   24180
gagtgtctaa aagattactt ttcatttcaa atactttgtc tcagtttact gaatagcttt   24240
aatttaggac agggattgta ttatcttgc tttatctttt ccaatatttt ggatcatcta   24300
agcatgatag atgctggttt attcaaggca ctaaaattga cttgcaaaag acatatttaa   24360
tatggattct gtgttcaagt cctttcttct ttgtttatcc tggtacaaag atgtttgttt   24420
taaagtggta tgagttaatt gtccaacttc agatttccct aaaatgtgta acagattacc   24480
cagttggcaa atgatgatat atatttttta aacatgaata tttctgttag gccagatggt   24540
```

```
gatttaacat gaattgtcca acatttgtgt ttcttatcaa attgtcttct tttgtctaag   24600
ccaagctagc aacataattt ggaacacact caggaatcac taaaggacaa gagcaaaaaa   24660
aattcagaca ccaagtggca gacggcattt gctccatatg ccatgcaaag gctcctggcc   24720
agtgctcgca tggcccttgg gaagctttct cacccgttgt aagaaagtat ctgtgcagtg   24780
ctgtgcaacc catctacctg cttcctctc tctacccaaa ccctacttat ctaacacttt   24840
gtactgtggc cttcctccat gggggacttg cacttcctca aagccctgga tttctgtgca   24900
gaagagcagt tttagttctt ccttaggcac ttcccttttcc tcctgtccag tgtcatgttc   24960
ttgtttgtta tgggctccac ccagacgatt atttcctctt agatgatgtg tgagccttgc   25020
agagagctgg gtcatttgtg aataaatca tgtgcccagt cacacggctc cttacaggaa   25080
atggttggtg catattagct tagcacaaaa tacagtagtg agcttgtggt ccccaacagt   25140
gagtcttcag ttaacttctg ctgtttttttt tttttttttt ttaacataaa gctttgaatg   25200
tttcatacag tatcaaatct ctgcaggatt ttgcctgctg aaacagatgt gaaaatctga   25260
gtagcacaga gtatgacatt aaggccataa caataaacct attgttgctg cattctaaat   25320
ttgatcaaga tgtctgtttt tgggaatcca aaatagttgc ttcaaattta gcttttttct   25380
tttatgaagc agttttgttt tgttttgttt tgagacctct catagcaaga aaaacatta   25440 cataaacttt tttttgagac aaggtctcac tttgttaccc aggctggagt gcagtggcac   25500
gatcttggct cactgcagcc tcgacctcct gggctcaagc agtcctccca ccttagtccc   25560
ccacgtagct gggactacag gcacatgcca ccacgcccgg ctaattttg tattttagt    25620 agagacaggg tttcaccatg ttgcccaggc tggtctcgaa ctcctgagca caagcgatct   25680
gcccgcctcg gcctcccaaa gtgctaagat tataggcgtg agccaccatg cctggccaca   25740
taaatataaa cttaaaaata cacaggaaaa cctttcagaa cactttgaaa cctatttgg    25800 tcctattacg attgcactga atgtccccca gcctaatgaa gagcaattag atgtcatttg   25860
gtggcattct tggtggagac agtaagctag gccgcagga gctgcttagt ctcccagggt    25920
ccagcattgt ttcaggtaac gtgaacagga tgctcaagag ctagtctaaa taatgcttca   25980
tgtcttattt ttcctgtttg ttgataagga ttcataaaga tgtcttttc tggtcatgtc    26040 aagggaaatt caaataaaaa acattgaatt ggtttggagc tgtccattga agggtactca   26100
cagcaggaat tgagtggcaa ttgaatgtgt gtgtgtgtat gtttgtaaac atttatatta   26160
gagtgtatgc aaatgtatat gggcgtgccc actgccatca ccattacccc caccaacagt   26220
aacaaaacca ccatcaagag caatatccac taaaacttct aatttgctta ttaatttgct   26280
ttattatttg taaataattc agaatctctg agatcaaaat cctttttat tacaacatgt    26340 taatagtagt ctaattcaga cctgccctga ggaagaacca agcaatgaag ctgtccatga   26400
ttttagaagt taattggctc attctttctg accatctagg tagtcccaac attatttag    26460 gctcccccta gttaggtcca caacctcatt attatccatt ggcctggact ttggtctcgc   26520
ttatacagca agtagtagag cctatcactg tcaacatgta aacatttgca tattttacat   26580
ttatagagag atactttca cgtgcctcat ttgatccact aacatctgta tgcttgggta    26640
ggatggaata attaaacaat gtatagctaa agccatccaa acccctcaaa tattatcatc   26700
tgatgggaag gaaaggggg ggaaaggaaa ttaaatagtt atttcaattc ttggcatgat    26760
tgacactgac aattataaat tccattcaat attttcttcc agctcatgag ggttggttgt   26820
aaggatactt tgcaagtcag atttatgagc agaagatgtt tgcaacctaa attgcttcag   26880
ttgcatgaaa aagtcacaac ctttttactga ttttatcct gggatctcct taacaagaaa   26940
```

```
aaacctcagg cccaggaagt ctagggtgag gcagggatgt gtcaaagtac acttttcccc    27000
acgtacaggg acaagtattt gagtttcttt gattgacttt gcaaagagct ttgcacactt    27060
tgcacatcac ttcttgagat gggtgggaac atggactgcc tattttacag agttcaatta    27120
agatcgcagg atcatgcatt cctttcattt ttggtgctag tacctagaag atgggaacat    27180
attgaacact taataccttg cttgggcaga tagctccagt ttgcagaaag tctagacagg    27240
ataccctgct atgtatctag atttactgag aagaagcggc ccaagctaat cagaatttta    27300
aagtaggttt ctcagctggg cgtggtggct cacacctgta atcccagcac tttgggaggc    27360
cgaggcaggc agatcacttg aggtcagggg ttcgagacca gcctggccaa catggcgaaa    27420
tcctgtctct actaaaaata gaaaaattag ccgggcatgg tggcacgcac ctgtaatccc    27480
agctattcag gaggctgagg tgagagaact gcttgaaccc tggaggcgga agttgcagtg    27540
agctgagatt gtgccactgc actccagcct gggcgacaga gcgagactcc gtctcaaaaa    27600
aaaataaaat aaagtaggtt tctctatacc tttgaatttt ctgtctccca tgataacctt    27660
tgggtaaaca tgtccatcag aatggaaaca aatcattttt taaaatagaa attattctca    27720
tacctatttt agtgggaatc cccctgagaa gatagccatg tatagtcgac tgaatgctct    27780
gtggttgcta ttttgttgct cttggccagg aaactgatct aggtgaccta cagacttaat    27840
ctgacctgca gactggccgc ttcatactac caagattcca aagccaagtg tatatacagt    27900
cggcccatgc agcctctggt tccatgatgc aaccaatggc agattggttc aaaaatattt    27960
ggaaaaaggc caagcacagt ggagtggttc atgcctgtaa tcctagcact ttgggaagct    28020
gaggcaggaa aatcaatgga gcccgggaat tcaagaccag cctgggcaaa atggcaagac    28080
gccatctcta caaaaagtaa ttagctgggc ttggtggcat gtgcctgtag tcccagctac    28140
ttgggaggct gaggtgggag gatcacttga gcccaggtga aggctgcagt gagccatgat    28200
tgcatcacca cactccagcc tgggtgacag agtgagaccc tatctcaaaa tgagtaaata    28260
aataataaaa tttcaaaagg aaaaaagtgg aaaaaaaacc cgaaaaaata acaatacaca    28320
cataaaatac agtataacaa ctatttacac agcatttaca ctttactagg tattgtaagt    28380
aatccaggga tgagttaaag tatataaagg gatatgcata ggttatttgc agcaaatgcc    28440
atgccatttt ataatagtgt aggctcatgg ctaataaagc atgaacccga ctgaagctgc    28500
ctgggtatgt gtctttgttc agccactttc tggtagtatc ttttttctta acctcagtat    28560
tcttatactg tataacagga atgttttctc tgtataaggc tgttttgagg aatagtttct    28620
atatgtaaag tacttagaac agtgcatagc atataggaag cccttaatag atactggctt    28680
aaagataatt aggtatgtcc tagtgaggta tacctaacta caagtgctac tttaactatg    28740
cctactttgt gtgctttaca atatatattg ttcaaggcta gaataatgag ccccatgagc    28800
agggtttcat agcatttaag attccaacgc caaccttcaa tcatggacac aggtggcctg    28860
tgccatctag ctagctgcgc tgcctccagg ctggtggcc tgctcctctg ttggataaaa    28920
atagcctgac tcctcactga acaaccacc atgttatttg cgtccttggg aagctgaaag    28980
taatagaact ctaagtctgg cgttgccagc tgtcagcaga atgaaatgca aagtgtgacg    29040
tgtctacact gtacccactg gccttcaagt cccaactccc gttcccccat cttgattttt    29100
ttccattctc aaattaatta tttcccctat aggtgatttg tggaatggaa acagatttag    29160
atttcctacc tatttagatt tttccaaaga ctaaaattac aaatcagaaa aactgctatt    29220
gacacatttt tggttaggaa aatctggatg tggttcctat gcctagccta gtcatataaa    29280
```

```
ttctctcccc atgtatctttt ttgtgtgtgt gaaacagggt cttgtcaccc aagctggagt    29340
gcagtggtac aatcacagct caccatggcc ttgacttcct gggctcaagc aatcctctca    29400
cttcagtctc cctaatagtt gggactacag gctcgtatca ccacgtgcaa ctaatttgtt    29460
ttgattttgg gtagaaacag gtgtcactat ggtgcccagg ctagtaactc ctgtgctcca    29520
gcaatcctcc tgccttggcc tcccaaactc ctgggattac aggcctgagt caccaagctc    29580
agcctctcct catcaaaacc attccctctt tgtaagattc ttcctatgtc ttaaaactta    29640 ataccttta tccttccctg gagccatagt tttatttatt tatttattta tttatgagac    29700
agggtctcac tttgttgccc gggctggagt gcagtgacac gatcatagct cactgctgcc    29760
atgacctcct ggactgaagt gatcctccta cctcagcctc ctgagtagct gggaccacag    29820
gtgtgcgcca ccacaccagt tgttgttgtt gttgtttgtt tttgttttgg tagaaacagg    29880
gtctctccat gttgcccagg ctggtcgcga actcctgggc tcaagcaatc cacctgcctc    29940
agcctcccaa agtgctgggc ttgtaggcgt gagccaccgc acctgtccct gtctgctttt    30000
attttatttt ttttgagat ggagtcttgc tctgttgccc aggctggagt gcagtggtgc    30060
gatctcagct gactgcaacc tctgcctccc aggttcaagc cgattctcct gcctcagcct    30120
cctgagtagc tgggattaca ggcacgtacc accacacccg gctgatttt gtatttttag    30180 tagagacgtg gtttcaccat gttggccagg ctgatctcga actccagacc tcaggtgatc    30240
cacccacctt ggcctcccaa agtgctggga ttacaggcat ataggtaagc cacagagata    30300
agagtagcaa gcagtgatgg ggagaagata atctagtgta ggaaagatgg aaagaatggt    30360
gatatttcac aactgctaga ttgacacttt aacttgagag ttatccctct ataaactgga    30420
tatttgctga gcaaagtttta aagaaaactc catgtattca gtaatgtttt ccagacccca    30480
cttctcttat ataagccagt ggcttagagt gcttgctcta atttctatat tccattaaac    30540
aagggtggga tttcttctca ttcaaaccat ttgtgacttt gccctttagt gacctctacc    30600
atcaccctat cattaatgat ccaagtgatt agaatggatg gctatgtgtt tgtaggttgt    30660
ttgttgtctt taatgaatag attcattgaa tggaattaac tgtgctcttc tagaacattg    30720
gatctgtgtt ctcatttaga ttgtatttgt aatctcccca cttcccacca tcaacagtgg    30780
cataatgtga attaatttat gtggtatctg tcatttaaaa aacatgagct ctctccttcc    30840
tttttttgtc ttaaacatag gacatggatt tgattgacat actttggagg caagatatag    30900
atcttggagt aagtcgagaa gtatttgact tcagtcagcg acggaaagag tatgagctgg    30960
aaaaacagaa aaacttgaa aaggaaagac aagaacaact ccaaaaggag caagagaaag    31020 ccttttttcgc tcagttacaa ctagatgaag agacaggtga atttctccca attcagccag    31080
cccagcacat ccagtcagaa accagtggat ctgccaacta ctcccaggta cagagtactc    31140
agttcttggg aaagttatgg caggtttaag gaaacactga gcaaggaatt aaaatatctg    31200
gatttgagtt ccagctttgc ctttcttta cttaaccttg tcaaatctac tttccaacct    31260
cagcctcctg atgagttcag tacctaacct gagttcagta cccaacctat tgatcttaac    31320
agtgttattg tgaggattgg gaagacttaa gttacaccaa agagttttgt aaagtataga    31380
aacatcctgt aaggatcaag tagcagcaac agaagtagta gcaggagaac caagtagcag    31440
ggattactgg cgttactgtg tgtggcaagc actgttttaa gaacatatac tgactgattt    31500
aattaacaca actatattaa ttagttacca ttatccctgt tttatctacg atgagcaact    31560
gaagctcaca aaggttaaat aatttgccca gatcactcag aaaattggag gagctaagat    31620
ctgaacccat gtggtctagt tcaaattgtg catcaaagtg atctctgaaa taagataaat    31680
```

```
atttacttaa cttgattata aatattttat gaacatcaat tattgaatat ttagcttggc    31740
aatggaatat ttaaccattt ttgttttcct ttgtgtcatt cccttttatc aggttgccca    31800
cattcccaaa tcagatgctt tgtactttga tgactgcatg cagcttttgg cgcagacatt    31860
cccgtttgta gatgacaatg aggtgaggta taaaataacc tggttaatag aaaaactcca    31920
tcataactat aaaataacaa tctattctat gtaagtcccg tcaatgaatc tccatttaaa    31980
agaataaaaa cattttaggg aggaaatttt ttaaccaagg aaatactctt gtcaaggaaa    32040
ccttagccta taaataactt tacaattaag aaaaaaaaaa acccttcaca caatacaaaa    32100
ccaaaaccat tgactattgc atagccagaa acatggacag cataaccatg gaaacaaata    32160
acccatttgc tgcaagtatc taagaggttt ggtgagtaaa gagccagctg gcaataaac     32220 gaagacttgt tcagttaaca attttaataa atctgtttta tctagtacca ctgtgctaga    32280
tattatataa actaaatcct aaagattgta cttacgcatt ttaaagttta ctttcaaatg    32340
cttaagctga aacagaccag caaattataa atttgagtca gtggggtagg aaaaaaagat    32400
ttgttattta caaacggggt catgactggt tagtaagtag agagacacag aactgcagct    32460
gattccattt tgttttgtag tggtgcctta gagcttactc atccctgtt ggtggaagac     32520 tcataaatca atgccttatc aatttaggt ttcttcggct acgtttcagt cacttgttcc     32580
tgatattccc ggtcacatcg agagcccagt cttcattgct actaatcagg ctcagtcacc    32640
tgaaacttct gttgctcagg tagcccctgt tgatttagac ggtatgcaac aggacattga    32700
gcaagtttgg gaggagctat tatccattcc tgagttacag gtaactaaaa tagaatgtaa    32760
tactggagat ttttttttata ttcagtgcct ttagtcattc tgattatta tataccacct    32820 atttatagga aggattggag ggtgctatta acttagtcat gagtactgcc catgctagtt    32880
aaattggttg gacatcttga ggatagaatg ttataaacct gacgtctgat ctgggaactc    32940
tgaaaataat acataacgct taggcgtaaa tatgtattgg aaatgagaat tatctctgaa    33000
ttatagataa taaattatag agataagcct gaagataatg tgggtaggga gtttatctaa    33060
atttatcacg tattatcatg gattaacttt gatttatata gtataaactt ccttctcatg    33120
cagtgtctta atattgaaaa tgacaagctg gttgagacta ccatggttcc aagtccagaa    33180
gccaaactga cagaagttga caattatcat ttttactcat ctataccctc aatggaaaaa    33240
gaagtaggta actgtagtcc acattttctt aatgcttttg aggattcctt cagcagcatc    33300
ctctccacag aagaccccaa ccagttgaca gtgaactcat taaattcaga tgccacagtc    33360
aacacagatt ttggtgatga attttattct gctttcatag ctgagcccag tatcagcaac    33420
agcatgccct cacctgctac tttaagccat tcactctctg aacttctaaa tgggcccatt    33480
gatgtttctg atctatcact ttgcaaagct ttcaaccaaa accaccctga agcacagca     33540 gaattcaatg attctgactc cggcatttca ctaaacacaa gtcccagtgt ggcatcacca    33600
gaacactcag tggaatcttc cagctatgga gacacactac ttggcctcag tgattctgaa    33660
gtggaagagc tagatagtgc ccctggaagt gtcaaacaga atggtcctaa aacaccagta    33720
cattcttctg gggatatggt acaacccttg tcaccatctc aggggcagag cactcacgtg    33780
catgatgccc aatgtgagaa cacaccagag aaagaattgc ctgtaagtcc tggtcatcgg    33840
aaaaccccat tcacaaaaga caaacattca agccgcttgg aggctcatct cacaagagat    33900
gaacttaggg caaagctct ccatatccca ttccctgtag aaaaaatcat taacctcccct    33960 gttgttgact tcaacgaaat gatgtccaaa gagcagttca atgaagctca acttgcatta    34020
```

| | |
|---|---:|
| attcgggata tacgtaggag gggtaagaat aaagtggctg ctcagaattg cagaaaaga | 34080 |
| aaactggaaa atatagtaga actagagcaa gatttagatc atttgaaaga tgaaaaagaa | 34140 |
| aaattgctca agaaaaagg agaaaatgac aaaagccttc acctactgaa aaacaactc | 34200 |
| agcaccttat atctcgaagt tttcagcatg ctacgtgatg aagatggaaa accttattct | 34260 |
| cctagtgaat actccctgca gcaaacaaga gatggcaatg ttttccttgt tcccaaaagt | 34320 |
| aagaagccag atgttaagaa aaactagatt taggaggatt tgaccttttc tgagctagtt | 34380 |
| tttttgtact attatactaa aagctcctac tgtgatgtga aatgctcata ctttataagt | 34440 |
| aattctatgc aaaatcatag ccaaaactag tatagaaaat aatacgaaac tttaaaaagc | 34500 |
| attggagtgt cagtatgttg aatcagtagt ttcactttaa ctgtaaacaa tttcttagga | 34560 |
| caccatttgg gctagtttct gtgtaagtgt aaatactaca aaaacttatt tatactgttc | 34620 |
| ttatgtcatt tgttatattc atagatttat atgatgatat gacatctggc taaaagaaa | 34680 |
| ttattgcaaa actaaccact atgtactttt ttataaatac tgtatggaca aaaaatggca | 34740 |
| tttttatat taaattgttt agctctggca aaaaaaaaaa attttaagag ctggtactaa | 34800 |
| taaaggatta ttatgactgt taaattatt | 34829 |

<210> SEQ ID NO 4
<211> LENGTH: 30584
<212> TYPE: DNA
<213> ORGANISM: Homo sapiens

<400> SEQUENCE: 4

| | |
|---|---:|
| ctctgctctg gacttgggag gctccgttgc ctgctcccgg agggagacgc gctgccgagg | 60 |
| agaacccagc gggtaatgaa tccccgcgc ttctttgccc aggccttccc caaacctccc | 120 |
| cccggtctgc gcgggttctc ctattgggct gtggtgaaga caaggtgcgg cgactgcagc | 180 |
| tccccaggtc tgggcgctgc cgggagagag tctttcccgc tggggagatt tagtttgttg | 240 |
| actcaggagc acctccaacg acagctagtg gcagaggacc cggagctgg gaggttcgga | 300 |
| acgcggggcg agctggggag gagggagagg cgccgaccca gcgcagccta catcttagca | 360 |
| aaccaaacct ggcaacattt ccccacggtt caggagcacg aaggacttaa gggaaaacga | 420 |
| cgaaatcggg gctcccgagg atgaagttaa atgggttgtg gcctggggac aaatagggcc | 480 |
| aatgtccagt ctattacaag aggctttgtt ccagaggctt gcctataagc ccctggcttg | 540 |
| gaacgtcagt cttcaaactg taacaacagg ggcaggctac tagggtagcc cacaaagccc | 600 |
| tgtatccccc atacagtgac taactagagc cctagttggt catatccgca gtggctgaga | 660 |
| ctgcggtgtg attccgtttc cctcttgcat gtgtcccggg agcccgagtt gtcgaagccc | 720 |
| aaattcaggc tcaggaacct gatgtgctgt tgatgccaaa cactgacaca cagatgcttg | 780 |
| gagacagagg aagatttatt ccatttggcc aaagcgagaa ggcaagaggt caagatctct | 840 |
| caaatccacc ctaacaaaaa gaagtagtgg ggagttttta tgagaccagg aagtaaggga | 900 |
| gggggaattt cagggaacct cggggaaaag tctttcttcg tctcagatta catcttgaac | 960 |
| caccagactt ctgggcgtca gcagctggtc acaatgccct taaaggcatt cattccttct | 1020 |
| gcaaaatttt tttcttgact ctgaagctat atcctcctgc ttgacaaaga aacggtgcat | 1080 |
| cagcagttta taattatatt gctagaaaaa ggaatattgg gcaaaaagtg ggtagttaac | 1140 |
| atatgcaaat aagcaagggc ctcatcggaa ttttcatggt ttcatcacta aaaatgttgg | 1200 |
| ggtgctgaaa tcttgagggg ctcggttgca ccagaagggg atcctttgtc actagtgcag | 1260 |
| gcaggaaggg atgcttgagg gaggatgggg ggaacttttc aatagttcct cccctcccct | 1320 |

```
accaatagcg ggtgggaggg cgttggttta gagccaagcc tctaggagaa gatgagagca   1380
atggctaaag tttgtctggc ctcgccctat gagaagggggg cggaggctgt gcctgccttt   1440
gtgggggaaa aagaagccga ttcctaatct gtctgtctca tgggaggtga gagttcctgt   1500
ggcaggataa cagacaagca attcagtgtg ataacatcct gtgtcagaag tattcattta   1560
aatgtcacaa gaggccgggc gccgtggctt atgcctgtaa tctcagcact ttgggaggct   1620
gaggctggtg gatcacgtga ggtgggcgga tcacttgagg tcaggagttc gagacagcct   1680
ggccaacatg gtgaaacccc atctgtacaa aaaatgcaaa aattagctgg atgtgatgac   1740
acatgcctgt aattccagct actcggagcc tgaggcagga gaattgcttg aaccaccccc   1800 tcccccacc ataaaaaaag tcacaagaat taaactcttt tgtttaagaa aataagcagt   1860
tttattattt ccatgtaaga ggaagaagag gaaaatgctg tgatccactc ctggcctgat   1920
tatgaaaatt cacacgtgtt tatagcagcc ccactttaac catgggatat gtcccaagac   1980
cctaagttga tgcctaaaac cagatgcctg aaaccatggg tagcaccaaa ccctatatct   2040
aatgtgtttt ttccctatac tttcactgtt tcacttaaag aaagcactta agaaaggct   2100 tttcttttggc atatctgaat tgccagcatc actactctgg agatttgggg ccattaaata   2160
aaataagagt tacttgaaca taagcagtat tagagttgat ctggtaagta agaaggctac   2220
caagtgacta agggctagta gcatatacgg ggtgagtaca ccagacaaag gaatgattca   2280
tgtcctgggg tgagagggag tggatggcat gagatttcat caggctactc agaatgaaac   2340
ttgaaactta taaattattt atttctggaa ttttcattt aatattttg gactagagct   2400 gactgtggta actaaagcat ggaaaaccac cagataaggg aggactacta tatactatca   2460
gaaaatagaa atcatttcca gtattattgt tatggcaaat tgaatcatat gatatacact   2520
cttttatgtc tggcttctgt cactcagcat cattgttttc agattcatct atgtcattgt   2580
gggtaccaat agttctttcc tttttattac ggttgagtag tcttctatta tatggataat   2640
caatattggc ttcttcattc atctactgat gggcatttgg attgtttcca gtctatgtct   2700
ttcacaaata aaaatgttat gaacattcat gcacaagtct ttgtatggac atatgctttt   2760 ttttttttttt cctcttgggt aaatactttg gtgtggaatg gctgggtcat atggcaagcg   2820
tacgcagaac ttcttaagaa actgccaaat tcttttccaa aatggtcgta ccccttata   2880 tccctacaag gagtatatga cgatgcccat tccttcacat cttcaccaac aactagcatg   2940
gttagtcatt ttagccattc taatagatgt gtagtggtat ctcactgaag ttttaatagg   3000
catttcccta acgactaatg atgttgagca taattcaatg tgcttatttg tatccatata   3060
ttttctttgg taaattgtct attcaagtat tttattcatt tttaaattgg gttttttttat   3120 cattactttt tgagtgttct atatataatc tacttacaag ttctttatca gttatgtaat   3180
ttgcaaatac cttcttccag tcagaggttt atattttctt tttttcttaa acttttactt   3240
taagttcagg agtacttgtg cctgacgtgc aggtttgtta catagataaa tgtgttgcca   3300
tggtggtttg ctgcacagat catcccatca cctaggtatt aagcccagca gccattagca   3360
ccattctgat gctctcgctc ctcctgttgc cccctcctct gacaggctgg ggcttatatt   3420
ttcattctct taatagtgtc tttcagaagg agaagttctt aaagtccaat atatcattta   3480
aaaaaattta ttgtgcatct aggccaggtg cagtggctca tgcctgtaaa cccagcactt   3540
tgggaggccg aggcagggag atcacttgag gtcaggagtt tgagaccagc ctggtcaaca   3600
tggtgaaatg ccatctctac taaaattaca aaatttaccc aggcgtggtg gtgggcacct   3660
```

```
gtaatcccag ctactagaga ggctgaggca ggagaatcgc ttgaacccaa ggggtggagg    3720
ttccagtgac cgaaatagca ccactgcact ccagcctggg cagcagaggg agactccatc    3780
tcagaaaaaa aaaaaaaaat tattttgttc atctaatatc atctgtaaga aatgtttgcc    3840
taacccaagg caaaaatatt ttctcttata tttttctcta gaaattttat ggttgacagg    3900
ctaaatatac atacaaactc tggccaggac atatgcaaaa atagaactct gacccagaac    3960
tgctgcagta accagcctgg gaagccaaac acaacttctg cagcagttga ctggtagtgg    4020
tcaggacctt gtcaataact gacagcatcc ttaattttg ctcctgattc caatttagga     4080
ccagtcagag aaagccaaat atgttcccca aactaatcat acaggatgtt catttctagt    4140
tagcctgctt ccaacttccc tacgacaaca cccttgaatc atatcatacc tgagcattcc    4200 cttttttgtca ctatcaatct ttcccctgcc tgtctatgag gctttgacaa atgtgagtga    4260
tgatggcggc tgactccctc gttatagtga gctctgaata acagcctct gcttgttctc     4320 atccaggcag acttcattaa tgtctttagt ttccttgcag gttccaccaa ggtaccatct    4380
gcccactgtg tggactccca ttttcaaaca ggatggctgc tacagaggca ccttgcacct    4440
tgcagagagt ggtttgttga gtttgcactg ataggataag tcagcactga ctgaatgtct    4500
cttttttttg agttcctcag ctactgattc tcatttgata cccgggtttt gttattggtt    4560
cccatttatt tggcaccccta ggtggaatca ggccattctc tttcacctct tttggctctc    4620 tttttgtgt gtttgtgttg tgctgtttaa aagcggtttg tccgaagaag gagaatgaca     4680
gggtcagaca taggcatagg tcctacaagc ctgttcaagc ttgcttcaca gtccagtgag    4740
tttgtggttc tccctgaacc catgtccatg tggacaaact tgttgtggg tcaccaataa     4800 aaccagctca ggttctcctt ccatcttgcg ttttttgtcct gagagcttca ctttggtcca    4860 cgggagtgc tttctctggt tttctgccta ctgaggggca cagattgtct ggtctgtgtt     4920
aggaggtgcc caactgtacg gttggggacc tgagacacaa agtgcacaag aattatactc    4980
ctactgatgg tcaacagctc tcatggggtc ttctaagtct aaataccctc tcatctagg     5040 agaaactgct tcttatttgt acaacactag ctcatgcacc taccttccta ccttcctaat    5100
ggcataactc caaggatgat ctgggccttt actggctatt tgggggtaca tttgacttga    5160
acaaaattgt tcatttgaca tgcaccttag aaaagtagga ataagatttc tcaggatgaa    5220
tggggctgcc gttttttgtt ggtaggcaga ggcctccaaa tgaaattctg atcaaaaatt    5280
gcttcattaa aagattcttt gcccaaaacc aatgggaaat ttgacacact taaacaacaa    5340
caaactagac tcatttccct agtaaatgct tcttttcctt gtcttccaga tgcctccgtg    5400
tatccagctc tctcttttcc cccttatcct tctattaggt tggtgcaaga gtaattgcaa    5460
tttttgccat gactttcaat aatctctctc ctatacttca gtcaactgct cacttctctt    5520 ccccctttc agacccccac cctttgccca ataactctcc taaactccaa aattccagtt    5580
gcctctgaat atccatccct ctctttaagc caggtatgca gacatctgta gaatttaaac    5640
cttggatcca agctgaatta agagttatac ttaaaggttt ccctaaaccc agcaagacta    5700
gcaaaaattc acaaaagaat ttagaattct tctaggtaca tatgacccaa ggttacctaa    5760
cctctatcaa cttgtacaca tgttggtcag aatctcaggt gctaaatcct ggagggcaaa    5820
agctgattgg acagactcag aaagggaccc acagtatccc tctttccata gtaaatccga    5880
gggttttaaa aaaaggatc caaaagtaa ggcaaagtct cctaaaagcc atacccaaat     5940
catttctaat aaaaatccat tggaccatgc aaacaaaaaa ataaaactgt tggacttttt    6000
caggatagac taggaaatac cttccaacac atcagttaaa gaaggtggta aaaagcagcc    6060
```

```
ctttcatctc attttgtcag tggagttaaa catgaaattg gagacttaat tctaaaacag    6120
aaattggaat ggaaaacaac cccttatct gaattgtaac accaagcaga acattttgaa     6180
agagctttag aactaaaatg agacaggact caaaataaac ttgtggccca cttcccaatc    6240
aaccacctat tgacaaggac actacagata ttgtaaacag aaccaagaca aataaaaatc    6300
catcagttca gatcaatgag ggtgctcaga ggaaggagaa actacccaat agtctgcctt    6360
tccctaaaca ctcaaggtga tttaactata aatacaggtg gtcaacttca tcaatttctg    6420
gtaaacatgg tactactctt tctatgttaa acactgtccc ttttgctcaa tctcttcctc    6480
tgagtaaaca taccacacag gtggtaggta tttcaagtaa cccacatata agccacatat    6540
ttattccatc tcccagccct taactgtagc ccttggtccc tgactgaaaa acattccttc    6600
ctcctctttg atatcatgcc tatgagttta atagagactt aatttgcaaa tggaactgta    6660
atatgtattg atgttccaga gacttctcta ttcataatca agttgcacct gctatgaata    6720
cacctttgct ttctctatta tatttgatgc atactccaaa taaatatctt gacaccaaac    6780
ctgacagtgt aagggctaa aaattccact cacataggac gaataattgg agaagcaaaa     6840
taataagcag aacttactaa gttcagacag atcctgtcaa accattaccc aaacttcccc    6900
aatatccata gaagtcagac gcaaaggaat ggctcgaacc tacagttgaa ggccttatat    6960
gcaaaggtcc tctcctatcc cctagtaaca ctcctgtccc gccagcaaag aaaccaagtg    7020
gatgaagata ttgatttaag acttcagaac catcaacaaa attgtcattt ctttttcccc    7080
agtagtgcct aacccacaca ccatctgtca ttaattctac ttgaagtcac ttgctttact    7140
gtagtagaaa ttttctctgc cttttcagt gcacctttag acaaagacag tcaatacttt     7200
tctgcctttg ccttgggaag acaatggta taactggaca gtcatactcc agagattcat     7260
tgaagcccct gttttgtcc agatgctcaa gtaagagtta aaagatggct gggcgcggtg     7320
gctcacgcct gtaatcccag cactttggga ggccgaggcg ggcggatcac gaggtcagat    7380
caagaccatc ctggctaaaa cggtgaaacc cggtctctac taaaaaaaaa tatcaaaaat    7440
tagccaggcg tggtggcggg cgcctgtagt cccagctact cgggaggctg aggcaggaga    7500
atggcgtgaa cccgggaggc ggagcttgca gtgagccgag gtcgcgccac tgcactccag    7560
cctgggcgac agagcaagac tcatctcaaa aaaaaaaaa aagagttaaa agacataaat     7620
ttcccttgtg accttgtgat tcagttctga tacaatataa aatgatctc ctactttgtt     7680 cagagaacaa ggaagcctgt taaaaggatt ccattttctt gctctcagcc ttagtagaga    7740
agggacataa aattttttaag gctaaattac aattttacca aaacacaatt cattatttga    7800
agtaaacctc tctaaggagg gataaatatt ctctcctgat aaagattatc cgaagttatt    7860
gtaaatccct cacaaaatga cagatgagag gatttctagg ttaactggat attgcaaaca    7920
ataggtgcca aagttttctg aaattggagc acctctttat ggattgactg tcttcagtga    7980
gggattctct cctttgaaag tccaaacata aagacctcct ggaacctgaa atcagttctt    8040
caacagcctc cttcccaaag caccccaact gtagaaagcc attttgtcta tttgtgcgag    8100
agcgatgtag agaagccctt gggccttcaa cttcatggaa accatgaaaa ccccattatt    8160
tgctgtagcc tcactcttga cctgtttaaa aggcttattt ctattggttt agggcattag    8220
ctgtcactgc aaaacttgat gatgcttctg ccaaactagc tctaggctca ttccccgcct    8280
gacctcatgg tttctcatgc aacacaaaca ttactaattt ggggttttt tttgtttgtt   8340 tttttgtttt ttgagacgga gtctcgctct gtcacccagg ctggagtgca gtggcgcgat    8400
```

```
ctcggctcac tgcaagctcc gcctcccggg ttcacgccat tctcctgcct caacctcccg   8460
agtagctggg actacaggca cccgccacca cgccaggtta attttttgta tttttagtag   8520
agacggggtt tcaccgtgtt agccaggatg gtctcaatct ctgacctcgt gatctgccag   8580
cctcggcctc ccaaagtgct gggattacag gcatgagcca tggcgcccgg acttttttt   8640 tttttttttt tttttttta agacagagt cttgttctgt cgcccacgct ggagtgcaat   8700
ggcatgattt cggctcactg caacttctgc ctcctaggtt caagcgattc tcctgcctca   8760
acctcccgag tagctgggat tacaggcaca caccaccacg ccctgctaat ttttgtaatt   8820
ttagtagaaa cagggtttca ccatgttggc caggctggtc tcaaactcct gcccccaggt   8880
gatccaccca tgaaaaaatc tggttgaatc tttactctca taatctctgg tgctctcaaa   8940
atggccactt gctggcacca aattatttaa aatggatatt agctaaattt ctccatgaaa   9000
ttactcatta taatatagac aaaattggtca ctatcttaaa tccacatccg tgggaaaact   9060
aaaaagacag ctgagcggtg gggcatggtg gctcatacct gtaatcccag cactttaaga   9120
ggctgaggca ggaggattgc ttgaggttat gagtttgaga ccagcctagg caatcttgta   9180
agaccctatc tgtacaaaaa atttaaaaaa ttagctgtgc attgtggcgc gttcttgtag   9240
tcctagctac ttgggaggct aaggcaggag gatagcttga gcctaagagt tcaaggctat   9300
agtgagccat gactgcactc cagcctgggt gacagagtga aaagccctgt ctctaaaaaa   9360
acaaaaacca aaaggacag ctgaggatat tttcaggtta tgtgtcgcct gtcaacaaca   9420
taatcctgga aaattctaa tgtcatcttt tgttcctcta tagataatgt gcctttttcc   9480
tctggatgct tttaagattt ttttctgtat cactggtttt gaacaattta attatgatgt   9540
tcctcagtat tttttttttt cacatttctt gtgcttaagg tttgtgtaac atcttagatt   9600
ttagatcttg attttttcta gtgttcatca aattttcttc aaaaatgttt tagttgtttc   9660
agacaggaga gtagcctagt ccctagtact ttattctgac tggaagtgaa agtctcatga   9720
atgtagtttt gaaaatcata gttccttaga cacagtaagg aaaccaatgg cctcagcctc   9780
tcccacttct gcttgccagg agcctcttgt ctctcgggct ttttcttctg gcacgtgttt   9840
ctgtatttct aaacagcatg cttatttct ccttctccc tcccacccc tctcatttta   9900 gatattgtct tagtcaattt gggctgctgt aacaaaatac catggactgg gtggctttta   9960
aacaacaaaa atttattgca cacaattttg gtggctggga agtccaaggt gctgagagat  10020
ttggtatctg agagggccc tcatagatgg tgccttctca ctgggtcctc gcatggtagc  10080
gggggtgtat atgctcccctt ggacctcttt cataagggca ctaatctcac ttatgagggt  10140
acatcatcat gacctaatca ccttccaatg gccctatctc ctaataccag cacctttagg  10200
gttaggattt gcacaatgaa ctttagggag ttgcaaacat tcagaccata aaagatactg  10260
tttatttctg gaagatgact gtatagcact ctctctctct ctctctttta aatctttgga  10320
gacagggtct ccctctgttg cccaggctgg agtgcagtgg tatgatcttg gctcactgca  10380
gcctcaatcc actgggctca ggagatcctc tacctcagc ttcccaagta ggtaggacta  10440
caggtgcatg ccaccatgct tggtgttttg gttttttgaag agataagaac tcgttatccc  10500
attatgttgc ccaggctggt cttaagctcc tggcctcaag caatcctccc accttggcct  10560
cccaaaatgg gggaattaca ggtgtgagcc gctgtgcctg gcctgagtat agctaacagt  10620
tttttttttt tttttttttt ttttgagatg gagtctcact ctgtcaccca ggctggagtg  10680
cagtggcatg atctcagctc actgcaatct ccagctcctg ggtcaagtg attcttgtgc  10740 ctcagcctcc tgagtagctg agactacagc cgcatgccac cttgcctggc taattttgt  10800
```

```
attttttcgta gagatgggat ttcactgtgt tggccaggct ggtcttgaac tcctaacctc   10860
aggtgatccg cccaccttgt cttcccaaag tgctgggatt acaagcatga gccactgtgc   10920
ctggccaaca cttcttatcc tatgccttcc ttctccacat cctgccaata caactatatc   10980
ttatatcatc attttttatc agaacaatat tcggagttta tattatcatg actaggactt   11040
tatttacaac ggtgccaaat aatgccttat ggttatcttt tatttactat actactttt   11100 attttaactt agcattattg tcttatattt gtatttgtct gtcttcctaa gtgcctatga   11160
ccaattcatc ccctactctc caccctctca gtttactaag tgatctgtca attgcatggt   11220
cttaggctct gtccaccgaa gcctgctgct ctgttgtgca gttttgcctg tgatctgtag   11280
gcctgctctg cagctgttat tcccagacct cccttcacaa acatccaggg gattttaaa   11340 cttcctttcc ttgttgaatc tcttgtttcc tgcatccact tttttgaggg aagaaatgca   11400
gggggcaggg caaagacagt gtccagagag catgaaatct gaaatctcag ttcacagtgc   11460
caactcttac gacacagggt tctgtaatca tgcatgagtc actgttttc ttcctacttc   11520 agagaacttc aaattttgcc agcaatgccc agcatccatt actgcaggca ttctattttg   11580
gtgtcatcaa cttccctgct caagttttca gtgcacttgg cattccttct gcgtacatgt   11640
tgaggtttaa atttctggat ttcggccggg cgtggtggct cacgcctgta atcccagcaa   11700
tttgggaggc tgaagcgggt ggatcacctg aggtcaggag ttcgagacca gcctggctaa   11760
catggcgaaa ccctgtctct actaaaaata caaaaattag ctgggcatgg tggcttgtgc   11820
ctgtagtccc agctactcag aaggctgagg aaggagaatc acttgaaccc aggaggcaga   11880
ggttgcagtg agctgagatc acaccactgc actacagcct gggcaataga gcgaggctct   11940
gtctcaaaaa aatcaaaata aataaataaa taaatttctg gattttaaaa aactcactat   12000
tgtttttcaa taatctatga ggggtgaagg aggtacagac atctttcttg ggattcttaa   12060
gttagaatct cctgttattc ttctaattag aaaaaggatt aatgatgtta aaaaagacaa   12120
atcttattgt taatggctct gcaaaccaac aacacaaaaa tatttagaga aaagtgctga   12180
aggaaatgca ttagaatgct aaatctttaa atggtgaatc tataagtgtt cttttctttt   12240
aattctgcct ttggtttttc tttctttgac acattgagca catattactt ttactgctgg   12300
gaaaaatgta agttgaaata aaaacaaacat agaaacact gaatctgctt ttagaaaatg   12360
actaccatga tatgtgtgtg tatgcgtgcg cacatgtgca tacgcatggg tgttttagcg   12420
gaatctaatc taatctgtgt gtctctcaga gttgggaggt agagccttag ggctttaact   12480
agagatgaaa agacatacat ggaacaatgg atggagtcct gcagggaacc attgtctgcc   12540
tgagcagaaa gcttgtactt gtataacagt gcctgggaaa aaaatgaaa actcatttca   12600 ttttgggata attttattgt aaagtatacc acacatacaa cagagaataa aactttatta   12660
catagttaaa aaatatatta aataaacaca catgtattca ctccagatta agaaatacat   12720
ttctagaagc taagaagctt cctgtatatt tctcccctat ttctctgtct ccctaattcc   12780
accctcttcc tccccaaaca gaggtagcca ctattttgaa tgttctatta tttccttact   12840
tttctttatg atattactac ctatatatgt ctccctaaat aacacattat ttagttttac   12900
ctgtttttga acttcatata aatggaatca taatagatgt attctgtggt ttgtgtatttt   12960 tttacaacat tatattctta gagttcattc aaaatagtgc atgtaggctg ggcgcggtgg   13020
cttacgcctg taatgccagt atattgggag gccaaggcgg gcagatcacc ggaggtcagg   13080
agttcaagac cagcctggca acatggtgaa accctgtctc tactaaaaaa tacaaaaatt   13140
```

```
agccgggaat ggtggcaggc acctgtagtc ccagatcctc gggaggctga ggcaggagaa    13200
tcgcttgaac ctgggaggca gagtttacac tgagccgaga tcacaccact gcactccagc    13260
ctgggcaaca agaagtagac tccatctcaa aaaacaaaac aaaatagtgc atgtaatagt    13320
gaaagtggat gtcattttcc atattgagaa tgactttatt actgtgtatt tccaattttt    13380
tgctattttg aacagcaatc ctttgaaaat tcttgttcat ctctccagga tatctgcttt    13440
tttttttctg ttttaatctc acaaaacact accagtttgg ttcttttaca cctgtttcag    13500
agtatatgca agtaggttaa aacaattttc ctaaagacac aaagctggca aatactggga    13560
gtttgaactc agggtttcct cattccacag cccaagtgat ttactattac acgatgccac    13620
cttcctttta gtgattgcct tgtggcacag ctgcatgaaa ttgtggatac tgaggtcaat    13680
caggtcataa aaagcctctt ttgatctgat ttcatgctta tcaagcagcc ttctgaaatc    13740
tggcttcaca tactctacac caggggtccc cctggccctg gaccagtacc tgactgtggc    13800
ctgttaggaa ccaggctgaa cagcaggagg tgagtgtaag tgagcattac cgcctgagct    13860
ttgcctcctg tcgtatcagc ggtggcatta gattctcata ggaacatgaa ccctattgtg    13920
aactgtgcat gtgagggatc taggctgcgc actccttatg agaatctaac taatgcctgg    13980
tgatctgagg tagaacagtg ccatcctgaa accatctcct caccaacccc caaccccat     14040 ccgtgaaaaa attgtcttcc aagaaactga tcctggggac cactgctcta aatctacagg    14100
aaggaatgag atgctttgaa ataaacacct gagctccccc atatttacat ttcccactga    14160
acagtaatca agtatcactg tgactcagct atttctgttt tgagtttggg gtacgaaatc    14220
accttccctc agaagggaac tttggggtcc taaaaagatt aatttatgg tcctgacatg     14280 tcgaagacta ggtcttagat acaattaatt tcaccaagga cctgccattc cagtggcaat    14340
tcttggcagc cggacaggtg gcttttcctg gcaacacccc aacaaaaact tgagctcttt    14400
tgccaatgtt tacattgtgt actcatgatt tattatctac tggatctcag atcctttgtt    14460
cccgctggag taaagcaatt ttttttttt tgcactagtg cttgatgtct tgtggagtta      14520
ctatggagca agctgaataa ctgcagcctg gtgctgagat gttgggctca gtcttgccta    14580
tgccccttgt cactgaaaat gcccctgctc acagaaacac agctaggatg tatatatatg    14640
attttttttt gacaagatgg aaaccgtttg gattagggga agctgacgtc gttgctatgt    14700
atctgttcca tagcaacaat gacaggttgc caactcaatc agatgtgtcc cctcccaata    14760
ttaggctaca aaataatctg aaaattgccc aagtctcagg gagaggagaa agacaaagaa    14820
tcaagaaaaa caataaatat tagcacaccc cagagatact tctgaccacg aaagcttttct   14880 cattgctttc cagctccagt ccacaaatat caatgtaaaa ttttctattt tctgcaggtg    14940
acctgcgaga ctctgccact ttgagaactt ggcagatagt tactaaatac acagcataaa    15000
tataacctgt tggtcatttc tgtggtggtg gtgtgcttcc agcagactca gctcctcaac    15060
tcaccttaca agcttaattc atgtataaat ctgaccttcaa gctatgtggg aatttcattc   15120
atccattttc acactgctgt taaagacata cctgagacta atttataaag aaaaagaggt    15180
ttaatggact cacagttcca catggctggg gagtcctgac aatcacggtg gacggtgaaa    15240
ggcacgtctt acatggaggc aggcaagata gaaatgaaag ccaagtgaaa ggggaaaccc    15300
tttatgaaac catcagacct cgtgagactt attcactacc atgagaacaa aatgggggaa    15360
actgcccccc atgactcaat tatctcccac cggcttcctc ctacaacatg tgggaattat    15420
gggagctaca attcaagatg agatttgggt ggggacacag tcaaatcata tcaggaataa    15480
atgaagggac caacctcagt aggatggcct taatctgttg gttttcctgc ctctcctatt    15540
```

```
cttgtcctgt tctaatggtt ctatctttct gttttcagg agaacatttc aggataggaa   15600
taggccaagt gctgagaaga tgagtcttag gattgatgtg gatacaaact ttcctgagtg   15660
tgttgtagat gcaggaaaag tcacccttgg gactcagcag aggcaggaga tggaccctcg   15720
cctgcgggag aaacagaatg aaatcatcct gcgagcagta tgtgctctgc tgaattctgg   15780
tgggggcata atcaaggctg agattgagaa caaaggctac aattatgaac gtcatggagt   15840
aggattggat gtgcctccaa ttttcagaag ccatttagat aagatgcaga aggaaaacca   15900 cttttttgatt tttgtgaaat catggaacac agaggctggt gtgccacttg ctaccttatg   15960
ctccaatttg taccacagag agagaacatc caccgatgtc atggattctc aggaagctct   16020
ggcattcctc aaatgcagga ctcagactcc aacgaatatt aatgtttcca attcattagg   16080
tccacaggca gctcagggta gtgtacaata tgaaggtaac ataaatgtgt cagctgctgc   16140
tttatttgat agaaagcggc ttcagtatct ggaaaaactc aaccttcctg agtccacaca   16200
tgttgaattt gtaatgttct cgacagacgt gtcacactgt gttaaagaca gcttccgaa   16260 gtgtgtttct gcatttgcaa atactgaagg aggatatgta tttttttggtg tgcatgatga   16320 gacttgtcaa gtgattggat gtgaaaaaga gaaaatagac cttacgagct tgagggcttc   16380
tattgatggc tgtattaaga agctacctgt ccatcatttc tgcacacaga ggcctgagat   16440
aaaatatgtc cttaacttcc ttgaagtgca tgataagggg gccctccgtg gatatgtctg   16500
tgcaatcaag gtggagaaat tctgctgtgc ggtgtttgcc aaagtgccta gttcctggca   16560
ggtgaaggac aaccgtgtga gacaattgcc cacaagagaa tggactgctt ggatgatgga   16620
agctgaccca ggttagggag caatatccac aatggttgta atgtttgctg gcagcaaggc   16680
agggcgggtc agagaggaaa gagggatatg gtattccttg gaatctgggg aaagagattt   16740
actctctgat ttgcaattgt ctgacttatt aatccctgta gatgtagttc gtggattatt   16800
gcccttcctt tcttctgcca tcttaaatag tcttcattca acagatgccc tggctagtag   16860
ccccattaaa ggctggtgca gggggctgtt tgacctagtt atttcaatttt tcacatcctt   16920 tcttatgttc atagtcaagc ctcttatttt tcaattatga gcttgcattt aattatttag   16980
gaaatttctt tttttcacat gtacagatgt gtccacttta atttactgcc actttcctct   17040
gactttccct tcttaaatat tcacccttc tcactgccca cttccatttt ttgaaccaaa   17100
atatgaccaa atcacggctt tcgctctgct ttcccatttt tcctttgggg agccggtacg   17160
tgataagcca gaggatggtt ggtgacatgc atctatcctg gaaaaggaaa gcctgagata   17220
aaattagaca gagaaaacca atagtaactt cttcaaaggt ccagaaaaaa caaagtccac   17280
ctcagaatct gctcaggtgt ctatatccat tggcctttgc atcttctcat catttttctt   17340
taaaaagtag cattctaaaa atataaaaac agtctgggca cggtggctca tgcctgtaac   17400
tccagcactt tgggaggccg aggggggcag atcacctgag gtcaggagtt tgagaccagc   17460
ctggccaaca tggtgaaact ccgtctctac caaaaataca aaaaattagc tggatgtggt   17520
gacgcacgcc tgtaatccca gctgctcagg aggattgctt gaacctgaga gacggaggtt   17580
gcagtgaggt gagatcatgc cactgcactc cagcctgggc aacagagtga gactgtttca   17640
ataaataaat aaataaataa tagaaataaa aatagttttg ttttgacata ataaaattaa   17700
aaagtgttgc tttatgctag gttattttt ccttcaaaaa cctcagtagg ctttcctgag   17760
ctgacctgag atgtaaaggc aagtatctgt gggccgtggc ttgagttgta agactaggtg   17820
aaagactttg tagcacagct cagctataag ttggggtctg ccttttttgca tattgaatcc   17880
```

```
ttggttcttg tttcctaaga cctttccagg tgtcctgaga tggttctcca gttgagtttg    17940
tcatctgcca cgccccgcag caagcctgtg tgcattcata agaattcgga atgtctgaaa    18000
gagcagcaga aacgctactt tccaggtaat tggccatctc tggttgcttt ggaatatgtt    18060
gattgttcat tcatataaaa aattgactcc tactttatat tatatacaga atcaattcca    18120
gaggtttaag gacttaaata tgaaagccaa acctttaaaa cttttagtag aaagtgtata    18180
tgaataattg tatcattggg gtaggaaagc atttcctaaa ccagacacaa aaggatcaaa    18240
cttaaaaaga ctgataaatt ttactacatt aaaattaaga actgttcctc aaaatatacc    18300
ttaaagaaag tgaaaagact gggcacagtg gctcatacct gtaatcccag cactttggga    18360
gggtgaggtg tggaattgct taagtccagg aatttgagac cagcctgggc aacatagcaa    18420
gaccccatct ctacaaagta gcagcactct actatgccag gctaattttt taacttttgt    18480
agagatggag tctccctgtg ttgcccaggt tggtttcaag ctcctggact caagcgatcc    18540
ttccacctga gcttcccaaa gtgctgggat tacaggcatg agccaccacg ccaagccacc    18600 agtcttttt ttttttttt tgagatgaag tttcgctctt gttgcccagg ctggagtgca    18660
acggtgaaac tttggctcat tgcaaccttc acctcccggg ttcaagcagt tcttctgcct    18720
cagcctctca ggtagctgga attagaggcg catgccacca cacccagcta attttttttg    18780
cattttcagt agagacaggg tttcaccatg ttggccaggc tggtcttaaa cttctgacgt    18840
caggtaatac acccacctcg gcctcccaaa gtgctgggat tacaggcatg agccactgcg    18900
cccagcccaa tcatttttt gatggacttt tatatgacgt ctaattttt cattttaaa    18960 caatgctata atatacattt taccataata tacctgaggt gttctttaag gataaattcc    19020
aagtagtggc caggcacagt ggctcaggcc tgtaatccca gagctttggg aggccaatgc    19080
aggcggatca caaggtcaag agatcgagac catcctggct aacacagtga aaccctgtct    19140
ctactaaaaa tacaaaaaat tagctgggtg tggtggcatg cgcctgtggt cccagctcct    19200
cgggaggctg agacaggaga atcgcttgaa ccctggaggc ggaggttgca gtgagccaag    19260
atggcaccac tgcactccag cctgggcgac agagggagac tccatctcaa aaaaaaaaa    19320 aaaagaaaag gaaagaaaaa aaaaattcca agtagtaata attacttgta actttagatg    19380
gatattgcca gattgtaagc taaaacatat acccaaatac actttgacca accaacatgg    19440
tattatcacg gcatttctct tctggaagaa gcttagaatc attttatcct atcaaaaaga    19500 aaaaagatg gccgggtgag gtggctcaca cctgtaatcc tggcacttta ggagaccgag    19560
gtgggaggat cacttgagcc caggagttca agaccagcct aggcaacatg gtgaaactct    19620
gtctctacaa agaaatacaa aaattagctg catgtggtgg catgcacttg tagtcccagc    19680
tacctagaaa gctgaggtgg gagaatcacc tgagctcagg aagtagaggc tgcagtgagc    19740
catgatcata ccattgtacc ccagtttagg tgacagagca agaccccgtc ccccccaaaa    19800
aaaagtctcc atgctgtccc ttttttagtca aactctcccc aaatccctaa cctctagcat    19860
ccattgatct gttgcctgta cctatagttg tgctttacag aatgtcaggt aagtgaaacc    19920
atacagtacg taatcttgcc aggtgttaag atggcactct aatgccttcc tcaccatcct    19980 tgttccacc tctttgcctc gcactttgga tgtcagcaac acaaactgct tggagtgacc    20040
tgaatggacc ttgcttttta tttatttatt ttttttgag acaggatctc actctgttgt    20100
gcaggctgga gtgcagtggt gtgacctcag ctggctgcaa cctccgcctc ctgggtttaa    20160
gcgattctcg tgcctcagcc ccccgagtgg gtgggattac aggcacgcac caccatgccc    20220
ggctaagttt tgtattttt gtagagatgg ggtttcacca tgttggccag gctggtgttg    20280
```

```
aactcctggg cttaagtgat ccaactgcct cggcctccca tggtgctggg attacaggca   20340
tgagccacca cgcccggctt ccttgctgtt tcttgtccct gagtgttagt catgtgccct   20400
cttttgacca tgtctctatt ctcctcttca actcactaac tccaagtcat cctttaataa   20460
tcagctcagg gctgggtgcg gtgacgcacg cctgtgatcc cagcactttg ggaggcccag   20520
gcgggcagat cacttgagcc caggagtttg agaccagcct ggccaacatg gtgaaacccc   20580
agctctacta aaaatacaaa aattagccag gcttggtggc acacgccttt ggtcccagct   20640
acttgggagg ctgaggcagg agaatcactt gaacccagga gacagaagtt gcagtgagcc   20700
gagatcgcac cactggtgcg acagagcaag actccatctc aaaaaaaaaa aaaagaaga   20760 agaaagaaaa agaaaaaaga aaaaaagaa tcagctcagg tgtttccttc ttcataaaga   20820
cttccatatt ttcttctttc ctaaattgta cctttccttg gtattcacat aatactttct   20880
gtccttctct ctagttgtat tgaccacttt ttaccataat tattattgtc tgtttatacc   20940
agctaattag cgccccatca aaataagaat tgtttatctt tttattacta atgtataacc   21000
tattgtagat acatagtaga gtcccagtgt tgattaattc ttctacgtat aatgatgatt   21060
actagcttgt ctgaggcttt tctaatttct tcccatcctt tccctgtcta gtattttcag   21120
acagagtggt atatactcca gaaagcctct acaaggaact cttctcacaa cataaaggac   21180
tcagagactt aataaataca gaatgcgcc ctttctctca aggaatattg attttttctc   21240
aaagctgggc tgtggattta ggtctgcaag agaagcaggg agtcatctgt gatgctcttc   21300
taatttccca gaacaacacc cctattctct acaccatctt cagcaagtgg gatgcggggt   21360
gcaagggcta ttctatgata gttgcctatt ctttgaagca gaagctggtg aacaaaggcg   21420
gctacactgg gaggttatgc atcaccccct tggtctgtgt gctgaattct gatagaaaag   21480
cacagagcgt ttacagttcg tatttacaaa tttaccctga atcctataac ttcatgaccc   21540
cccagcacat ggaagccctg ttacagtccc tcgtgatagt cttgcttggg ttcaaatcct   21600
tcttaagtga agagctgggc tctgaggttt tgaacctact gacaaataaa cagtatgagt   21660
tgctttcaaa gaaccttcgc aagaccagag agttgtttgt tcatggctta cctggatcag   21720
ggaagactat cttggctctt aggatcatgg agaagatcag gaatgtgttt cactgtgaac   21780
cggctaacat tctctacatc tgtgaaaacc agcccctgaa gaagttggtg aggtatgctg   21840
cttgtctgtg ttcactttat tttcttgagt gactgtggct ggtgtggctt tcagtttact   21900
tgctaaaatt catattgtat ttaccatgac cagagggggtt taagagtaga atctgctttc   21960
tttgtttcat tggggaaaaa cctgactctg tttcttacag tttcagcaag aaaaacatct   22020
gccagccagt gacccggaaa accttcatga aaaacaactt tgaacacatc cagcacatta   22080
tcattgatga cgctcagaat ttccgtactg aagatgggga ctggtatggg aaagcaaagt   22140
tcatcactca gacagcaagg gatggcccag gagttctctg gatctttctg gactactttc   22200
agacctatca cttgagttgc agtggcctcc cccctccctc agaccagtat ccaagagaag   22260
agatcaacag agtggtccgc aatgcaggtc aatagctaa ttacctacaa caagtaatgc   22320
aggaagcccg acaaaatcct ccacctaacc tcccccctgg gtccctggtg atgctctatg   22380
aacctaaatg ggctcaaggt gtcccaggca acttagagat tattgaagac ttgaacttgg   22440
aggagatact gatctatgta gcgaataaat gccgttttct cttgcggaat ggttattctc   22500
cgaaggatat tgctgtgctt ttcaccaaag caagtgaagt ggaaaaatat aaagacaggc   22560
ttctaacagc aatgaggaag agaaaactgt ctcagctcca tgaggagtct gatctgttac   22620
```

```
tacagatcgg tgatgcgtcg gatgttctaa ccgatcacat tgtgttggac agtgtctgtc   22680
gattttcagg cctggaaaga aatatcgtgt ttggaatcaa tccaggagta gccccaccgg   22740
ctggggccta caatcttctg ctctgtttgg cttctagggc aaaaagacat ctgtatattc   22800
tgaaggcttc tgtgtgacag gaaacccaag cctaagaaac aattaagtgg ttctcatctc   22860
taattaactg tgaaaccatt taatccaaac atgtaagcac acactcactt attaagtcac   22920
atacttttct aggtgctggg gattgagaac gaatcgatgt aagattcctc ctttagggca   22980
gagacagacc actgacaaat acacagatag acaaggaatt tcccatggta aaagggata   23040 tcagtaatta gaggaccgtg agactcagag atgtgtgtgt gtgtgtgtgt gtgtgtgtgt   23100
gtgtgtgcgc gcgcgcacgt gcacatgtgt gtaggtagat ggagggggtg attattttgg   23160
gtggtcaggg aagtgctcag tgagggaaga acttgtcatg agaatctctg agcgtgccag   23220
gcagactcgg atatttttat aaattttta catggccact tgcagaagag cttgaatggg   23280
acgtgcagcg agaatgtgaa ggatggagca ggtagctcat ctggccttgt aggtgccggg   23340
aacgggcaag acatgttttg aaatgtaaga tcacagactg ttttttgcaa gaccacatta   23400 tattactta ttattttctg ctttttcttt taacgacatt agtgttttg atcactatat   23460 tttaaaatgc tttttgtgag ccttttggtt atgtggaatc tgttccttag ctctgatttt   23520
ttattcttat ggagcgtctt aggttactac atgaaggtaa gactgccaca gtcccccagg   23580
gaggcacact gtgttttact gattgatttg aagatgatag agagcctagg gggatgagtc   23640
tattggactc aaaggttaca ttttgttttt ccatttaatt taataatcaa caaaacgaca   23700
aagtcagttt aatatctttc ttctgctgag tcttcaggat gttagctagt ctttcaaaag   23760
ccattgctac aaaagtgcaa atttctcatt tcctgtgggt ctctagaaac tctctcaata   23820
tttaaagcca aacaaatcca tcttttctga gagacagaaa ctaaaaaatt cagagttaat   23880
tcactattaa aaacagcaag gccctgctat ttcccaagaa taaagaaatt taaaattctc   23940
attgtaagaa gtatgaactt gaagctagaa ttggtttatt tctggcagct acttacaata   24000
ttaagaactt tacttttaa atttgagaca atttcacagg aaagcaagaa attagtctat   24060
tgtgaaatgt ttttacaact aacttggaat atactgcaaa tcactagtaa gtagagacac   24120
atttaagata aaatgattaa taaaacaatt ggtaattctg aataaggatc tgaataaatc   24180
cagatcacag actgttcctt taccaatatg taaaagaatg tgcaaaatta gtaaaaatat   24240
acccaaaaat ttaccagcaa cagagaagca aagaatggag ttcaacctta cactataaac   24300
atctaataga tatgtatgaa aatttaaaaa ctagaaaagg ttgggcatgg tggctcatgc   24360
ttgtgatccc aggactttag gaggccaagg tgggaggatt gtttgagccc aggagttcaa   24420
gaccagcttg agcaatatag tgagaccctg tctctacaaa aacaaacaaa caaacaaaca   24480
aataaataaa taaataaaat tagctgggaa tggtgatgca cacctggagt cctagctact   24540
cagaaggctg aggcaggacg atcacttgac ctcagaagtc tgaggttaca gtgagctatg   24600
atcataccag tgcactccag tctgggtgac agaacaagac cctgtctcca aaattaaat   24660 aaataaaaca aaaaaaaaga atttaaaagt tttatataaa ggcatagcta ctatctcatc   24720
tgcccagtgt agtcatgaat agatgtcaca taaagaaaag aaaaccagaa ttcttgttaa   24780
tatggccagt ttgaagggtg gtggcggagg tattgagcag gcagctcagg gaaatgccag   24840
ggagacccct gagcacagaa actcctgatt gtcccaggg actctccgtg gacacaggag   24900
ggattttcca ggatttcaca tgaattcaat gaagggggct gtgtcttatt cctgatgct   24960 ttgcctcctt catggaattc agtggattta atggaagttc ctaggcaaca ataaagagta   25020
```

```
gaaaccaggt taacagcgag ggcctcatct cacaccagat catatcaggc tacacaaaag    25080
tagatggaag acaccaccca ggcctccagc tatacactgg agaagaagcc aaactagtct    25140
acttcatcta agaaagttgt caaagagagc ccttctatac tatcttaagg taaaaagaaa    25200
gactctaccc agctgccctg attaagcatt agaaagataa gtgttctgat cattaggcga    25260
aagacaatgg ggaaaaatgt agaaaagaaa tatgacatga ccagatgaa gaacccatcc    25320 tgaaaggata tataactcag gggacaaaag acaactcacc ataagttggg cgcagtggat    25380
cacgcctgta atctcagcat tttggtaggc caaggcaggt ggatcacctg aggtcaggag    25440
ttcaagtcca gcctggccaa cgtggtgaaa tcctgtctct actaaaaata caaaaattag    25500
ctgggtgtgg tggtgcatgc ctgtaatacc agctactcag aaggctgagg caagagaatt    25560
gcttgaatca aggaggcaga ggttacagtg agccaagatc aggccattgt acttcagcct    25620
gggcgacaaa gtgagaccct gtctcaaaaa acaaacaaag cctccccata gatgtctcct    25680
gccatagaag aatttaagaa gttcataaat tcaataaaac aagagttgaa ggcctgtccc    25740
actgtaccca atttctccct ctctgaactg cagcctagaa actctctaca ggcagtaagc    25800
tggggcagtc acagaggtga cctcatctgt ttcccacatc ctgcattagg acagtgatca    25860
gggatcagta tccttcattg actgatttcc aatatctcga gacctgttgt ttcatatatt    25920
ttgccttatt ttgcaattgt ttcatatatt ttgtcttatt ttgcaattgt ttcaggaggg    25980
aggataaata tggtccctgt tcctctatct tgaccagaag catctaagaa ggcagtgaag    26040
caacatgtgt acagttctta gggaaacaaa ttttgaccta aaatattaa acctagtcaa    26100 aatattattc tagtacaaag gcagcacatg ggtattttg aacataaaag agttctagaa    26160
atacaggacc catgaatcat tcttgaagaa aagttactca gtaaggaaat ctagctaagc    26220
aagcaacatg tacaaataaa agattattat aattggacca aagttaagtt taaatccatt    26280
cacatgtata taattaagat atataggaat tataattaca gaaagaatg ttacaaacct    26340 tcacaaagta aaaatatttt tatatcagat agattcttct gtttcaatcc ataaaaccag    26400
ggtttggatc attttaaaaa aacaaacaaa aataatttat tggaatcatt agggaggacc    26460
tgatagaata aaatgacaag ctgaccaaat aggccttaga agggagaggt gcctgggcag    26520
ttacaaggac ctaggtagca ggggtgactt ggccacagtc attttctta cttgatttaa    26580 ggaggttaaa ttacagtgag agagttgcac ttatttagtt tgcataccgt actcaactct    26640
tagctagcat agggcaggtt ccttagttga aaaatttcca caaaacatga tgtaaagtgg    26700
aaagatcagt tcccccaaag aatatcagtt accaaagtag gatgaaagga tgttgggtag    26760
atcaaaacaa caaatgtcca ttacagcaat taacaaaagt tagggagtgg ggaagtctga    26820
gtgctaatat ggatttcaaa acaactttaa aaatggcttc aaacattta tgctttttgt    26880 aatttagtca ttttaatatt agataaatct tcctgtaact gaaagttctt gagttaaaga    26940
aaaatattcg gtagttcagc tcttccttca attttattag ttgcttttc ttttgttcaa    27000 gtgaaataaa cataaaaata atttttaaaat attatgtatc atatccttcg atttaacata    27060
attctatcta gctgttctta tattttctct gatatatttt taaaagctttt ctggaatatt    27120 attaaccttg aatatttcta gttgatgagt ttatgagtga tttattgctt ccttttctct    27180
ttcagtattg ctagaattaa ttttattgac tttgcccctt tgcataaaga ccttgaaggt    27240
cacatgctga aatcgccctc tactaaaaca aactcataga aataatgggg aagatatttc    27300
aaaacattgc catatgcata gccatcctca caaccaagaa aagcgcctct ccatgaacta    27360
```

```
aaacctatga gtcattggta caggtaggga aaatctaggt aaaccacggt aatacactga   27420
ggctggcacc accacaggcc aggacaaccg ttgtcacaaa gccaggacag aatctcccag   27480
ccagaaagtg ttgccctgag gctgaagcca aattcatttt gccccagtt ggccagacca    27540 aagcctagaa ctaaaaaacc catacctcag ggtttgtcag cattggcact gctggctttt   27600
tgggctggac aaccatttat tgtgagaggc ttctctatgc actgtaggat gtttagcagc   27660
atccttggcc ctactcccta gacgccagta gcaaatccac caccctccct cccctacccc   27720 aggggttggtt gtcagttgtg acaaccaaaa atgtctccag acatcgccaa atgtcccttg   27780
gggggtaaaa tcaccaccac catacctctt ttgactaaaa gagtttccag aatagtggca   27840
gaatatatag gtcaagcata acacattaca atcaagattc agaacatcaa agattctttt   27900
ttaatcctaa aagaaaaagt ttggaaaatc tacaaaaaga agtgtgaatt tgacaataac   27960
tatttcacta gcaagggtag acgtaagcag aatacaggta gcatattcaa actgctgtgg   28020
aaaaacaaca tcaaacctag acttctctcc ccaaactatc attcagagtc gagggcaaaa   28080
taaatagatt ttctgacttg gaacaagtag gaataatgta cttatagtat tcatcttcat   28140
acagggatgg actataagtg attttttaaaa aacttcctac ttgttccaag tcagaaaaac   28200
tattcatata gggatgggct attagcaaga gtatatgaat aacgtactat aacaagaaaa   28260
aatgaattga gaagaagta gtggtttttaa gaaggaaagg agaacaaata aattagtgaa   28320
acataaggtt aagtctatac atattatttt ctaattgcct attatgtcag actacatgta   28380
gttagaaaat acgatgaaag aaaaagccat attataattc caacaaaaag ataaaataat   28440
taagaataac tgcaacaaga aaatataagt tctgcaacaa taaaactata caatgaaact   28500
aaagagcaca aaaagaact taaacagata aaaagcagac cacgtttttg gataagaaga    28560
ttaaaaatta taaatatatc aatttttcact gttaatctat aaattcagtg taatcccaat   28620
aaaaatgcca acaggttttc cccaatagca ttgaaatgat tttaaaattt aatgaaggcc   28680
aagcatggtg gctcactcct gtaatcccag cactttgaga ggccgaggca ggtggattgc   28740
ctgagtccag gagttccaga ccagcctgga caacatggtg aaatcccgtc tctatttaaa   28800
atgcaagaaa ttagctgggt gtggtggtgt gcacctatag tcctagctac tcgggaggct   28860
gaggtgggag aatcacccaa gccttgggag gtcgaggctg tagtgagcca aaatcacatc   28920
actgcactcc agtctgggca gccagagtga gaccctgtct caaaaaaaaa aaaattattg   28980
gaaactacga ggcaagaata tccaagaaaa atctagaaaa gaagaaacct gagtgagtca   29040
gcatgaccaa atattaaaac atcttataaa gctacaataa ttaaaacaat gtggtgctga   29100
tatgtggagg gtcaatggaa caagatgaaa tggccaaaaa taaatttaaa atacatgttg   29160
aaatgtatta acagcatatg ttaaagttaa gttatgttaa ctttatatgt taaattcaag   29220
ttaattgggg aaagatggat tattcaatat atgatgaaca actctgtcac ccagctaaaa   29280
aaaattaagc ttgggccata tgccagacta gataccaaaa taaattccag gaggaccaag   29340 ttttttaaaag taaaaatatg gaatcatgga agtgcatgaa gaagaagtag cacttaaaaa   29400
aataataatc tcagcatggg gaaggtctaa gtatggccct caatcagaaa ccaggaagga   29460
aaatattgac tattttaaac aaaattatct ctgtaccaaa aacagcataa aaggtcaaga   29520
aacaacacac tggaaaaaga attgcaatga atatcacagc caaatagtta atttcttatt   29580
ttcaaaaaat agcttctaca aatcgaagag aaaaattcta aggtctcaaa ggaaaaatga   29640 gcaaggatt tgacaggtgg tagaatacag aaaaagaatt taaatagct cctaaagata    29700 tggaaacatt actcatgata gcagaagtat caattgacaa aattactcag attggtaaca   29760
```

```
aactttaagg gggaaagcac ttccatgcat tgctgtaaat tggtacatct tctactgaga    29820
acaatccggc agtagttaac aaaattgtga atgcatatat ctctttctct agaaatttct    29880
cttttgggaa tttattctac atatatattc aaacgtgtga aatacttcta tacaggtgat    29940
tgaatttcac tttattccta agagcagaag actgcaaaat agtaaatata tacccaaaag    30000
ggtctaatgg attagttttt ggcatatcag cacatgataa tactatgaag ccataaaaaa    30060
gagagatctc tatatgtatt gatgggggac catctttaag atatactgtg gtgttgaaca    30120
aaacaacatg ctgaaaatgt ctcttattct tttagaatca atataagtct gtgcttgtaa    30180
atgcagtaag tatctttgga agtataccta aaaattggta atagtgtttg actccaggga    30240
agaacagatg ggtgccagag tgaaaaaaag atagcttttg cttttttatga cttttggatt    30300 ctgtaccacg taataatttt gatgtaaatt ttgctgtgtg tgttttttact tgttcatgta    30360 gtgattttat aaattactct tttaattttc tatcaatgaa tatcctggga taaacccctc    30420
atgatcataa tgaataatga tgtgtggaga gtggggaggg tttacatatg aaaaatgtag    30480
aaaatacaaa aagtgtctat atatacaaaa atgtaagtgt taacattttt atatttgctt    30540
caagcttttt ttttaaataa aagaaatgca atattgcaat taaa                    30584

<210> SEQ ID NO 5
<211> LENGTH: 20406
<212> TYPE: DNA
<213> ORGANISM: Homo sapiens

<400> SEQUENCE: 5
attgtgcggc gctggtcccc tcagagggtt cctgctgctg ccggtgcctt ggaccctccc      60
cctcgcttct cgttctactg ccccaggagc ccggcgggtc cggactcccc gtccgtgccg     120
gtgcgggcgc cggcatgtgg ctgtggggagg accagggcgg cctcctgggc cctttctcct     180
tcctgctgct agtgctgctg ctggtgacgc ggagcccggt caatgcctgc ctcctcaccg     240
gcagcctctt cgttctactg cgcgtcttca gctttgagcc ggtgccctct tgcagggccc     300
tgcaggtgct caagcccggg gaccgcattt ctgccatcgc ccaccgtggc ggcagccacg     360
acgcgcccga gaacacgctg gcggccattc ggcaggtgag accccacgt tcgcgcccct     420 cggtcctccc gagagctcgg acttctactt ttccttccca gggttccccg atcttctcag     480
gacggccttc ccacttcctc attcgtccac aaggcacact cccggccctt gatcgctccc     540
agtgtctagg gatctccgga cttgaggttt tatatttaca gaagacagca gatatgtata     600
tagtttctgt gcgcctgacg ctaaggttac atacagccag gaacaaggtc aaaagtgtcc     660
ctggtttaca gagtgtacat cggaatgggg gaggcaagcc ttaaacaagt aaacacataa     720
atgagataac tttaagagag tgaaaggtgc aatgaagaaa tcgggggaac tcgaaggaaa     780
gagttacgct attttatttta gatggaatag tcaagagaaa tcgtctccga agaagcaaca     840
tttgaacaga aaccggaatt ataaggagcc aggcaggtgc agaaggtcct gagatgggaa     900
taatataggg gtgttcaggt aacagaagag gcagtgtgtg gcctgacttc aaggaagaga     960
acaaagactg tgtgtgaat gaagtagaaa atgggtcagg tcaaataggt tcttggtcag    1020
taattgaggt tagtctaaat agatcaccct tcacaagaca tacgtttgct tgtcttgtaa    1080
atcacttgag tcatttcctt atcacctttt ccccagacac acacattcgc actcgcacaa    1140
ccctggcagc tggactcaca tcagtttctg cccctccctt ttcacaaggc actcctgaaa    1200
cttttgatac ctcccagctc ttggcattct cctagcttca taataatgac agcttacaga    1260
```

```
gagggcttttt cagtggatta ggcacttttg catctgtgta aatatatctg attctcttct   1320
tttttatttt tctctctctt cttccttcct tcttcttctt tttttttttt ttacttaca    1380
gagtctcact cttttaccca ggctggaggg cagtggtgca atctccacgc actgcaaccc   1440
ctgcctccg tgttcaagcg attctcgtgc ctcagcctcc ggagtagctg ggattacagg    1500
cgtgtgccac cacgcccagc taattttgt attttagta gagatggggt tctgctatgt    1560
tggccagact ggtctcaaac tcctggcctc aaagtgatcc acccgcctcg gcctcccaag   1620
gtactaggat tacaggcatg agccatcatg cctggcctcc ctcatttcct ttttttttct   1680
ttttttttt cttttttttt aaacgaagtc tcactgtctc ccaggctaca gtgcatcggc    1740
gcaaccccag ctcactgcaa cctctgtatc ccaggttcaa gtgattctac tgcctcaacc   1800
tcccgagtag ctgcgattac aggcatgagc accgtgcccc ggccaagatt tatactttta   1860
aagctgcact ctggcccatg tggagaatgt actgtgggtg taatttcatt cctttgccac   1920
tgtttatagt agtgtatctg tttttggaat acactcaact cacatttatc aagttttcc    1980
ttctatatct catttataat ctaccagaaa ttctagcact gtcagaaatg tatatatgta   2040
tgtatacatt cgactttacc aataatttta tttatttatt tatttttgag acagggtctc   2100
tctctgtcac ccaggtttga gtgcagtggg gcgatctcaa ctcactgcaa cttccacctc   2160
ccaggttgaa gcgattcttg tgcctcaggc tcccaagtag ctaagattac agatgtactc   2220
ctccactccc agctaatttt tgttttttgt tttagtaga gatggtgttt tgccatgttg    2280
gcaaggctgg tctcaaactc ctgacctcaa gtgatccacc tgcctcagtg gattacagag   2340
tgctgggatt acaggcaaag tgctgggatc acaggcatga gccactgcct ggccagcttt   2400
accagtactt ctatgttatt ccagtaattg agataaaaag atgaatccct ggttctaatt   2460
cacatattag tatatatagg agatattgca agttcagttc cagacctgag taaatagtca   2520
ataaagcaaa tatagtaata aagggagtca caaatttttt ggtttcccag tgcatataaa   2580
agttatgttt acactatatt gtaatctatt aagtattgtg tatgtatata tatatatata   2640
tatatatatg cacatacaca cacatatata ggttttcatc catggttcct ggctcataac   2700
tctcagcccc tgctacagta ttttgttagg catcctaggc cttaggagca ggccttggga   2760
aacagaatct ctcctgcccct cctttcacct accccaaggc aggactggaa tctttccctg   2820
tctttcaaat tgtgagtctt aagaccctcc tcagagaggg accccaccct atacccctggg  2880
ggaaggaatg ctgacatcat gaagcttcca taaaaaccta agaggaatta aaaaaataaa   2940
aactaaaata aacctaagag gacttgaagc caattggtca gaagttccat aggcccccagc  3000
ttgctatttg tgtctggagg agggtggggt gcagtcttgg ggaccaagcc ctcaacctat   3060
gatctgacac tatctccagg tagatagtgt caaaattgag ttggaggata cccagctggt   3120
gtccactact tattggtggg gaaaaacccc cacattttg gtcacagacg tcggggttga    3180
ttgttgtgag agcagaggga aaatgtgatg tgtttttcca aaatagtcgt acatctgtat   3240
cacatgggaa aaggaaaaga tttaaataaa gcagaaaaat ctccacccat aaaggacgtt   3300
attgataaat ttgactatat tacccttaaa gatgtgttta aaaggacata ataaataaca   3360
atggctaaca tttattgaaa tcttaactat tcactagcac agtgctctgt gttgtttatg   3420
ggtacttaaa taaaaaccgg taagggagtg acatgagaat gatatacacc aactttaaga   3480
tggtaattac ctctggagag gaaggagga gaatgaaagg gagaatttca gctgtatctg    3540
tagtgttgat agtaaaactg aagcggataa gagtgcaact tctactgcat cctagcttgt   3600
gcagccctgg gcaagtttcc tactctttct ttgtctcagt tttcttatct gttaaatgag   3660
```

```
aatattaata gtacctgctt cagggttgtg aggatcaaat aagttaatac atttaaagca   3720
cttagaagag tgcctggcaa gtagaaaagg ctcaataaat aatagttttt gtttttgttt   3780
ttgttttagt acagaaagag actgaggaaa ttaggtcaaa atattcacat atgttaaatc   3840
ttttttactg tagatgtttg caatagacca tgacttaaaa tatttttttaa aaaattaaaa   3900 atcttgatca tagctgggca cagtggctca cacctgtaat cccagcactt tgggagactg   3960
aggcaggagg attgcttgat ctcaggagtt cgagaccagc ctggacaaca tggtgaaacc   4020
ccatctctac aaaaaataca aaaattagct gggcatggtg gcacgtgcca gtagtcccgg   4080
ctacttggga gactgaggtg ggaggatggc ttgaacccag gaggcggagg ttttagtgag   4140
ccgagatcat gccactgcac tctagcctga acaacagagc cagatcctgt ctccaaaaaa   4200
aaaaaaaaag aaagaaatct tcatcgtaat gagcatttca catctttatt gtgatgagga   4260
agccaaggaa gcaaacatta aatagtgtgt ctccagagga gcatggctcg tgtaatttaa   4320
ggttcaaatt ctcttttttag ataaattcta atctacctca tcaagcttaa caacttatgg   4380
gccaacagcc agtgctgctt acataaacaa aatgtgatat gtcctagaag caggcgtggt   4440
gtctttgtgg tagagggtgg aattaaacca acaaaaacct gactcattta tgccaaagta   4500
gtgaaatatc tgactaatca acaaccgtag ggtgatcatc agaactgctg taccaacaaa   4560
tagtgtaggt aaacagtgga attgtctaag tattcataag ccattgatga cccatatagt   4620
taaacatcca gagaaaacat aagttcctga agtctcctag tcttccactg tgaaagtaag   4680
aagagtggga aaattaaagt ttttaaggaa tccatcagtt aggaattgaa gtaaggttat   4740
atacacagaa aacagaaaca gatcaggatt gctgtttggt gggggaagtg gaaggaaaat   4800
gaatcaaaaa ggacagctgt cttaggagcc ctgctggtct tttgggtggt tagatgcaaa   4860
ataatgtttg tggccatttg acagtaatat tcttgatgtt tttgttaagg cagctaagaa   4920
tggagcaaca ggcgtggagt tggacattga gtttacttct gacgggattc ctgtcttaat   4980
gcacgataac acagtagata ggacgactga tgggactggg cgattgtgtg atttgacatt   5040
tgaacaaatt aggaagctga atcctgcagc aaaccacaga ctcaggtaag tagtttattg   5100
tcacttaaac agatcttttta gcttttattg gaaatgacag acactggtgc cttctaatta   5160
catctgcccc aggagagttg tcttgttttg ttttgaactg tacgtaggtc ttgtaagtaa   5220
tgagcaagtg ccaggaacaa cagaaatttg gcattatgtt tttaatcttt cccactgagg   5280
ctaaatttgg cttcagaatt attgtcaaga taatactgtc tagtcataga atcatgaggc   5340
tgaaagtcat tgcttggcaa tcttcttgcc ttcaggtgta ccaagaagca aattatacat   5400
tcattaaaag cttcaagtaa cattataata tcacatttta acttaaccca tttaattctt   5460
ctgatcctca taacaaactt ctgaggaatc acagaattgt aggaatagag agtatcctag   5520
aaatcatcta gaatagcact ttgcagtaga actttctgca atgatggaaa tatttatat   5580 ctgcactgtg taatatggta ggtacttgtg gctattgagc acttgatatg tggctagtga   5640
cacgaggaag tgaattttta atttaaatgt aaatttaaac tgaaatagcc atgtgtggct   5700
accatatagg atactacaga tctagatcaa tcttgccttt agatataatc ccagaaaagt   5760
taaattattt actcaagggc aaataactag ttcataaaga agccaaaact agaatctatc   5820
ccaagtttta gtccaaatca tgctgttttt agctgccccc aatgtctttc aaccctgtaa   5880
gagcaaaagt tctttcagtg tctaatttaa ttccttcctg gtagagtgta aacgtagctt   5940
ccaaagtata tacactagag ctaatcttac aagatgttct gcaaaaacag ggttcaagta   6000
```

```
agatcaaaca gtgtattctg aatacttctg ttgtggataa acagtccaca tcagctgatt    6060
cttacttgta acttagcttt tctcaaactt acatgatcac agaacctaca tcctcttccc    6120
cacttacagc ggtaaacacc cttggaattg gtatgctgag taatatactg tactttggaa    6180
tgtggttatt taaatccctc tctgcttgtc atctttgcag tactgaaaag ggtgtgctca    6240
ctggttattc atgtaatatc aattatccag acaatgatcg attctcttgg aaaattaagt    6300
atttgaccca acagttaagt tatactttt cctaaaagat gatccagacc tgttttccta    6360
ggatctgaaa aacattagtc tgccgaagga agtcatactg taggcaggaa agaatattgg    6420
taacacttga gaattatgag tccaagttgc tagaattgtt cttgagtgtc atcagatact    6480
gtattgctct gcttatgcaa gggaaaggct ggtttgaata ttataatgac attgcagcta    6540
ataaaatgtc aggttcaaag ttaatactta agcaaaaat gtttagggtc atcattaccc    6600
ttaaaaatcc tttaagggag cactgagtcc atttctctgg aatttgtgca tcctaggaaa    6660
aaaaattgtg attttcaaaa aatcccttaa gaagacagca aaggcaacat attatctcag    6720
tgtctttaac acaaccagtc tttgctccac tattggaaca gagtgtgttc tatgattgaa    6780
aactaaatga agtaattggc ttgtgtttac ggattatgtt gtgggaaaaa atagatattt    6840
tctctagaat tatgctcagt gtgatgagat gcttgtcctg agaggaggat aaggaggaaa    6900
ctaagatcag ccaaaggaat aacaaattca ggtctcccat ctttcactct cagggaatag    6960
aaattgatta gaatggctgg gataattgcc tgtaatgttt aaattatcct tatctttttt    7020 ttttttttt ttgagttgga gtttcactct tgttgcccag tttggagtgc aatggcatga    7080
tcttggctca ctgcaacctc cacctcccgg gttcaagtga ttctcctgcc tcagcctcca    7140
gaatgctggg attacaggca catgccacca cacccagcta attttgcat ttttagtaga    7200 aacgggtttt cgccatgttg gccaggctgg tctcgaactc ctgacctcag gtgatctgcc    7260
tgcctcagct tcccaaagtg ctgaatttac aggcatgagc ccactgtacc tggcctatcc    7320 ttacccttt taaaagcat gatcttacag ttgaaataat gcagttgaat tagcattaag    7380
ttaaataata attttattat gagagaaaag ctaatttctt ttgtatcaag cacttagttt    7440
tcattttctt tatcagaaaa ttatgtctta gaacattatt tattttaaac agttgcactt    7500
aaataaatac acaatacagt taacagattt atgtattcct aagaattcct cctgcatagc    7560
attctattag ggaaattaca atctgaaaat taagtctttg agttttccaa aggtggcata    7620
tactctgccc tttgggaagt agggttatta ataatgttat taattcaata gaaattcagt    7680
gatttcttaa aaattaaatg attttttgttg ttgttgctgg tctttggtca agaatatctg    7740
tatttgaaca catggaggtt cctgaatgat ggagcactca gaaagggcat ggaagctcta    7800 tgccccttc cccatacctc accctatgca tgtcttcatc tgtatgctgt gtaacatact    7860
ttataataaa cctgtaaacg tgtttgagtt ccgcaagcca ctctaacaaa ttaattgaac    7920
ccaaggagga ggaggtggga accccaattt atagctagtg tcagaagcac agaattacca    7980 gaaaggaaa acaaatcaaa acaaaacaaa acaaaaaaca gaaaaataac atccattata    8040
caatataaga aaccaaagac catcaatctc taatctctgt gctcaggtgt ctgtgtgctt    8100
caattcttct catctacgag tcttgggttt tcaatgctca cttgtcacca ggatatgaat    8160
taaaaatgtc ttgggcacca ccatgtggtc cagttgtctt aacctttcta aaagtgcttg    8220
tgcaaaccat ttacttgttg cttcttacac aattacagcc caacctactt gtgtttaaaa    8280
gcaaccacag catgttgaa agtcttatgc aataaaaggg aagttatga ttacatttag    8340 tctgtactta ctggatactt tcagtttat cagttccaag tacagcaaac tctggataat    8400
```

-continued

```
atggttaatt acttcctcca tgattctttc gaccttcata tcaatttgc taaatatgga    8460 atgattgact agccagagca atcaggaaag agaaagaaat aaaaggcatc caaattggaa    8520
aaagaggaag tcagattgta cctctttgct gacaacatga ttttgtatgt agaaaaacct    8580
aaagacttca ccaaaaaact gttaaaactg ataaacaaat ttagtaaaat tgcaggatat    8640
aaaatcaacg tacaaaaatc agtagcatgt ctatacgtaa ataatgaact agctgtaaaa    8700
gaaatcaaga agtaatccc atttacatag ctaccaaaaa aaaaataaca aaatacctag    8760
gaataaatat aaccaaagag gtgaaagagc tcttacaagg aaaactacaa aacactgatg    8820
agaaaactta agaggacaca aatggaaaga catcccatgc tcatggatca gaagaattaa    8880
tattcctaaa gtgaccattc tactcaaaat aatttacaat tcagtgcaat ccctatcaaa    8940 atatcaaga cattcttcag agaaatagaa aagcaacaat cctaaaattc atatggaacc    9000
gtaaagaagc ccaaatagct aaagcaatac tgaacaaaaa ggacaaagct ggacatatca    9060
cactacctca tttcaagata tactacaaag ccacagtaac caaaacagca tggtattggt    9120
ataaatactg acacacacac acacacacac acacacacac acacacacac aaaacagata    9180
catagaccag tggaatacaa tagagaacca agaaataaat ccatatattt acagccaact    9240
gattttccat gaaggcacca agaacattac agtgggggaa aggaactctc ttcaataact    9300
ggtactgggt aaactggata tccatatgca ggataatgaa actagacccc tatctctcac    9360
tatatttaaa aaatcaacac aaaatggatt aaaagtttaa atttaagacc agaaactata    9420
aaactactag aagaaaacac aggggaaaag ctctgggaca ttgatctagg caaagatttt    9480
atggctaaga cctcaaaagc acaggcaaca aaaacaggca aatgtgacta tattaaacta    9540
aaaagcttct gcacagcaaa ggaaataatc aacagagtaa aaagaaaacc tgttgaatag    9600
gagaaaatat ttgcaaacta ttcaacagac aagtaactaa tatccagaat atacaaggaa    9660
cttaacagca aaaacaataa taatcccatt aaaaacatct attcaaatcc taatttgaat    9720
aaacattttt caaaagagga cacacaaatg gccaacaggc atatgaaaaa acaccacaaa    9780
ttattaggga aatgcaaatc aaaaccacaa tgaagtacca tcttatctag ttagaatggc    9840
cattatttaa aagattttta aaataacaga tgctggcgag gatacagagc aaaaggaact    9900
cttatattct gttggtggga atgtaaatta gtacagccat tatggaaaac agtatggagg    9960
tttctcaaaa aactaaaaat atagaactac catacaatcc agtaatccca ctagttggta   10020
tctatccaaa agaaaggaaa ctagtgtatc aaaggcatac ttgcaccccc atgtttattg   10080
caacactatt cacaatagcc aagatacaga atcaacctaa gtgttcatca gtggatgaat   10140
ggataaactg tggtaaatat actcaatgga atactatgta gttagccata aaaaaggatg   10200
atatcctgtc atttacagca acatggatgg aactgaaggt attatgttaa atgaaataag   10260
ataagccagg cacagaaagg caaatattac atgttgtcac tcatatatgg gagctaaaaa   10320
agttgatctc atggaggtag agaggagaat gatagttacc agaggctggg aagggttttgg   10380 ggttggggga agaggagaat aaggagaatt tggttaatga gtacaaacat acagttcgat   10440
agaaggtata aattctagtg ttcaataaca tagtaaagtg attatagtta acaatctgtt   10500
gtatatttca aaatagctag gagatttaga tgttcctaac acaaagaaat gataaatatt   10560
tggggtgatg acatcctaa atacctgat tttatcatta tacattatgc gcatatcaca   10620
aaaatatgtc taagtgtata gcaataaaaa tgtggaaaaa agaatatcta aatttggtt   10680 caaattatta cagtaggaca ggcgcagtgg ctcacacctg taatcctagc actttgggag   10740
```

```
gccaaggcag gtagatcact tgaggtcagg agttcaagac cagcctggcc accatggtga    10800
aaccccgcct ctactaaaaa cacaaaaaat tagccaggcg tggtgtcaca cgcctgtagt    10860
cctagctact tgggaggctg ggcgggaga attgcttgaa cctgggagtt ggtagttcca     10920
gtgagctgag attgcaccac tgcactccag gctgggcaac agagcaagac tccgtctcaa    10980
aaaaaaaaaa aaaatctta aagtaaagta tctttggact ttgctatggt cgaaaaaagg     11040
aagttggaga aaacactctt tcctttgat tgagagacat atgcaaaatg tttgttgcaa     11100
tacagtttat ctgtttctct ttttcctac aacgtatttt ctcttctctt acaggaatga     11160
tttccctgat gaaagatcc ctaccctaag ggaagctgtt gcagagtgcc taaaccataa     11220
cctcacaatc ttctttgatg tcaaaggcca tgcacacaag gtacagttta aattgtggac    11280
ttcactttgt taaaagaca tcttatttca ttgacggtca tttccgaagt tacatatatt     11340
ttgttattta ttcttttaa aacttatttt tataaattgt atttgtttaa tggaagtgta     11400
caatgcagga atctatatca tttaaggaaa cagtgcatta tggaactttt taaccttta     11460
tggaaacttt acaaaaccag cataaaatgg aagagtcaag tttctattat ttacataaag    11520
catttacaaa agatattaag taaacagtaa aaaagacatt tctagaaaaa aaccactgta    11580
gtaaccttga gttacttgaa aaaaggaat tccgaagttg tacacaagac caattttatc     11640
tagcttaaaa gttaagggcc ttatatggac aactatggac tgcatttaaa gagaattcct    11700
atattaaaag cttctaatag ttaacagaac atataccttt tacatagatt tatcccttg     11760
tataatttat atcccttatg tatagttttt tattcattga ttttagcagt tatacttta    11820
tcagaaaatc atttattttc ttcaaatgta tttgacattc ctagataaaa ttttgcttaa    11880
attttagggc ctgcacttac actcataaga acatattatt acagtgaaaa tcagtgggaa    11940
gatatgattc tgattacatt tgttctctta taaccagctt ttcaagtgca agtacttttt    12000
tccccatttg ggcaacttga gtatttttcc cctagcaata ttaataatcg gtaagggcca    12060
tctactggtt gagaattctg atgatgccaa ttttttttt taattaatcc catgatatca    12120
ttgaaccag ttgttaaaac ccaaaatggg ccgggtgcag tggctcacac ctgtaatccc     12180
agcactttgg gagtggatca cctgaggtca ggagttcgag accagcctgg ccaacatggt    12240
gaaacccctg tctccactaa aaatacaaaa attagctgga cttggtggcg gcacctgta    12300
atcccagcta ctcgggaggc tgaggcagga gaatcgcttg aaccggggag acagaggttg    12360
cactgagccg agattgcgcc agtagtactc cagcctgggt gacagagcga gactccgtct    12420
caaaaaaaaa aaaaaaacct gaaatgtgga gcctaagtat acactctaat tttattaaca    12480
gttaattcct atttttgaag aaggaagata atggtaacta atttattatt ctagtaaacc    12540
gatagttgta tacgtctagg ttttccaatt ggtctgcgtt agaatcacct gtacctattt    12600
taaaatataa attcctgggc cattctccct agggaagaga ttctgaaaat gtctagggtg    12660
ggctcaagga acatgtattt ttaatgagca cctcaggtgc tcattgttga tgttgcagcc    12720
cacatttggg aaccctgata ggtcctacat ttcacccatg gtatactgac ttttatgctt    12780
attctcttag attttttgag acagagtctc actctgtcac ctaggctgga gtgcattggc    12840
gcgatctcgg ctcaatgcaa cctctgcctc cggggttcaa gcaattctcc tgcctcagcc    12900
tcccaagcag ctgagattag aggcatgtgc catcacaccc ggctaatttt tgtatattta    12960
gtagagatgg ggttttgcca tgttggccag gctggtctca aactcctggc ctcgagtgat    13020
ccgcccacct tggcctccca agtgctggg attacaggtg tgagccacca cgcctggctt     13080
ctcttagaat acttttaaa aagaagtaga catttaaaaa agaaaatcta gctatttgag     13140
```

```
tcttctgaat gggtgctcat gggtgttcag ccaagactgg gtagaacata gtgacctaat    13200
tcaccaagat ggtagtagaa aggcacaagt gtaggcaaca aagtggagct agtagagcac    13260
agtggccaaa atcatgggct tgggactcca acagtccttg actgagctct tactacaggg    13320
taaccttaac tttgatgagc ttcagtttct tcatgggtaa aatggggata ctaaaagcag    13380
ttaccacata aggttgttgt gagaattaaa taatgtaaat gctaagagtt tacagtgcat    13440
gtctttgttc aaacagaaaa aaaaatgctt tctatagctt gccttcagtt gcattagcga    13500
agaggaggca tgacatggat aatttgtgtc cttttttatt ttggtggggg aatgcatttt    13560
gctcatcata tttggttagg ggtatgtgta acattccaaa aattagcagt gtttcacaaa    13620
ttatgcagca gcagcattgc gtcccacatg gctggtgact ttcttgttgt tagctgctat    13680
tgatgtcact tcactagggg ttaccaaata atacttaaat tctatcatgt cttcttcatt    13740
tcgtagctag actactataa aaagaaactt ctgttcacct tgggaagaat tgggagcccc    13800
ttaactcttc ccagtccctc ctaccctgc cccattactt ctccctccat attggtgatg    13860
ggtaatgcgt cctctcagtc ccctggactg agaaatctat cctctgtagt tcccagactg    13920
gctggctcat gtttcattta gaaaaggcac agagtgatag agctgtgggt atgaaaggac    13980
ttttcatagt ggctaaacta gggtataagg caaggaaaat tttgcctctg gcctcatctg    14040
acctacggct taccacactt ttcaaaagta ttccaaaagg ggtgaggccc tcagaggag    14100 taaagcagca gtactccacc ttcttccttg tttgctgctg gtgtgagttt aaaatgcatc    14160
ccagtggata atagactcta ccaatacttt cagtacctcc atttctagta aacttctgtt    14220
ttattccata gggttgtact aatatgtga tagttattgg ctggggctat ctatcacatt    14280
ttaatcaatt ttaaatatat gaatctcttt atttttacagg ctactgaggc tctaaagaaa    14340
atgtatatgg aatttcctca actgtataat aatagtgtgg tctgttcttt cttgccagaa    14400
gttatctaca aggtaacatt cgggattttt cttgtacata ttaggtgagc tggtgtagat    14460
aattgcaatg ggctgcgtaa gcacaggata gatgccatt aaattgaact gcatcagggt    14520
cacagttgag aagctcctct tttaaattaa ccagagaaat tccagaaggg gaatgtactc    14580
atacccctta cagaatgcca ttattcctct tttgcccctt cttttatgtt gtttataggc    14640
tcactcagat tactgtagta aaattctcac aacagaaaag aattatgtag cccctacttc    14700
tcaccaacta acagcagaac ataccttcat aaaataaatt cttaattatg gagaatctaa    14760
aacatgcata aaataaagta gtagtgtacc ccccctttaa ctgtgatcca gctcatttca    14820
cccataaccc cattgatcct ccccagtgtt attttgaagc aaatcttatt ccatccataa    14880
aattgcatta agaatcttta aaaagtgatg ccattttatt tatttattta tttatttatt    14940
tatttattta tttatttaa aagacgggt ctccctcagt ttcccaggct ggagtgcagt    15000
ggtgtgatca cagctcactg cactcttgac cttccaggct caaatgatcc tcctgcctca    15060
gccttccaag tagctgggac cacaggcgca cgtcaccacg cccagctaat ttttatttt    15120 tattttttgt agagacaggg tctccctgta ttacccaggc agttctccaa ctcctaagct    15180
caagcaatcc ttccacctca gcctctcaaa gtgctgggat tacaggcatg agccacagta    15240
accagcctag tgatgccttt ttaaaaacat agccacaatg ccattgtccc atctaaaaat    15300
tattaacaat aaattattca tatcatcaaa tatccagtgt ataaattttg acttgtctcg    15360
gaaatgtcat aaatggttgt ttttcataaa ttgctcattc gaataggacc caagtaagat    15420
cggcgtgtta caatcgtaaa tcttttttg tttgtttttg agacggagtc ttgctctgtc    15480
```

```
gcccagtggt atgatctcgg ctcatcgcaa cctctgcctc ccgggttcaa gcaattctct   15540
tgcctcagcc tcctgagtag ctgggattac aagcacacac caccatgcct ggctaatttt   15600
ttttgtattt tagtagagac ggggttttgc catgttggcc aggctggtct cgagctcctg   15660
acctcaggtg atctgcctgc ctcggcctcc caaaatgatt acaggtgtga gccactatgc   15720
cctgccggca actgtaaatc ttaaaacttg caggttctgt ctctctctct ctctgttttt   15780
tttgtttgtt tgtttggggg ggggtccttg ttttgtattt actgaagaaa ccggattatt   15840
gttttgtaga gtttacccaa gtccaaattt tgctgattat gccatgatat ggcttaatat   15900 tttttctct ttatttcta taaactggta gcgagagctg gaagcttgcc ttgatgaggt   15960
tagggttggt tattcttggc aagataactc tagagatgag ggtgttttc cgtcaggagg   16020 cacttgacat ctggttgact cctgttgttt tggctgcta ttgatgctca ttggccagat   16080
ctgtccattt tctagggagc tacaaaatgc tgatatttta attctattac ttcttgcatt   16140
agctgaaata gatctttaaa aagaaacttt tcctcctcta ctatttagtt accaaatagg   16200
cagaataaat gctttatctt tccttttatt taccagtttc cagaataaca agctggttcc   16260
gtagcattct ttaccagtga ccaacagagc atacattgaa aatttttaca gtgaggatag   16320
agcctatcaa tagaagctgt catggagttg aatagggtca tggggcttgc agacatttgg   16380
aacagtgttt cccaaacttc cttgaccaca gagtccttta aaacgtataa gacattcccc   16440
cagaggagca caagagcaga gactaaagga actccatcca catctctcca tttctctgtt   16500
gtcctctccc attctctcgt cacaatccct tctctcccttcccacctcac ttccccatcc   16560 ccctcctcac ccctacaact cttcagccat tgctctgga aagggtcaaa actaaacagc   16620
ccatcttgaa ctgaccttgg ttccctcctc attgagttct aattaattat ctctggccag   16680
gatttaagtc aatagccaat taaaagttta ttctcatgac attattaaaa tttgatcctg   16740
aagttttaat ttttccattt taaagatagg attgcagttt ttaaggactg ggaaaaaaaa   16800
gttctcatat gtgctgcata ttagtgcttt acattcttca cattatttc tcaaagggtt   16860 tatgattgag aacttattta gtagataccg gggcagggta ccaaccatga ccacctcatc   16920
tgattgagca cattggctaa atctaaacta ataagtattc aactttacat atgatcatta   16980
ttttacttcc ccaaattcct ttgcagatga gacaaacaga tcgggatgta ataacagcat   17040
taactcacag accttggagc ctaagccata caggagatgg gaaaccacgc tatgatactt   17100
tctggaaaca ttttatattt gttatgatgg acattttgct cgattggagc atgcataata   17160
tcttgtggta cctgtgtgga atttcagctt tcctcatgca aaaggatttt gtatccccgt   17220
aagttggaag gttttttatt ttacccagac agacatcctg aatgctctta tttgaaagga   17280
aggattaaca gagtagacaa cctgaattgg ttctgacctg caaagcttac catacctcta   17340
aattggatta ccaatttcgc ttcttaggtg ggaagagttc aggcatattt cactgttttc   17400
agaccgagtc gatcacatat tttcggtttt ttagtgtatt ttgaagaaaa aaaatgaacc   17460
tgtgacacta tgctgagcaa gggatttat ttctgtgact ggtttttttg aaagccaaca   17520
caggatcctg ggcagaacca cagtgaagac atcctgtggg caccagcctc cccactaccg   17580
tcttatgtta taggcactcc cccacctctc cccataaaat ttccatttcc taacctgcta   17640
gcgatctcgg aatcatttct ttggcaattc tgtatctgta tatttcagct aattagagtt   17700
gtaggtctag tattatttca gacatacatg attcagttca ataaatattt ggtaagtgcc   17760
tatactattg caaggttcca tgttgagaag ctgaagatgc agtgggtaaa gaatcaaagc   17820
catgatctct gccctcgtga cgtttatagc caagtgggag agtgagagat gctaatcaaa   17880
```

```
taaaaatcca atcaatataa agttaaaact aagatacagg ctatgtcaga gaaaactgtg   17940
catgggctat aatctaatct ggtctgggtt gtcagaaaca gcatcccccaa ggaagtgaca   18000 gttaagctaa gatctgaagg gtgagtggga attgggagga atccagatca gagagaaaaa   18060
tacatgtaat gtgctctggc aggaaggaac atggttcttt ccaggaagtg aaagaaaatt   18120
aatattcttt caattaattt aaaattaatc agcacagaaa agaaaggggg aatgtggtgt   18180
gagatgaagc caaggagaca ggtcggggcc aggtcaggca caccttcagt ggctgtgcca   18240
aggacatttg ggggtggcga tcattagtga gctactgaaa tgttttaagc tgggacagtg   18300
tagaggaggt tcatggcatc ctgggttttg aacagtccc tctgatcaca gtgcagaggc   18360
cagttaggag gcattctctg ggcaccattg gtatgcagtg aacaccatac ttagtggcca   18420
ttatggattc ctgagacagc tgcttattat tctaacagga ttggctttcc tcttccccca   18480
gggcctactt gaagaagtgg tcagctaaag gaatccaggt tgttggttgg actgttaata   18540
cctttgatga aaagagttac tacgaatccc atcttggttc cagctatatc actgacagca   18600
tggtagaaga ctgcgaacct cacttctaga cttcacggt gggacgaaac gggttcagaa   18660
actgccaggg gcctcataca gggatatcaa aataccctt tgctagccc aggccctggg   18720 gaatcaggtg actcacacaa atgcaatagt tggtcactgc attttaccct gaaccaaagc   18780
taaacccggt gttgccacca tgcaccatgg catgccagag ttcaacactg ttgctcttga   18840
aaatctgggt ctgaaaaaac gcacaagagc ccctgccctg ccctagctga ggcacacagg   18900
gagacccagt gaggataagc acagattgaa ttgtacagtt tgcagatgca gatgtaaatg   18960
catgggacat gcatgataac tcagagttga cattttaaaa cttgccacac ttatttcaaa   19020
tatttgtact cagctatgtt aacatgtact gtagacatca aacttgtggc catactaata   19080
aaattattaa aaggagcact aaaggaaaac tgtgtgccaa gcatcatatc ctaaggcata   19140
cggaatttgg ggaagccacc atgcaatcca gtgaggcttc agtgtacagc aaccaaaatg   19200
gtagggaggt cttgaagcca atgagggatt tatagcatct tgaatagaga gctgcaaacc   19260 accaggggc agagttgcat ttttccaggc tttttaggaa gctctgcaac agatgtgatc   19320
tgatcatagg caattagaac tggaagaaac ttccaaaaat atctaggttt gtcctcattt   19380
tacaaatgag gaaactaaac tctgtggaag ggaagggggtt gcctcaaaag tcacagctta   19440
gctgggcaca gtggctcatg ccgataatcc cagcaattca gaaagctgag gcaggaggat   19500
tacttgaggc cagactgggc aatatagcaa gaccccatct ctaaaaaatt aggcatggtg   19560
gtgcatgcct gtattcccag ctactcagga ggttgaggtg ggaggatcac ttgagcccag   19620
aagttcaagg ctgcaatgag ccatgattac accacggcac tacaaccttg gtggcacagt   19680
gagaacctga ctcttaaaaa aaaaaaaaaa aaaaaaaaaa aaaagataac tagaacttct   19740
agaacatctt gtttacagtt agccagaaac tatacaagtg gtttaacatg cattatctta   19800
ctcaatccat acaaaagtct tatggagtg ttagcactct ttctactgat gaagaactga   19860
ggtacttcat aaaaccactt acccaaggtg tcttgagtct ggtacaactg gcattcaaat   19920
ctaggtcagt ctgccccag agccactacc cttacccctc actgaatctg cctttatatt   19980
gttgagccca tgaccccaaa ctgctctttc caatttgaac ttccagggat tttattgtga   20040
acttacatag caacattaaa atgaagttga attgttttta atggcaacgc cgtctgtctc   20100
ctctagctta ccgcttctca cctttcaacc ccatctgtgg cctttgtcca ggcccacagc   20160
ttagccatgg cttccctcct gcatccctgc cgtgggttgc tggcctcaca cttgcagcag   20220
```

```
ctggacagtg attttagaag gccaccagtc cccatagcta tgtgacaatg agaagcaaac    20280 tttttttgtga cagattgtat tggcataggc atgatagatg gggattggta cgttttgaat   20340
cagcatttgc aaaaaaattg tcttgaattt taaaataaac aacaaagatt tgttcattga    20400
gtgcaa                                                               20406
```

<210> SEQ ID NO 6
<211> LENGTH: 48569
<212> TYPE: DNA
<213> ORGANISM: Homo sapiens

<400> SEQUENCE: 6

```
gcactccact gaccgtcccg acgatgctac gcgcgcccgg ctgcctcctc cggacctccg      60
tagcgcctgc cgcggccctg gctgcggcgc tgctctcgtc gcttgcgcgc tgctctcttc     120
tagagccgag ggaccccggtg gcctcgtcgc tcagccccta tttcggcacc aagactcgct    180
acgaggatgt caaccccgtg ctattgtcgg gccccgaggc tccgtggcgg gaccctgagc    240
tgctggaggg gacctgcacc ccggtgcagc tggtcgccct cattcgccac ggcacccgct    300
accccacggt caaacagatc cgcaagctga ggcagctgca cgggttgctg caggcccgcg   360
ggtccaggga tggcggggct agtagtaccg gcagccgcga cctgggtgca gcgctggccg    420
actggccttt gtggtacgcg gactggatgg acgggcagct agtagagaag ggacggcagg    480
atatgcgaca gctggcgctg cgtctggcct cgctcttccc ggcccttttc agccgtgaga    540
actacggccg cctgcggctc atcaccagtt ccaagcaccg ctgcatggat agcagcgccg    600
ccttcctgca ggggctgtgg cagcactacc accctggctt gccgccgccg gacgtcgcag    660 gtgaccccc gggcggcccg tgtgctgtcc cggtcctccc acccgccctg gatgctctcc      720
cgcctccccc agaccctggg cttttccgat gcccccagt tctctttcct cttttcccaa     780
gccatcatcc ctcgggctac gtcctccctg tcgagggata ttacagactt ggctatctct    840 tttttcccctt acacgtatgt tcatttatta attcatcagg tgtaaattca gcaccttgta   900
ctcgctgcct gctttagtag agttggggat ccaacaggaa aggggacaga cgaggtctcc    960 cgcaatttt gcgctcccgt tcccaaactg aattgcccct tcgagcgcca acccatccct    1020
tcccccttcc ctggcgtcta gtttcacaat tgggcgcacg ttttaaaaaa cagaatctag   1080 aatttttcttc ctcgggctttt gcttccgata ctagttttttc cttctttctt tttttttttt  1140
tttaaactca tcatcttttt cagatgacag ttttagacct acaccctgtt ttaggaacct    1200
gatctcaagc ctttgtgtcc tccttttttc ttctgttttg ttcatgtttt tactgtagcg    1260
ttcccatcgt tgtagctgtg gtccgtggtc acaagcagta caactcatt tattccatta     1320 attcactttt ttcgaaattt gagaaatcat ctagtaaggc cccgttattt cacaggtgaa    1380
gaacccgagc ccaagagtat gccttcttaa ttgtctttct ctaaggtcta gtatccaagt    1440
cttctgtttt cctagaatgg ttctttttct cttagaaaat gttgtaatag ttacaaataa    1500
taatgatagc atacacctca tgcctattgt atgccaggta tgcctcacat ttatttttaca   1560 aaatccttac aaccacaatc tggagttgat agtatttttcc ccttatctca aagatgagga   1620
aattgataca cgaacacatt aaataatttg cccattttca tacagctagc tgtgaccca     1680 ggaaatctga ttcagagctt gctttcttag ccattatgct atactgcctc catttgtcca   1740
ataacatacc taataagaat aaaaacatgt aacattttttg taccacagag atgagcaagc    1800
attaatagtt tcttgatcac tttaaggcc agaattgaag tgaggattat tgtttagctt     1860
caaagcccaa gtgaaaaatt agaagtaggc tggtttgtaa tttcttctgt agctgttgaa    1920
```

```
cagtgaaacc atctgtaagg gatttctcca ctgattctgt gtcatgttat tgtgggtaat   1980
tcagttagct gacttgtgtc taattacttg ttgaactgtg tttttttta aatatatact   2040 ttttccatta gcatgagtga aaattcctca taaatctgtt aaattaacag aatggtgaaa   2100
gcagaacata ttttaatata acacaatatc tatagcgact tcctggaaca agtgaatttt   2160
tgttctcaga tggcattgcg aagactggca tttgactctc agtacagagc cagggatgaa   2220
aatactacag ttcagaataa gcccactcct gaccgttttc agtgtcagat agcaaaccct   2280
ttgcctagcc actttattat tctctataga caatagtttt gcctattatg tacatctggt   2340
cttttgaggg agtctgctga attagatttg tagttttgta gaaacagaac aatgcctttg   2400
tttttgttta aagactagca ataattagat agtaacaagg ataaaatacc cagatgcact   2460
tgggaaatta tattttagtg tacacagaaa aaaggtgaca aagttcgctt attttcctag   2520
tcaagatatt ttcttaagaa ttgcaatcca gttgacaaag tgggcagaat tatccatttc   2580
aagagaaaca aacatacata ctgattttt ttgcatacac atccaaagcc cagataaaac   2640
tatattcaat tttctcatat tttatgtaca aaatgatat acttggtgtt cttttcgtgg   2700
taaattgttg gagaaatgat tgaaaaatgt gtgttttgaa tatgactgaa aaaaacgtaa   2760
agggcacacc agtagttgaa gcatgattat gaatgcttct ccaatacata tttgttgccc   2820 aattggggggc ataatgtaat ttattaaatt ttatatagaa agttatctgg ggcttcagtt   2880
aaaagataaa ccaattcaca ggcccagcac agtgaagcac aggagaccca aaacatcagt   2940
gcgttttgtg ctgctgtcag tagttttttgt ccaaagcaga atctttgtaa agtaatacag   3000
agttgggaag gttaattgag aaaataaaat actctgttta gactttggct tagagtgaaa   3060
aaatagattc catatgttga attctctctc accttgtaag tagaaacttt gctgatttt   3120 agtttgcttt ctaaagttt ccgtgcctga cagaaacagt acttattaat gtatgatgca   3180
atttcattgc gtagcatctc tacaacacat ttaatcttca atctctattt ctttagcctt   3240
ttctagctat tctcatgcgt tacagccatt ataaatgggg aataattta ccccaagagt   3300 ttcctgacca atatgtgctt atttcagctg tgcggattag taagatgtta gtgttccttt   3360
ttcacactta acatttcaa taatttgaaa ctgtcattta tgtcagtgat ttacaaatac   3420
atataaattt ttttctcttt cagatatgga gtttggacct ccaacagtta atgataaact   3480
aatgagattt tttgatcact gtgagaagtt tttaactgaa gtagaaaaaa atgctacagc   3540
tctttatcac gtggaagcct tcaaaactgg accagaaatg cagaacattt taaaaaagt   3600 tgcagctact ttgcaagtgc cagtaaatga tttaaatgca ggtaatatgt ctgttgtctt   3660
ttatttgaac ttaacagttt aaataatttt gaactgtgaa aatgaaaaca taaggaaaca   3720
gtctttttta aagacccata attgatctac attaagaaaa taatatgttc tgggtcaaaa   3780
aaattgtata ccttgtgctt actatttacc attttagat tcatattctt ctttgagtgt   3840
tatttaaatt actgtacaag attctagtta tattctggag tttttttgag ggcagagtaa   3900
tataaagcct caactgtagg cattattttt aaaacaaatt atcttttctg aatttccccc   3960
tgataaagtg atacaaatgg aaaaatcata taaattcttt agcttttgaa gcagttcaaa   4020
agtacctgtt aatgtgtaag aggggtaagt tttagaaagt gaaaagcaaa gtactatgat   4080 gtttttttgag ttatatgtag caatgctgag aagatgagca gtcatgtcta tcataagtta   4140
ttgcagtgga tgggctgact atgcaactta ccatccaaac tggtgggaca ctttcgaaag   4200
tgaaagggaa cactattaat aattttgcca ggaaagcagg tgggaaacca tggcacatgg   4260
```

```
tcacctagca atgggagatt aagaaaataa gatttttttc tgttttctag gaatttatgt    4320
tccatagggt agatgttgac aaagatacat gcaaagattg tagattacat tatactctga    4380
attaatttcc aaaagactgg aagtagatgt tggggaaaaa atagattaga atttatcagt    4440
cacagggcct ggatgcttta taaggatcaa aaagaagatg cctagactag catttgaaat    4500 tgaattttt  ctctctctcc aaactggcag tacattggca tcgcctgtgg agctttaaaa    4560
attatttact ttattgggaa ataattcaaa cacgaagata acaaaaaagg ctaatgtggt    4620
gaacatccct atacccacaa cttggtttta ctaaatttta actttgtgct tcagttactt    4680
gccttaaata aattgaggtc tactggtccc tttcctggat cccattcttc ttcctttctc    4740
accagtggta attgttgtca tgaattgagc atttatatta tcccatgcca gttttataca    4800
taaatgggat attgttttgc agattttaaa acttttaaga gtggtatcaa agtttatacc    4860
agtccaaaat tctatttta  tgcaactttt tgttttgat  gtaatgtttg caattctagt    4920
cctacatttt aaatgtatgt atttcattct acatctatac caatatctag ccattattct    4980
gttagtaggc agtaggttg  ttgaaaaaga tttttaaaa  ctatgtttag tctctgaatg    5040
ggcaagaatt atgtatttta ctgatgaagt aactgacagc aacttctttt tggaagcagt    5100
attaagtata gtggttaaaa taatggattc tggaattgga ctatttgcat ttgaatcttg    5160
actctactat cctattgaat aactatgatt tttgacaagt ttattaatgt ctttatgcca    5220
cagtttcctt ttctgtaaaa tgaacatggg aattattctt gtcttatagg attattgcaa    5280
agattatata agattaattc atacaaagca tttagtacct ggcgcagtaa ttgcgcaata    5340
aatacttttg ctatttaaat accctttgt  ttacataggg ggtgatgcta tatgtatttt    5400
cagtaactta ctattttac  ttaacaatat atttgtctct agacaaatat agaactgtct    5460
cattctttta aatcctgtgt atttcatgg  gacatatgaa tgactcgatt tgtaagtcaa    5520
tgctagttaa attgtttaac ccatcatcga attttactgc tgtaagaggc tgttgctaat    5580
gcagtccaaa ttctttttat agaaaccatt ttcctactga gttttttctt agttttaac    5640 tctttcaggt aatgctacag tgaacattct tgtagtctgt tttttacact tgagagttta    5700
tttgtaagat aaaataggtg aggccgagtg ccgtggcata acctataatc ccagcacttt    5760
gggaggccaa ggtgggtgga tcactggagc ccaggagttc aagaccagcc ttggcaacat    5820
ggtgaaaccc tgcctctatc aaagacacaa aagttagcca gtcttataac ttggtctcca    5880
aataaataaa tagatttcta aaaatgtttt ttaaagataa ataggtgaaa ttgctgggtt    5940
aacacacatg aatattttac atcttgacat atatttttaa attgttctct gaaggtgtag    6000
taaaaattta tatccacagt atatgagaat gttcattttc ccatatcttc caacagtaga    6060
tattattagt catttaatt  ttcgccaatt tgattaatga aaaatagtat ctagctttaa    6120
tttgcagttc tttgattact tctgaaagtg aacatatttt catgtttagt agccatttgc    6180
atttcttcta aaaattaccc cttcataatt tgttcatttt tctattgggt tattttttgtt   6240 ttcttatgaa tcacaaatac cttttatgta ttatggatat attaattata tcttttaatt   6300
ctgcctgaca aaggattcgc cctttgcttg ttgtatgttg ctaatatttt aatttcttgc    6360
ttatctctta ggtttgttga tggtgccttt gattgcacag aagtttacat cttttacata    6420
gccatatctg tctcttcatt atggcttctg agtgttgtat tttgtctagg aatcctccca    6480
ccgcaagatt attatgtttt cctattgtct tccttttttg ttgttttatt ttttctcag    6540 gggagtggag ggaaagggtc tatttcgttt tttaaatatt taaatttctt atccacctga    6600 aatattttg  aggttctgaa agattgacca cgaaatcaga agggtcataa cagataagtc    6660
```

```
agagctataa cttaaataag atagtgtatc taacctctttt actttgtaag tggggaaatt    6720
gacactaaag agagcttacc caggataatt agtggtaaag tcaggtctca gcctgtcttc    6780
atctgatgct ttttctccct gtactctgaa gagtttttg gtgaattttt tttttctggt    6840
aaactctctt ccggtttaag aatataccat gtggactgac ttcatagttt cagaattaga    6900
gcttcgagtg taaataagcc aggtcctttc atcaaatgta cctggtactt acaagccact    6960
atattgtatc aggtattgag attataaaac cttttcttta cgtaagcaaa gttttgaatg    7020
gcttttctgt atattcccaa tgaaatacat ttttttgta ttatatactg cctcaggaat    7080
tctttaaact cagaactagt gcaaaatgca tgtaacgcca gttgatttt ggtcccattt    7140 tcctttagga aaacaggaaa ggcagtaaaa ttaagaaaa atcaaagcaa tggaggcaac    7200
cactgcagtt gactttttt tctctctagc attaaatatc acccacttct cattgactag    7260
agagcagcag tgtttttatt tactaacaaa ggctactttt tatagcccaa gcattcattc    7320
ccttatcact tctcttcaat acccatatgt atctcaaagt aatgtaatca gcaaattagc    7380
agtgtaaaaa tgctagataa cttattctga aatccacttc cgaaatcatt tgagcagcta    7440
agtttgaaaa actcatgttg gtaccaacat ttctctcttt agtgtgtgat ttttcccttt    7500
ttgtgcttct cctccttggc tgtctctcct ttctccttcc ccctcactta ccttgcactt    7560
ccttccctct ccatctctgt agtcttctct ctccttttat atcttttctg tacttactgc    7620
tgcttcttag ttataaaatg aattgtataa tttaaactgt ttaataaatg tactttgtta    7680 tttgtaatttt tcaagtcggg tactaaaacc tttataacct tagcccccct ccttgaaccc    7740
tctaaaatta acaaaatcat attaagtttt atatagcaag tccttgggtt atacttttg    7800 ttgatattgc taggcaaata tgctcttaac aagtaattgc ctgaggcagg aggattgctt    7860
gagcccagga atccgagttt gcagtgagct gtgatcacca ctgcactcta gcctggacaa    7920
cagagcaaga ccctgtccaa aaaaaaagg cagaaaaag ttaccaatta cagaaaattt    7980 cttagttta ttgggctgaa atttatactt cctcatggtt tcttcctgat agttcagttc    8040 tgcacccta aattacacag agaaagtctc ttaattcttt gatagccagg aagaaactaa    8100
attatttctt ccccaaactg aagatgtcca ttttattgag ctgtaccaca catggcattc    8160
tacagatatt tagcctttga aaaattgcag aaaataatga cccacaaaat tttaccttt    8220 tttcccccca gatttaattc aagtagcctt tttcacctgt tcatttgacc tggcaattaa    8280
aggtgttaaa tctccttggt gtgatgtttt tgacatagat gatgcaaagg taagtattat    8340
ttttgcagtt tctttgcttt tttaaaaaaa ttttttttgg cttgcttgtt tgcatttggt    8400
tacttgaagc agcttttcag aaaatgagta gttagggaac ataaactgtt ttgtgactaa    8460
ctcctaattt tccttaaata aagagagatt aaaggttcaa attggtccca cctacttgta    8520
aatagtttag gttcaaaaaa ctctggaaac atttttttcca tgatgatttg atttctaaat    8580
catcccattt acagacctac ttttaaccca tcatcaaatt ttactgcttg gagggatta    8640 tagagctgat ataatcccag attcttttta tgggaagcca aagctcagag agaataaatg    8700
ggtttccaaa gtcctagcaa ctattttata acagttttca tgggaaattg tgttctgtgt    8760
tttacagtga acacttgtat gtccttcacc tatatttacc agttaacctt ttttgccaca    8820
tttcctttat cactctctct actatattag tttcctattg gtgctctaac aagttaccac    8880
aaacttactg gcttaaaaca atataagttt attatcttat ggttctggag gtcagaagtt    8940
caaattgaat cttacagggc tgaaatcaag gtatcaatag agccgtatac aatagagccg    9000
```

-continued

```
tattctttca gggggcttta ggagaacatc tgtaccctgc tttttctgat ctccagaggc   9060
tgcttgcatt tcctatcact cagacttctg acgggtacat ctccagctct aactgtcctt   9120
cctgcctgcc tctcgtaagg atacttgttg attacactgg gcccacctag atagtccagg   9180
atttatctct ccatctcgag attcataagt taatcacact ggcagattcc cttttatcag   9240
gtaaggtaac atattcatag gatgtcaggg attagaatgt ggacatatgg gagctgtttt   9300
ttctgtctac cgtgtgtata taatcttttt ttccccgccc caccatcagg atgcttcacc   9360
cttaaatact tgggcatgca tctaggacaa gaacattctt ttgtataacc acaatacaga   9420
atactatagt tcatatttat gtatatcata tatatcacaa tattttctaa tgtacagtca   9480
actttcaaat tttcacgtct taagtctttt atagctgttt tttgtttgct ttgttttata   9540
agattcagga tctaataagg gatcattcat tgcatttggt tgcatttctt ttagtctcgt   9600
ttaacctgaa agagtgctcc agcctttctt ttgtccttcg tacattggcg ttttggaaga   9660
gtctaggcca ggttttttgc agaatgtttt tggatgtgtc tgatattttt tactcaggat   9720
tagattcaga ttaaacattt ttgacaagag cactacgtaa gtgatatatc cttctcagtg   9780
catcatatca gaaggactga tgtctgcttg tcatgtcatt gattattatt actatttttt   9840
tgagacagtg tctctctctg ttgcccaggc tggagtgcag tggcgcaatc tcagctaact   9900
gaaacctctg cctcccggat tcaagtgatt ttcctgcctc agcctctcca gtagctggga   9960
ttacaggcgt gtgctaccat gcccaggtaa ttttttttatt tttagtagag atggggtttc   10020
accatgttag ccaggctgat cttgaactcc tgaccttagg tgatctgccc gcctggccc   10080 cccaaagtgc tggtattaca ggcatcagcc accactcctg gccagtgatg tttgatcatt   10140
agattacaat ggtgcctgcc tgatttcttt attgtagagg tacttttttt ccttgtaaat   10200
aaagaacttc ttggccgggc gtggtggttc atgcctgtaa tcccagcact ttgggcggcc   10260
aaggcgggtg gatcacctga ggttaggagt tcgagaccag cctggccaat gtggtgaaac   10320
cccgtccata ctaaaaatta aaaaattagc caagcgtggt ggtgcacacc tgtgatccca   10380
gctactcggg aggctgaagc aggagaatcg cttgaaccca ggaggtggag gttgcagtga   10440
gccaagattg tgccactgca ttccagcctg ggcaacaaag caagactctg tctcagaaaa   10500
aaaaggaaaa aaggaaaaaa aagaacttct aatttaaatg actgtgactt gaaaatttaa   10560
atacatgttt attaaattaa ttgaataata gtttcttttt acatgtgaaa agaaattaaa   10620
ttcttctttt aaaaattaag gttgtctttt gattgaggta ttttctatta tttacttcag   10680
caatttgtta gaaaataatt tatccctgct taggactttc actgtgaaat aggtttatat   10740
gctgaagtat ttacaggtga aataaaatga tacctgggat ttgcttcaaa ataatacagt   10800
ggtggtggta ggagcaaagc tgaaatggga ttggttgaat gttgattatt gttgaagttg   10860
gatgagtaca cagaggttcg ttatactact gttttatatt tttatgtgt ttaaagttct   10920 ttgttaagaa ttttttttt tttttttttt ttttgagaca gagtcttcct ctgtcgccca   10980
ggctggagtg cagtggccca atctcagctc actgcaacct ctgcctcttg cgttcaagca   11040
gtcctcctgc ctcagcctcc ccagtagctg ggattacagg catgtgccat catgcccggc   11100
taatgtttgt attttagta gagacggggt ttcaccatgt tggccaggct ggtctcgaac   11160
tcctgaactc aagtgatccg cccgcctcac cctcccaaag tgctgggttt acaggtgtga   11220
gccaccgcac ctggccaaga atgttttta caattaaaaa ttaatagaca tttatgaaat   11280
tctgagataa ttagatatcc tggactttgt gtaccttcag caagcatttt ttgagtttcc   11340
gttctgtgac aagcacttgc ttggaactaa agacactaac ataagataga tattgtcctc   11400
```

```
aaagaatgcc acaaggaatg aaagacatgt aactaaacca ttgcaagaca ataggatgtc   11460
tatacagtga tagaagtata ctcagatgct ccttaagtta tggtggggtt gcatccagat   11520
aaacccatgg tagattgaat atcttaagtt ggaagtacat ttacgactta caatggattt   11580
atccagacat agcctcgttg taagtcaagg agcgcactga aagtgtattg cttttgaacc   11640
attgtaaagt tgaaaaattt taagtcaaac catcataagt tgcagactgc ccatgaaagg   11700
tgtagtgggg cacaaaggag aaagttaatt tgtaggatag cttttttgca atttgtgtct   11760
gctttaataa gtatatctag attttctctc tcctgggatt agttttggta tttaatatac   11820
ctataaaagt catttatgtt atccattatt tgctgaatta agcaaatata tcttttgatt   11880
ttaaaaagtg ttttccttct ctgaaattat ttctccgtaa ttgtgtattt ttgctttcaa   11940
ttttttcttt attacagtag tttattgttt actaatttat ttttcccta agaaacagtt    12000 tagctttatc tgttttttgaa ctttataatg atggaattac tcagcgtgtg tttttttttct 12060 tttggtatct agctcttgtt caacattaag ttttttaagat ttatttggga gctaaatggt  12120
gagaacacat ggacagatag aggggaacaa catacactgg ggccttttcag agggcagagg  12180 atgggaagag agagaggatc aggaaaaaata actaatgggc actaggatta ataactgggt  12240
aatgaagtaa tccatacaac aaactcccac gacacaagtt aaaaaaaaag cttcccattt   12300
atagattgct acttagaagg cagggatttg aactgggagg aatttaaaat gatcttgacc   12360
tgttgtgttg tgaaaaggtt tacaaatttc aggaaaatat acctcttctc aaatggattg   12420
ggaattatga ggtcacagac atttctcagg attccgtaaa acatgtacct gtagcagagt   12480
attagaggag attgaagcaa aggggcaagc ggtaacttct tgggggcgat taagtcattg    12540
tattatcatg gtgggggcag gttatacagt tgtttatatt tgtcgaaagt catcagcctg   12600
tatatttaaa tcatgtgtat gtaaattaca atttaataaa gttttaaaaa tgaaaaaaga   12660
tttatgaggt tgcatatagc tacaattttt aattttcatt actgtataat attccattat   12720
atgaatattt tacagtttat tcattatctt ttcagtagac attgttttta gtttggggct   12780
attatgaacc ttgttgctat gaacattatt gtatatgttt attggggtac aggtatacct   12840
gtttctgaag gtgtatgtct ggtagaatta tcgattctca tgcttcagcc tcctgagtag   12900
ctgggaccac aggcatccgc caccacacct ggctaatttt tgtattttta gtagagacgg   12960
ggttttgcca tgttggccag gctggtcttg aactcttgac ctcaagggag ccacttgcct   13020
cagcctccca aactgttggg attacaggtg tgagccactg cacctggcct tttttttttt   13080
tttttgagac agagtcttgc tctgtcaccc aggctggagt acagaggcgt gatctcggct   13140
cactgcaagc tccacctccc gggttcaagc cattctgctg cctcagcctc ccgagcagct   13200
gggattacag gcaccgcca ccacacccgg ctaatttttt tgttttag tagagacggg     13260 gtttcaccct gttagccagg atggtctcga tctcctgacc tcgcaatccg cctgtctcag   13320
cctcccaaag tgctgggatt acaggcgtga gccaccgcac ccggcccttt ttttttttta   13380
aatataaagt tttagtggta agcatgtgag aatttttaa atctccagtt gcctcctttt    13440
tatttctaat agtagatttt attatttgaa tagattgaac agactattat ctaattcctt   13500
tttaaatttc ttagtgttta cgtctctttg ttaacttctt gatttcattg cctttgtgta   13560
aggacagact ctctcaagcc gtgttttttcc tttactctca caccaccatc acaatcatca   13620
acacagaaga cttctgtgac caaatgtgtg ggagcctttc ccctgcacgc caagcaggag   13680
acaccagctg ggtgtcctcc agttcagatt tgacattgtc tacctggagg tagtattaga   13740
```

```
tcccacaggt tgagggctca gtccccaagt gccccatcgg tactcttctg ttcagctggc   13800
ttcaagttgg cgttcccatg acctcttctt tgggttcagt taatttgctg tagcagctca   13860
cagaactcaa ggaaacactt ttgctggttt attataaagg atgttacaaa ggatacagat   13920
gaagagatga gtagggcgag atatggggga aggggcgtgg agcttccatg tcctccctgg   13980
gcatgccacc ctccaggaag ctccacatgt tcagctatct gtaagctctc taaacccagt   14040
cctcttgggt ttttatggaa gtattccttc cccccaggat atgaggcagg acccttcag    14100 ggcaggatct taagaccccc agaaaggcag gaagattaga gttctgcctc cgcacaggtg   14160
aaagggaggc aggagagaga ttctgtttcc tgaggcctgc cctggaggcc taacacaccc   14220
agcattatac caaaagacta caacaaggga tatgggagtt acaaaccagg aagtgtggac   14280
gaaagccaat atatacatat cataatacca caggtcagcc cctggttttc gaagagggat   14340
accttacatc aaaagaatat atacaatcat taataatcca gtccatcatc tgtatgaatg   14400
tcttccaggg caaggccact caggtttgcc agcttccttt caatcctgtc aggttccaaa   14460
accaggagtg gtcttggcaa atttatggct tcaccctttc atgcatctgt catacttgag   14520
ctaagagaca gcgtcacctt ttgctctgag ccccgttcaa ggcgttcatg taatatgtca   14580
tttccttcaa tttataaccc gtttattcat ccttttttccc tcagctgttc tccttttctt   14640
cattaataaa tatctacact gctacctttg gaagggacac aagttgccat tgtgctgtgc   14700
tagtctagat tgtaggcagc aatgctagtg tagcaagtag ctcctcctca cccctttaat   14760
gtattttttg ttttgttttt atatatggca ctgacccacc cctgctctta aaacttacta   14820
tgacatgcac ttagtttctc taggagctct ttcgggaaga aaggtttgtg actattgtag   14880
tcatcttgaa cctcttttgg gttacatatt ttagtcccct agttgtggtt ttagctacag   14940
gttttagttc tagatagaga tttcagttct ccacttctac atgagcaaat gatcaaatga   15000
tatgtaagtg gaaaatttaa ccctcagata aaggctactt aattaccagc tcccggttcc   15060 agaccttttca gcagaggtta ataactgtaa tcagtgatag gtaggtttca aaccgttttc   15120 tatacttttta taatctgtat cattcttaga aatataaaag gtatagtgtg tgtgtgtgtg   15180
tgtgtgttgg taataaatgg tattataggg tatgtattat ttttaatggg ttcttattca   15240
acattgtgtc ttggagattt ttccatgtca gtacatggaa atctataata tagaacttt    15300 tgataactgc aaagtattct gaagtatgtg tataccatag tttatttaac catctaccta   15360
ctattggaat ttagttgttt ctggggattt tttggcttct ataagcagtg ctactataag   15420
tcattcttgt acattctccc tggtgttcct ctgtgaatat cactttataa gaaatggaat   15480
taaatgggtc atagggtatg tgtgttttca tggattttgc caatttgccc tctagaatgt   15540
ctataccaat atacattcct tccaacagta cccatttccc catatccttg gtacactttt   15600
attattattt tttcaccaaa cagatacatg aaccaaagta actcattttc tatttgactt   15660
ctaccttctc aaaattctta tacatttctc atccacctat ggtatctttc tgtgctttaa   15720
tgaatattct tcttctttat tctttcttct aaatgtatcc ttgacattta gaagaaagaa   15780
taaagaagaa tattaatata atatcatctt aatataatgt tagaagaaag gagaggtgag   15840
cacatgtcct tactccactc tcttgagctg tcctgacctt ggatgattgg ctgtgagcac   15900
ttactggctt gctcttgcac accagcatct acattccccc aatccaaatt tgtgatgcag   15960
cataaatctc tctgtggtat gaaccttagg gaccaactct taaatgctgg aaaggacaaa   16020
tactatattt tgtgcagaat ggtaattaaa cattgtaacc atttcttaga gaatcattat   16080
taaatcaggg aatcttgtta tattttgaa aatatattag aaattatttt tgaatttttt   16140
```

```
taggtattag aatatttaaa tgatctgaaa caatattgga aaagaggata tgggtatact    16200
attaacagtc gatccagctg caccttgttt caggatatct ttcagcactt ggacaaagca    16260
gttgaacaga aacaaaggta agaactttct aaaaaatgtg aagtacattt tgagttacta    16320
ctaaacttct ggaaattttt ttataatgag taattttaaa aaatagtttt tgcttgtgtt    16380
ttaaaaaaat tttaatataa tgtgatacaa aagaattcga taacatatat gtaaattata    16440
aaacatacga accttccact ctacccaaga actagaatat tcataataaa ttgcatttgt    16500
ttacttatgt gttcctcaac tattccattt tcctgcctcc tcttgccctt ccctttcctc    16560
cagaaactat tctttggaat tttgtattgg tcattccttc gcctctttaa aacagtttat    16620
attatgaatg tattggtgcc caaagaatat atttagtttt tcttggaatc atactgctta    16680
ttgtcttttg ggacttgctt tgtttccccc ctcaacttta tgttttttaat attcaacata    16740 ttattgcata tagctgtagt tcattttcac tgtagtacaa tattcaataa tgtgaatata    16800
ccatctactc ttgtcagtgg gcatttagat agttcctatc ttttgctgtt ataattagtg    16860
taattatgaa ctctatgtgg ctcctgctat gaatgtgcaa aatgtttttg ttttgaaaga    16920
gaaaaagctt tgttaacat ttataatctt caattaaaaa taattttca tgacttgaac    16980 ctttgataga acctcaattc caggcttgtt tcaaacttct gggctcaagg aatcctctcc    17040
cgttggtctc ccaaagtgtt gggattacag gcatgagcca ctgcacccag ctgagcacag    17100
agaactttgt aggtggtaga agttttccca aactggattg tggtgattac acagacagct    17160
gtatacattt gttaagatat ctaactcttt aattaaaact gatgaatttc atggtagtta    17220
tgcttcagta aaacttaatc tgagtattta acaaagtgt aaaaaaaaac ggaatgaaat    17280
aattttttgg taaaagtgga aaatttttt ttaaagaaga ctccattttt ctgaattagt    17340
aaagtttttt tttacaaggc aacaccaaaa tgcttatgac ataattactg aaaatgtttt    17400
aaaattatta gatcacttcc ctgcattgat gcgcaatata ttggaaaata attgaatttt    17460
tttaattaag gattttacag tgtcataggg tcattatttt ttaaaacagt ttgagaaata    17520
attcatatgt aggcatgtct caaagatagt gcaagttcaa ttccagacca ctgcaaaaaa    17580
gtgaatatca caatgaaggg agtcacacaa tttttttggt ttcccggtgc atataaaagt    17640
tatgtttata ctataataag tgtgcaatag cattttgtct taaaaaacaa tacatacata    17700 cottaattta aaaatgcttt attactagga aatgcccatg atcatctgag ccttcagaga    17760
gttgtaatct ttttgcaggt gaagggtttt gcctcaggtg ttgaggctgc tgactgatga    17820
gagtggtggt tgctgaaggc tggggtggct gtggcaattt attgtaaaag aaaatatcaa    17880
tgaggtttgc tgcatcagtt gactctttct ttcatgaaag atgtctctgt aacacatgat    17940
gccgtttaat aacattttac ccacagtaga acatatttta aaattggagt caatcctctc    18000
aaagcctgtc actgctttgt cactgtcaca atcctttgtt gtcatttcaa caatattcat    18060
agtatcttca ccaggcgtag atttcatctc aagaaaccac tttgttcatc cataagaagc    18120
aactcctcag gtgttcaagt ttgatcatga tattgcagta attcagtcac atctttgggc    18180
accacttgta attttcttgc tatttccacc acatctgcag ctacttccta tcatccatga    18240
gggttggaat cagcctcttc caaactcctg gtaatgttga tattttgacc tcctcccatg    18300
aattacaaat attcttaatg gcatctagag tggtgaaacc tttctgggag gtttccagtt    18360
tacattcctc agatccatta aaggcatcac tgtctatgac agctatagcc ttatgacatt    18420
tatttcttaa ataaataata tttctctgtc atatgaaatt tctgtttttt tttttgaga    18480
```

```
cagagtctcg ttctgtcacc caggctggag tgcagtggcg tgatctcggc tcattgcaag    18540
ctccgcctcc tgggttcacg ccattctcct gcctcagcct cccgagtagc tgggactaca    18600
ggcacctgcc accacaccca gctaattttt ttttttttt gtattttag tagagatggg      18660
gtttcacctt gttagccagg atggtctcga tctcctgacc ttggatccgc ctgcctcggc    18720
ctcccaagaa atttatttct taaataattt atttcttaaa tatttcttaa atttatttct    18780
taattaattt cttaaaattt ataatgaaat caaaattact acttgatcta tgggatgcag    18840
aatagatttt gttttagcag acatgaaaac aacattaatt tccttgtaca tctccatcag    18900
agctcttgga tgaccaagtg tattgtcaat gagcagtaat attttgaaag gaatctttct    18960
ttctgagcag gaggtctcaa tagtaggctt caaagagcca gtaagccatg ctgtgtaaaa    19020
atagatgtgc tgtcatccag gctttgttgt tctatttata gagcacaggc agaatagatt    19080
tagcataatt cttacgggcc ctagaatttt tggaatgacc agtgagtatt ggcttcaact    19140
tacagtcagg agctgcgtta tctgctaaca agagagtcat cctatccttt gaagccagac    19200
attgatgttc tagatggtat cttcttccaa aagaaggctg ttttgtctac attgaaaatc    19260
tgcttagtat agtgaccttc agttatctta gctagatctt ctggatcact tgcagtttct    19320
acatcaggac ttgctgcttc aacttacatt tttgtgttat ggagatagct ttttccttaa    19380
aaccccatga gctaacctct gccagcttct aacttttctt ttgcagcttc cttacctctt    19440
agcttttcta gaattgagga gagttagagc cttgctgtgg attaggcttt ggctaagggg    19500
aatgttgcag ctgtttggat cttctaccag agcactgaaa cttttcttcct atcagcaata    19560
acattcttcc actttcttat catccatgtg ttcactggag tagcactttt aatttcctcc    19620
aagaactttt ccttttcatt cataacttgg ctaactgacc caagagacct agttttggc     19680
ctgtttcagc ttaggacatg ccttcctcac taagcttaat catatctagc ttttgagtta    19740
aagtgaaaga tgtgtgagtc ttgctttcat ttgaacactt agaggccatt gtaggattat    19800
taattgacgt aatttcagta ttatatctca gggaataggg agactggagg agaggaaaga    19860
ggatggagaa tggctggtcg gtggagcagt cagaacatat acaacattta tcagttaaat    19920
ttaccatctt atatgggtgg ggttcatggc acccaaaac aattacaaaa gtaacataaa      19980
agatcactga tcacagatca ccataacaga tataataatc atagtaataa ttaaaaaaac    20040
tttgaaatat tgtgtattac taaaatgtga tacattacta aaatgtgata cattactaaa    20100
atgtgataca caaaatgagc acgtgctgtt ggaaaaatta cacagatggc cttgcttaac    20160
tcaggattgc cacaaacctt ccatttgtgg caaaatgcag tatctacaaa gcacaataaa    20220
tcaaagcaca agatgaggta atacctgtat catatacagt ttacctactt aaagtgcaca    20280
attcagtgtt ttagtatatt cacagagttg cacaaccatc actactgcaa ctttagaaca    20340
ttttcatcgc ctcaaaaaga aactctatat gctgtgcctt agcagtcact ctccattcac    20400
cctcactctg ccatcccctg gcaaccacta atatattttc tgtctgcatg cattggcata    20460
ttctggacat ttcatataaa tggaatgata taatatgtgg ttctttgtga caggctttta    20520
tgatttagca tcatattttt aaggttcttc catgttgtac atgtagcagt agcatgtatc    20580
attcttttc atggctgaat aatattcctt tgtattacta tatcatgttt ttgttcatct     20640
tatttctttt ttttcacctt ttttaaagtt atacttcaag ttctagggta catgtgcaca    20700
atgtgcaggt ttgttacata tgtatacatg tgccatgctg gtgtgctgca cccattaact    20760
cgtcatttac gttaggtata tctcctaatg ctatcctttc cccctccccc taccccacga    20820
caggcccacg ccatgacagg tgtgtgatgt cccccatgct gtgtcaagtg ctctcattgt    20880
```

```
tcagttccca cctatgagtg aaaacatgca gtgcttggtt ttctgtcctt gcgatagttt   20940
gctcagaatg atggtttcca gcttcatcca tgtgcctaca aaggacatga actcatcctt   21000
ttttatggct gcatagtatt ccatggtgta taagtgccac attttcttaa tccagtctat   21060
cattgatgga catgtgggtt ggttccaagt ctttgctatt gtgaatagtg ccgcaataaa   21120
catacatgtg catgtatctt tatagcagca tgatttataa tcctttgggt atatacccag   21180
taatgggatg gctgggtgaa atggtatttc tagttctaga tccttgagga atcaccacac   21240
tgtcttccac aatggttgaa ctagtttaca gtccaaccaa cagtgtaaaa gtgttctcac   21300
atcctctcca gcacctgttg tttcctgact ttttaatgat tgccattctg actggtgtga   21360
gatggtatct cattgtggtt ttgatttgca tttctctgat ggccagtgat gatgagcatt   21420
ttttcatgtg tctgttggct gcataaatgt cttgttttga aagtgtctg ttcatatcca   21480 cccacttttt gatggggttg tttgattttt tcttgtaaat ttgtttaagt tctttgtaga   21540
ttctggatat tagcccttg tcagatgggg agattgtaaa aattttctcc cattctgtag   21600
gttgcctgtt cactctgatg gtaggttctt ttgccgtgca gaagctctt agtttaatta   21660 gatcccattt gtcaatttg ctttttgttg ccattgcttt tggtgttta atcatgaagt   21720 ccttgcccat gcctatgtcc tgaatagtac tgcctaggtt ttcttctagg ttttttatgg   21780
ttttaagtct aactttaag tctttaaccc atcttgaatt aatttttgta taaggtgtga   21840
ggaagggatc cagtttcagc tttctacata tggctagcca gttttcccag caccatttat   21900 taaatagga atccttccc catttcctgt ttttgtcaga tttgtcaaag atcagatggt   21960
tgtagatgtg tggtattatt tctgagggct ctgttctgtt ccattggtct atatctttgt   22020
tttggtacca gtaccatgct gttttggtta ctgtagactt gtagtgtagt ttgaagtcag   22080
gtagcatgat gcctccagct ttgttctttt ggcttaggat tgtcttggca atgtgggctc   22140
ttttttggtt ccatgcgaac tttaaagtag tttttttccaa ttctgtgaaa aaagtcattg   22200
gtagcttaat gaggatggca ttgaatctat acattacctt gggcagtatg accatttca   22260 ctatattgat tcttcctatc catgagcatg gaatgttctt ccatttgttt gtgttctgtt   22320
ttatttcctt gagcagtggt ttgtagttct ccttgaagag gtccttcaca tccctacaat   22380
tgtgaatggg agttcactca tgatttggct ctatgttgag taggagtggt gagagaaggc   22440
atccctgtct tgtgccagtt ttcaaaggga atgcttccag ttttgccca ttcagtatga   22500 tattggttgt gggtttgtca taaatagctt ttattatttt gagatatgtc ccatcaatac   22560
ctagtttatt gagagttttt agcatgaagg gctgttgaat tttgtcaaag ccctttttctg   22620 catctattga gataatcatg tggttttttc ctttggttct gtttatatga tggattactg   22680
atttattgat ttgcatatat tgaaccagcc ttgcatccca gggatgaagc caacctgatc   22740
atggtggata agctcatcag ggatattggt ctaaaattct ttttttttgt tgtgtctctg   22800
ccaggctttc aggatgatgc tggcctcata aaatgagtta gggaggattc cctctttttc   22860
ttttaactgg aatagtttca gaaggaatgg taccagctcg tctttgtacc tcttgtagaa   22920
tttggctgtg aatccgtctg gtcctggact ttttttggtt ggtaggctat taattattgc   22980
ctcaatttca gagcctgcta ttggtctatt cagggattca ccttcttcct ggtttagtct   23040
tgggagggtg tatgtgtcca ggaatttgtc catttcttct agattttcta gtttgtttgc   23100
gtagagatgt ttatactatt ctctgatgat agttatattt ctgtgggatt ggtggtgata   23160 tccccttat catttttat tgtgtctatt tgattcttct ttcttttctt ctttattagt    23220
```

```
cttgctagca gtctatcagt tttgttgatc ttttcaaaaa cccacctcct agattcactg   23280 atttttttg aagggttttt tgtgtctcta tctccttcag ttctgctctg atcttagcta    23340
tatcttgcct tctgctagct tttgaatgtg tttgctcttg tttctctagt tcttttaatt   23400
gtgatgttag ggtgtcaatt ttagatcttt cctgctttct cttgtgggca tttagtgcta   23460
taaatttccc tgtacaccct gctttaaatg tgtcccagag attctggtat gttgtgtctt   23520
tgttctcatt ggtttcaaag aacatcttta tttctgcctt catttcgtta tgtacccagt   23580
agtcattcag gagcagtttg ttcagtttcc atgtagttga gcggttttga gtgagtttct   23640
taatcctgag ttctagtttg attgcactgt ggtctgagag acagtttgtt ataatttcta   23700 ttctttaca tttgctgagg agtgctttac ttccaactat gtggtcaatt ttggaataag    23760
tgtgatgtgg tgctgagaag aatgtatatt ctgttgattt ggggtggaga gttctgtaga   23820
tgtctattag gtctgcttgg tgcagagctg agttcaattc ctggatatcc ttgttaactt   23880
tctgtttcgt tgatctgtct gatgttgaca gtggggtgtt aaagtctccc gttattattg   23940
tgtgggagtc taagtctctt tgtaggtctc taaggacttg ctttatgaat ctgggtgctc   24000
gtgtattggg tgcatatata tttgggatag ttagctcttc ttgttgaatt gatccctcta   24060
ccgttatgta atggccttct ttgtctcttt tgatctttgc tggtgtaaag tctgttttat   24120
cagagactag gattgcaacc cctgctttt tttgttttcc atttgcttgg tagatcttcc    24180 accatcctt tattttgagc ctatgtgtgt ctctgcacat gagttgtgtc tcctgaatac    24240
agcacactga tgggtcttga ctctttatcc aatttgccag tctgtgtctt ttaattggag   24300
catttagccc atttacattt aaggttaata ttgttatgtg tgaatttgat cgtgtcatta   24360
tgatgttagc tggttttttg ctaattagtt gatgcagttt cttcctagcc tcgatggtct   24420
ttacaatttg gcttgttttt gcagtggctg gtaccggttg ttccttttcca tgtttagtgc   24480 ttccttcagg agctcttgta aggcaggcct ggtggtgaca aaatctttca gcatttgctt   24540
gtctgtaaag gattttattt ctccttcact tatgaagctt agtttggctg gatatgaaat   24600
tctgggttga aaattcttta agaaggtaga atattggccc ccactctctt ctggcttgta   24660
gagtttctgc caagagatcc actgttagtc tgatgggctt ccctttgtgg gtaacccgac   24720 cttctctct ggctgcccctt aacatttttt ccttcatttc aactttagtg aatctgacaa    24780
ttatgtgtct tggagttgct cttctcaagg agtatctttg tggcgttctc tgtatttcct   24840
gaatttgagt gttggcctgc cttgctaggt tggggaagtt ctcctggata acatcctgaa   24900
tagtgttttc caacttggtt ccattctccc catcactttc aggtacacca gtcagacgta   24960
gatttggtct tttcacatag tcccatattt cttggaggct ttgttcattt cttttgttc    25020 tttttctct aaacttctct tctcgcttca tttcattcat ttgatcttca atcactgata    25080 cccttcttg cacttgattg aatcggctac tgaagcttgt gcatgcatca cttagttctc    25140
gtgccatggt tttcagctcc atcaggtcat ttaaggtctt ctctaggctg tttattctag   25200
ttaaccattc gtctaatctt ttttcaaggt ttttagcttc ttcgtgatgg gttcgaacat   25260
cctcctttag ctcacagaag tttgttatta ccaatcgtct gaagccttct tctctcaact   25320
cgtcaaagtc attctccgtc cagctttgtt ccattgctgg tgaggatctg tgtttctttg   25380
gaggagaaga ggtgctctga tttttagaat cttcagcttt tctgttctgg tttctcccca   25440
tctttgtggt ttcatctacc tttggtcttt gatgatggtg atgtacagat ggggttttgg    25500
tgtggatgtc ctttctgttt gttagttttc cttctaacag tcaggaccct cagcttcagg   25560
tctgctggag tttgctggag gtccactcca gaccctgttt gcctgggtat caccagcgga   25620
```

```
ggctgcagaa cagcaaaatat tgcagaatgg caaatgttgc tgcctgatcc ttcctctgga   25680
agcttcgtct cagaggggat gggttgtcag tcggcccta  ctgggaggtg ccccccagt    25740 taggctactt gggggtcaag gaccctcttg aggaggcagt ctgtccgttc tcagatctca   25800
gactccgtgc tgggagaacc agtactctct tcaaagctgt cagacaggga cgtttaagtc   25860
tgcagaagtt tctgctgcat tttgttcagc tacgccctgc ccccagaggt ggagtctaca   25920
gaggcaggca ggcctccttg agttgcagtg ggctccacac agttcaagct tcctggcggc   25980
tttgtttacc tacccaagcc tcagcaatgg tggacgccct tcccctagcc tcactgctgc   26040
cttgcaattc gatttcaggc tgctgtgcta gcagtgagcg aggctctgtg ggcatgggac   26100
cctccgagcc aggcgcagga tataatctcc tggtgtgccg tttgctaaga ccattggaaa   26160
agtgcagtat taggatggga gtgtcctgat tttccaggta ctgtctgtca tggcttcctt   26220
tggctaagaa agggaattcc ctgaccccgt gcgcttcccg ggtgaggcga tgccccgtcc   26280
tgctttgtct catgctccgt gggctacacc cactgtctga caagccctag tgggatgaac   26340
ccgctacctc agttggaaat gcagaaatca cctgtcttct gcatggctca cactgggagc   26400
tgtagactgg agctgttctt ggaacctcct cctcatcatc ttgcttattt tcttataatt   26460
tgcttatctc acctacaaat aaattacaga gggaaaaatg caactaattg agcactccat   26520
ttttggtagc tagtagctga tggtatttta ataaactgag aagctaatga ggtgaatttt   26580
catgcatggc ttgtagtagc aggtgcagtt ctgtggtgta gaggcaatat gacatagtag   26640
gcagttgctt ggatttggtt tgactcctgg tcctgcttta tggatgctgc agattccttta  26700 ctttggaaaa gaggaatgaa gaatgcctag ccctaatgtg aaaattcaaa atactccaaa   26760
ctccaaaact ttttgagtgc ggatgtgatg cagcaagtca aaaattccac acctgacctc   26820
ctgtgatggg ttgtagttga aacttttaaa attatttaaa atatcgtata aaactacctt   26880
catgctatgt atgtaaggtg tatatggaac ataaatgaat tcatgtctac acttgggtc    26940 ccatccccaa gattatatat atgaaaatat ttcaaaatct gaaaaatttt gaaatccaaa   27000
agatttatgg tcacgaacat tttggataag gaatactcaa cctataccte acctgactca   27060 tggaattgtg ataatcaagt gagataatac ttattaaagc acttagtata atatgatata   27120
cagacatggt attggtatta tatgtgatag ttctctggcc caaacatgtc cttaatgtct   27180
ttttcagata ttcacacacc cttcccctct accacccctg ccccccttgg caattgtcca   27240
aataatgaaa acaagagctt tgtgagactt attcttttca aactttatgg cgtcatttat   27300
taaactaact tccttttcat tgcaagatgg aaaacatttt tacttctttt ggatgattat   27360
gccttgtggc ttgaaaggaa aattcattca acaaagcagc tactatgttt atatgtcagg   27420
cagtgatgac tgaggcaaag tcattgcact gtggctctta cagtctagag aaaataaaaa   27480
cattttataa aagccatgta taatgatata actgtttatg taagattgtg aaacaatgta   27540
agaagttgaa agagagagtt tgaccccttta agacaggaaa tcgttttggc caccgcctct   27600
tgttctaact gaagaaggaa tcaacaaaca ctgctcagca gtgagcgatg atgaagaaac   27660
tggcagatgg tttcctggga ctgggtatct ctgtactaaa agactgatga ggatttaaa    27720 agatgcttat tttgctgaat taagattaaa ccttaaaata ggaaaggaga ataaagtacg   27780
gtttgagact tctgtcaggt ttctctccta aaaacagatt gactagtgct gtgagaagca   27840
cttctaaaga aaatcaatat atgctcagca aggagcaagt aagttgtttt ttgtttgttt   27900 gttttttaact aatggacttt taaaagtaat tttaggttca cagcaaaatt gagtagaaag  27960
```

```
tacagagagt tcctacttac tgcttttctc cacacattga cagtcaggca ccagtgtggt    28020
agaataataa gcttttaata gaatgtttat ctttgtgttt ttcctgatct cttctatcaa    28080
aacattagcc tttttttttt ttgtacatga cttaaaatcc ttttttaaa tttggaatta    28140
gagtttataa gtgagtattt tgacatccat attttctgac aaaatgactt tcactttccc    28200
aagttcccag gctattttg ctttctccat cccacccta ccccttgtta gaatgttagt    28260
atgtatacag attggttttt tttaatatta acattaaatc agggacattc ttcagtgcca    28320
ctgaatttt ttttcaacat aattttgata gcatggtttt acttcatgga aaaatggaa    28380
gattgcaaat tgttaaattt tcagttaaat ataaccggcc cttgaaattc agctccttgc    28440
atttattag gaacttgatt tttatttcc tttttgcacc atcactatag taatgggatt    28500
aaagttaaaa ccagcaaatt taagcagata tttctattta agcagatatt tctatttaag    28560
cagctgtgat tagaaaagca gattgaattc actgaagaaa tgaagtatct ccagattta    28620
ttttactgtc tccttcccca tatatctgtt aatataatct ttttagattc gaggatttca    28680
acaagttact tcatgttttc tcaaagattt attttgggtc tataattact tgcctcgaga    28740
tcttccattt taagttaatt actataaaat attttttact gttactaaat acctcaactc    28800
tcagtgttaa cctttttttt ctaccttttt gttgggtttc aaatcattga tattttcaga    28860
tttcatagtc tataaggtat ggcttttaa agctgtgtag tcccatattt taacgtaaga    28920
tggcagcatt gagataaatg tgtagtgaca ccaagtgatt ttagttatttt ggtcaattag    28980
cccattgtaa caggggaaac ttgctgcttt aaagttctta gaaatgtacg ccaattctag    29040
gtgttttgc caactttttg aagtcacagt tccatggagt ttagccaggg gtatcaggaa    29100
tcttttcagt gctaggaatc tctgtagtgt tgaaagatac tggctaaata ttttttttt    29160
ttttttttt tttttttgga gacagagtct cgctctatcc cccaggctgg agtgcagtga    29220
catcgtctcg gctcactgca acctctacct cccaggttca agtgattctc atgcctcagc    29280
ctcccaagta gctgggatta caggcacctg ccaccatgcc cagctaattt ttatatttt    29340
agtagagaga cagggttttcg ccatgttggc caggctggtc ttgaactcct aacctcaggt    29400
ggtctgcctg cctttggcctc ccacagtgct gggattacag gattacaggg gtgagccaca    29460
gtgcccggcc acatactggc taaatattaa taagtaaaag tttatataac tagcctggct    29520
gtactctgaa ttcatattca aatgtccagc tgccttttga atagacactt tttgactatc    29580
actagattgt aggtctacta agtagttatt cattatttct gcacaattat tttacctttg    29640
tacattttt tttaaaacta ttcttgttga attgtatcca gttttgtaag aatcactctt    29700
aaatctgttg tcatatctat tcttgtcata gttggagagt atacctactc tgtgctgacc    29760
ccaacagtag aaccggaagg caaatcttgt ttcagttact attttaaaaa agaaacctc    29820
acacacacaa aaccccacaa ctttttaata actgttaaat aagtagaata ggctgttttg    29880
tgaagtagta agtgtcctat tttagaaata tgctagttga atctggataa ctgtgtcaga    29940
gattctatgg aagaaatgct tctaccacct aagaggttag gaaattattt catggctcca    30000
taactaaagg ctcagttcat ttcaattcag caagcagttt ttgagcacat acaatgtgtg    30060
gtcacaatgc taggcattgg gaatacataa acatggataa gaagttatac ccgctacatc    30120
caagggctc tcagtctagt aaggaagatg tcttaagaaa gtaatttagt caaaagcgaa    30180
aggatgcttg ggaaagtaag tcatctctgc agttcatggt agttggaaat ggcttctgtg    30240
tggatgtaag atgtaaggtg agccttaatc attgacactg tagtgtaatg gaatttgcat    30300
tggcatagga ttattaaaac tcaaatcctt gttcagcgtt tcctaaccaa aatttttgtca    30360
```

```
tctttaaaat tcaggtaata ctcatgtttc aaggtgttga gaaggttgag tggagttctg   30420
tgttcatgta tgtctgtgta ccacacaaat acatgtaaag acacatttat cttttactac   30480
tatgctttac acaattaagt attttattaa ttgttattaa taccatcatg acaatcattc   30540
caggcaaaat ttggctagag aagaataagg aagacatcaa ggaagaagag tattgagcaa   30600
aggcctatgt gggaatgaaa atgtaaaatg cccaagttaa tttgatggtt tgagttagac   30660
agtgttggga aataagctgt tagggtgtta tctatgccag agaaaaacag tatactttac   30720
ctgtcatcta gatgctgatt taaaaatttt cctggcctgg cgtggtggct cagacctgta   30780
atcccagcac tttgggaggc caaggcagga ggatcgcttg agcccaggag tttgagacca   30840
gcgtgggcaa caggggtaat ccctacctct acaaagaaaa aaaaaaatta gccaggcgtg   30900
gtggcatgtg cctgtagtcc cagctactca cgaggctgag gtgggaggat cacctgagcc   30960
agggagctcg agtctagggt gagccgtgat catgccactg tactccagct gggcaacag   31020 agcaagaccc tgtctctaaa taaataaata aataaattaa gattgttcct atttctgctt   31080
tagttatttg tgttaatttt aaataagttc catgtattct gaggtttaca cttaaacatc   31140
tctctcctta attagaacat agacaagtaa agtctattgt tatttttcaa gaatatttgg   31200
acaaatctat tgaaataaat atacagcgtt ttccaggtta tctttgataa cccactatgt   31260
tcaggttatt tggctggcaa cagagggtat atacaaagat gaatgcattg aaattgtctc   31320
caaactcaaa gtttagagaa cacttataat agcactaaaa cagataaaaa caaaattact   31380
gagagagaat taatttgaac tctttggggt ttggtaaagg ctttatgagg agtctttgaa   31440
gtaggctacc aaagactttt ctttcactaa tctcagcata tcagctctta gtaattgttt   31500
tgatgtgttt tttaataact cgattgaggt ataattcatg taaactgtac atatttaaag   31560
tgtacaattt ggtcagtttt tacatatata tatacgccca tgaaaccatc accataatca   31620
agataaaata tccatcacat ccaagtttct ttgtgaccct ttctaattca ctttctaccc   31680
ccattttcag gtaacactga tacactttct gtcactatac attaagttgt attttctagg   31740
attttatata atggaatcat agtgaatttt tttttgttgg gcttctttca ctcaacatag   31800
tgattgtaag attcatctgt gttgctgatg aatctaatag ttcattcctt tttaagacca   31860
agtagtattc tgttacatag atccaccacc atttgttcac cttttgatga acatttggtt   31920
attcacagtt ttaaggctat tgcaaataat gcttctgaat atttgtgatc tttgtatgtt   31980
atgatttgat tcttgggaa cctacctaat tagatggaat ggttgagtct taagtaggtg   32040
tatttttcac ttttttttttt ttgagacaga gtcttactct gttggccagg ctagagtgca   32100
gcggcacgat cttggctcac ttcagcctct gtctcgtggg ctcaagcagt tctcctggct   32160
cagcctccca agaagctggg attacaggca tgtgccacca cgcccagata attttgtat   32220 ttttagtaga gatggggttt catcatgttg gccagactgg tctcgaactc ctgacctcag   32280
ataatccacc cacctcagcc tcccaaagtg ctgggattac aggcatgagc caccgtgccc   32340
ggccgtcttt ttcactttt aagaaactgc caaacttttc ccaccaatgt atgagagttt   32400
cagttgttcc acatcctgcc aacgcttcat atggcaggtc ttttaatt taaccattct   32460 aatgggtgtg tagtagtact tgttgtggt tttagtttgc attttcataa tgattagtga   32520
tactgagcat cttttcatgt gcttatttac atctatatat ctagtttggt gaagtcttta   32580
ttttgtgtgc ttttaattg ggttatcttt attactgttt gtgtgtgtgt gtgtgtgtgt   32640
gtgtgtgtgt gtgtgtgttg tctaggtaca agtcctttgt cagatttatg ctctatagga   32700
```

```
atatattctc ttagtctatg gtttgccttt cttaaaaaat atatatatat taatggactg    32760
attttgcccc attattgagg catttcaccc tgagtattta tatgtaccct gtgtattttg    32820
aggttttccc actctggctt atgtgaaaac tattctgttt ttttgtgtta gctttgggaa    32880
ttttttttct ttttttagac ggggtctcac tctgttaccc aggccagaga acagtggtgc    32940
gatcatagct cactacagcc tcaacctccc aggctcaggc aatcctccca cctcagcttc    33000
ccaagtagct gcgactacat gcatatacca ccatgcctgg ctaatcctta aaaaattttt    33060
aatacatgga acttattttt atttatttat ttatttttat ttttttctca ctgtgttgcc    33120
caggctggtc tcctggtggg ctcaagcagt ccttcccctc tgcttctgga gtcactggga    33180
ttatagatag gagtaatctg taattagctc tgctaatttt tttttttttt ttacctattc    33240
cttttcaatg ttttttctcc gggatttgga tagttttctc atacgcatgt gctgttcagt    33300
gccagctgaa aatttgaggg agccctgct ggtctgcagc actctcttct caggtactcc    33360
tgctgtgaat tcagccagtg tggcctccct aaattctcac tcccatctca gctgctcagg    33420
gcgacttccc gagctgtttg ggcatcccct ccctgtgcca tagtctggaa actcggcagt    33480
aagctggggc agttgttgga gtcacctcct ttgccttcct tttcttataa ctattgttga    33540
gtgtctgaaa ctttgtatgt tttgttcagc tttctggtac tttaaggtag gacagtaaat    33600
ctggtcccta ttactccgtc ttgactggaa gtggaaactg tttcagtgta tttttgcttg    33660
aggaagaaaa atgtcatact tgagtcattt tagttcttga tttatgttaa gctgttggat    33720
tggtgcttct ccaaatactc actggaactg atgtttcaat tagatgtgga agacttaaca    33780
acaaattttt ttctggtaat tttcttccca aagcatctgg cagttcatgt tgcttatttg    33840
tatacttaca taaatatggg aattatatga gttgtgtaaa gctgtatttg atattcctgg    33900
atcatgttta aaaacatact ttgcataaca tcaattgagt gtgaaacgtg aattaagagc    33960
ttagaaagat ctagctgagt acatttgggg ggaaaacatg caattattag ttgttttttc    34020
tggttgagct ttttgaataa cttgaagtag ttgctttgta tcctttatct actttgaaca    34080
cacacatagt tatcaacccct cattaaaaga caggatttta gacttaaact ttgttttttgg   34140 ttgaagacat aataaaatct cctcaccaat ttctgtaagt aaaaggaggg gtgtaatttg    34200
gagaactgca gtaatcctct taaccatttt cacgctgtta ttcctaaaat aagaagggtt    34260
gaccagatct caaacctaaa acattatgat tctgtatatt tctatccaga catttatata    34320
gattactcat ttgctttcat atatttgtat taatagttta cattttcaag caaaatatgt    34380
atcttttcaa gtggttttgt cacttttggg aaaatgcaac attccaagtt taatgcattt    34440
ttatcaagga gagagcagag ttaaaggtgt aattcctttt ctttgggata cttctgccaa    34500
gagtctcaaa gaaagaatag tcattacaat gtaatggggg atgtaagtta atttgagaac    34560
tatgactagt tggatcagaa tgcagagcat ctgaattttt cttaatttgg tgttaaatat    34620
tcattctact tagacatttt aaatatagta ttaggacaaa attatcagac atttgtggaa    34680
tatatatgac tttgggggata taaaccaata tgggacagaa ttatagacac attattcctc    34740
aggatgtcac attgtaatat atagcacggg gattcttggg gtatagagtc tgaaatccca    34800
aaactatatt taagttttta tggaccacat gcctttcttt agtacgaagt tccatttctct   34860 tagattctca gatggtttca tgtcctttgt gaaagttaag aaccacagat gcagtgagga    34920
ttgagtgatt gctttggcag ccctcccttta aaaaacatttt acctcttcct gtatttttgg   34980
cttgtttgtt tgttttgaga caaggtctta ctctgacacc ctggagtgca gtggcgtaat    35040
catggcttat tgcatcctcg acttcctggg ctcaagtgat cctcatacct cagcctccca    35100
```

```
agtagctggg actacaggca tgcgccacag cgcctggcta attttgtggg gagttttcgt   35160
agacacaagg tctctccatg tttcccaggc tagtctcaaa ctcctgggct caagcagttc   35220
tcccatctga gcctcccaaa gtgctgggat tacaggcgtg agccaccatg cccagcttat   35280
tcttctgtta aaggaaaaac ttggtccttt ctgtcatggt atcctgaacc tcaccactct   35340
gtttattgaa tggtagtgac aaagccacat gagaccatag ataaaatata gcaatcttta   35400
tgctcttagc aatcttatga caaaatacat gcaagaggtt ttatataaga agagcataat   35460
tatgagtata aactgagaag gaattcgttt cacatttgtt gtgttttttg ccctcctata   35520
cctacatgcc tatgtttctc tctcttctc ctctctgtca gtctctctcc tctctctgtc   35580
tctgtctctg tctctctctc tgtcacacac acacacacac acacacacac acactttctt   35640
actccctcat tcagacatat acacatgctc atacccattt attgttgcca gtattttggg   35700
cttgttcata gaccagcttt ggtttgttgg agaaggttgg aagtgaaacc agaaaagttg   35760
tcataccatc tttgtgattt tggtgtattc aaagagaaac tggagatttg gttccttcaa   35820
atagtgattg ggcatatact aactggagtt cctaggagat ggtttaagaa ccagattgga   35880
ctcttttaag attaactcta aattgtgaca cagggcaaag agcagcatgt tcatagactt   35940
ggaaccaaat cacttcttca tagaaattag tgatttactt tatacagtcc tggcatatac   36000
ctttaatggc ttctggtaaa aattggatca taaataaata cttttgtgaa tttgtttttc   36060
ggtgtttaaa agttataaaa acaaacaaac cctactgtat gtgcacacac acaaactcca   36120
cagctgtctc agcttccacc agttgaaggt atccaagtct ccatttttgg tgtctgtata   36180
cttgcaatag aaacataatt tgttttcca tttgacacta tgctacttaa ctttgtcaaa   36240
gaaaatagaa atgtgagtaa tccttataaa tgggcaaaca cagctattta agaaggatta   36300
tatattagct cttttggaagc tcttttggtc atagataatt acctggaggc agttgttttt   36360
ttatataccc gagtttgata ttttgccagt tgagtttcaa acaatgaagt agaaatttgt   36420
ttatatattg cttagtcatt cttgttcata agaagagcat tctgaaattc ttaactatga   36480
atgggacctt gatttgaacc atatagttta aaatgcctga aaattattg gctaagtcct   36540
cttgaatttt atacctcatg attatgagtt agatgtttta cttattcctt ctttgggagt   36600
tgtttggaaa aaactcaaac cctgtttttc ctctgccttc acaccaacac aacaatagtc   36660
aacacaactt ctgcgttagt ccattcttgc attgctataa agaaatacct gaggctgggg   36720
aagagacact taattggctc acagttctgc aggttgtaaa agcatggctc cagcatctgc   36780
ttctgatgag ggcctcagga agcttacagt catggtggaa gagaaaggga gccagtgtac   36840
cacatggtga gagcaggagc gaaagcgaga gaaggaagag gtcccaggct tctttacaca   36900
accaaatctc atatgaacta actgagcaag aactgacttg tcaccaaggg gatgatgcta   36960
aaccatttga gagggatcct cccccatgtc ccagtctctt cccaccaggc cctacctcca   37020
atgttgggaa tcacgtttca acatgagatt gggaggggac aaacatccaa accatatcat   37080
tccaaccctg gcccctaaa tctcatatcc ccacatttca aaatacagtc atgccttcac   37140
aatagttccc caagtcttaa ctcattccag cattaactca aaagtcccaa gtctgaagtc   37200
tacaaagtct catctggaga tgagtttctt ccacctgtga tcctgtgaga tcagaaatga   37260
gttatttact cccaagatac agtggtagta cagacatttg gtatacctcc tattccaaaa   37320
gggagaaatc agccaaaaga aaggggcagt aggctctgtg caaatctgaa accagcaggg   37380
cagttgttaa atcttttttt cttttctttt ttctctctct ctctcttttt ttttttaaac   37440
```

```
agagtctcac tctcttggcc caggctgcat gatcacagct cactgcagcc ttgacctctc   37500
tggcacaagc catcctccca cctcaccctc ccaggtagct aggacctcag gagtgcacca   37560
ccatgcctgg ctaatttttg tattttagt agagaccgga ttccgccatg ttggccaggt    37620
tggtcttaac ctcctgagct caagtgatct gcccacctca gcctcccaaa gtgctaggat   37680
tacaggtgtg acccactctg ccaagccagt ctttaaatct taaagcttca aaacagtttc   37740
cttcttgcca tgtgaaacct gcttcccct tgccttccgt catgattgta agcctcctga    37800
ggccctcccc agaagcagat gctagagcca cgcttcctgt acagcctgca gaaccgtaag   37860
ccaaaataca cttgttttct ttataaatta cccagtctca ggtatttctt tatagcattg   37920
cagaaacgga ctaacacaaa attggtacca aggcatgggg cactgctata aagatacctg   37980
aagatgtgga agtagctttg gaactgggta aaaggcaaag gctggaagag tttggagggc   38040
aaagaagaca ggaagatgaa gaaaaatttg gaacttctga gagactggtt aaatggttgt   38100
gaacaaaatg ctgatagcga tatgaacagt gaagtctagg ctgatgaggt tccagatgga   38160
agtgaggatg ttattgggaa ctagagcaaa tgttacccct gtcacatcct agcaaagaac   38220
ctggctgtac tgtgtgccct agggataccc tcatcagttt ttcctcattc aagatgtggc   38280
ctggctgctt ctaacagcct atgatctaat atgggagcaa agaaatgact taagttaga   38340 acttatatac aaaagggaag cagagtgtaa aagtttggaa aattttcagt caagccatgt   38400
ggtagagaaa gaaaaagtat tttcaggaga agaatcctag caggctgtgg agcaaccacc   38460
tgaaaaagag gttatcatgg ccagggcaca gtagctcatg cctgttaatt ccagaacttt   38520
gggaggtcaa ggaaggagga tcacttgggc ccaggagttc aagaccactc tgggcaagaa   38580
agtgagacct catctctaca aaaaataaaa taattagctg ggtgtggtgg tgcatgcctg   38640
tagtcccagc tactcagggg cagaggcggg aggactgttt gagtctgagg ggtcaaggtt   38700
gcagtgagct atgatcacta aaatgagttt ggtcatttct aagacactgg attataagac   38760
atattaaaag aagatgtttt aagttagtat tatgtccagg taaggtttct taaaaataaa   38820
ttttttaaaa agaaaacaaa gttagttta tgagagaagg gggaggcccc agactcttaa    38880
acaaccagat ttcatgtgaa ctgagaagtc actcatcacc aagggatgg cactaagcca    38940 ttcaagaggg atccatcccc atgattcagt acctcccact aggtcccgcc ttcaacattg   39000
gggatcactt ttcagcatga gatttggagg agacaaacat ccaaactata tcaacttctg   39060
tgacccagtg ttgggggatg ggggttcccc accaataagc agcagacacc agctaggtat   39120
cctctaattt tgacactatc tgcctggatg tagcatcaga tcttacaagt tgaggactca   39180
atccccaaga ttgcccctg cccttttcag acaccagtca taagtctggg cctctggaac    39240
acctgactga ctggcttcaa gttggggttt tcacagcccc ctctttgggt tcacttaatt   39300
tccaggagtg gctcacagag ctcaggaaaa catgtttacc agtttagtat aaaatattac   39360
agaggataca aatgacacat aaaatgaggt atgggggaaa ggatgtggag cttccatgcc   39420
ctcccagggc cacaccgccc tccaggaacc tccacatttt cagctgtcca taagctctcc   39480
aaaccctgtc ctcttgggtt cttatggagg cctcattact tagacatgat taattaaact   39540
attggccatt ggtgatcaac ttgaccttca gcccctcttg ctcttccctg aggttgaggg   39600
atgggcttga aaatgctaac cctgtaatca tgcctttgcc tttttgctga ccagctccat   39660
cctgaagcta tcaatcaaca tgagcatgca aaaagacagc actttggaga tttcaaggat   39720
tttaggagtt ttgtaccagg aaacaggaac aaagaccaaa tatatattat atttcacaat   39780
atcattggaa ccttaagaaa gaagcctctc tcctttctta cggagcctag aggaataaag   39840
```

```
ataataataa agattacttt atttatgaat agtaatactt tacaaagtaa tctttattat   39900
ctttattcta gtttgccctt gaaccattaa aggttactaa gttgaattca ggctgagaaa   39960
aacaaaatag caaagaaaaa catttatgtt tgagatttta gtgatttata ttctgagatg   40020
ttatgtaatg gaaatacttt tgagataaag caaaaaatac ttaacattct tttagttgtt   40080
gcaacttatt taagagtgtg tgtaattctt acccttgaaa cctcaaccta gacatttagt   40140
gaattctgtt tttgaaatgg gaaaatcaag aataaagtca gattttaaaa attgtataaa   40200
acatgtagtt gctaaaatgt aattttaagt cctccttagg gtttcagttt tatgaaccct   40260
atgtcctcct taaggtttca ggaaacctcc ttagggtttc atgttgatag catattatat   40320
gaattattat ggcagttttt tctattttat aagttgtttt tctctgagat aaaatttctc   40380
taagtgggat ttttaatatt caagctttct tgactttttt tttaaaaaag acataaacca   40440
aaccaagtat attcttacct gtatctagta aagatttgtg tacatacatt taggagtgat   40500
ttatacatat gtcttgaagt gataaattgt tttaggtgat tatatgtttt atacatgttt   40560
gtgttatact tcaccagtag tgatattgtc aagcaaaaaa aaatatgcag catcataaaa   40620
ttaactttgt tttctttttta aaaaatttat tcttaagaaa ccttacctgg acataatact   40680
aacttaaaat atcttctttt aatatgtctt ataatccagt gtcttagaaa tgaccaaact   40740
cattttagtt atatctagga aatcaaaggt aaagatggag agattggcaa ggagaggagg   40800
ttcatgaatt gagagtagaa tgtgtaagaa gcatgaaata gatcacatcg agtctggata   40860
caacctcaga atccttctca atgcagtgtt ccaaatagct attaattact gattggagat   40920
ttggcccaga tactggtttt atgactaaaa gttgtcattt attgacatat tctctttctt   40980
ctaagcaaga gtaaaaattt agatgcatac acccttgtct tgttcatct gcttagaggc   41040
ttacatcatt agtgatcatg tcgtggggca aaattgggat tcagccccgg aggccacatg   41100
gttcttggct tcacggaggc aagaattcaa gagtgagcca aaagactaga gcgaaagcaa   41160
gtttattaaa aagtaaagga ataaaaggga ggctgccaca taggcagagt agccttgagg   41220
gctgctggtt ggctattttt tatggttatt aataaataat agcataaatt aatcgtatgc   41280
taaacaagga gtggattatt catgagtttt ctgggaaagg gtagggaatt gtcaggacca   41340
agagttcctt cccttttttag accttatagg gtaacttcca ggagttgccg tggcatctgt   41400
aaactgtcac ggcacagatg ggagtgtctt ttagcatgct agtgtattct agttagcaca   41460
taatgagcag tgaggatcat tgaggatgag cagaggtcac tgtctttgcc ctcttgattc   41520
tggctggttg tggctggctt ctttaccaca tcctgtttta tcagcagggt ccttgtgacc   41580
tgtgtcttga gaaacacgtt ctgccgaatt atctcaatca gcttttttata gaactgtgct   41640
tttcactgaa tatttttttc ttattgcacg ttcatttcag atgaaaaacc tgagaaatgt   41700
ggtcttcgcc tttgcgttgg aaaagaattg atgccttatt taagaaacaa tcagctaggt   41760
gtggtggttc acacctatga tcccagcact ttgggaggcc gaggtgagag catcacttgg   41820
ggccaggagt tcaagaccag cttgggcaac aagctaagac cccgtttcta caaaaaaaaa   41880
ctttaaaatg agttgggcat ggtggtgcac tcctgtggtc ctagttactt gggaggccta   41940
cgtgggaaga gtgcttgagc ccaggaggtc gaggctgcag tgagccatga tcacaccact   42000
gtattccagc ctgggtgaca gagcgagctc ctgtatcttt aaacaaaaac aaggaaaaaa   42060
atatcattta aaaaaatttt tgtgggattt tacatgtgct tttgccaaat tgcatgttgc   42120
tgaagagtgt tactaagcac tgacaacaga gtcttcctca gtcattatgt tgaaatacta   42180
```

```
tgtttcttcc cacaaataag aactgatttg attttaaatt attattattt ttttttccaag    42240
acagattctt gctctgtcac ccgggctaga gtgcagtgac gtgatcttgg ctcactgtga    42300
ccactgcccc ctgggtcaag tgattcttct gccttgggct tctgagtagc ttggactaca    42360
gtcatgtgcc accacaccca gctagttttt ttgtatattt gatagagatg ggattttact    42420
aggttggccc acctgttctc aaactcttgg cctcaagaga tctgcccatg gcctccctaa    42480
gtgctgggat tacttgattt taaatgattt taatcagcaa tggtttgaaa gtaaatttaa    42540
gtgactaaga agtgactaag ttcctaaatt atttactcta ctcctcataa acaagtattt    42600
tcttataaaa ggcattaagg ttttttccaag taaaatttt tggtataaat tgtttccata    42660
caatttaatt tatggtatac ctgtggtttt gcttttgcat ttggatcttt agcacttttg    42720
gatatctgat gaattttaac atatgctatt caatgaaatg agtttgttac ttgataccgt    42780
gtttaccttt agaataaagt gttaggtact aatatttag gagaactgac ttgaactcat    42840
ctcctggatt ctaaactcag cacaccacta atttgtgtgc tgggtcactt cactgctaga    42900
actgctgtgg cttttgctgc cactgtggct gtttgctatc acagattgat tgatggctct    42960
gtggcaaaca ctaccataga gccatcgatc aatatgtgat agcaaatatg tgagtatttt    43020
tctgtagctc aaatccaaca gctttgcaag ggaagtagc tatcttcatt tggcaggaat    43080
gaagcctgag agagattgag tcatttgccc taaaatttgc tcataaccaa gttatgccct    43140
gtagttttca agcttcttag ttttttccctc tctaaaaggg tatgacagaa cctgtatcat    43200
agagtaagca attactttgc taaggctaca cagagcagca tttctgtttt aagacttagt    43260
aggagtgtat tcatgaccca gctcaaacac cacctcctca gcaaagcgca ttcaattctt    43320
ccttagtcac aaggatttgt tctctgggtt tctctaacag acacatgcga atctgaaaga    43380
gccagaaatg tttcatttgt gttttttgttc ttttatccca ctattcttct cccctcccct    43440
cccctccaa gaagaaacta gcatggtgcc tggcacttgg catgaaatga cagagcctgt    43500
cacatctaac aaaattaacca aatgggtctt ttgaaaagtc tcttctttat tacgttttgg    43560
aaaactgagt gcagcttatt tgcccagggg cttttgtatg aatatgagca tcatcagcta    43620
gcggcttttt cttgagtagc aagctatgtt aagtcacaaa gggtaaaagt aaaaaaataa    43680
ttattatgaa tgaaattgtg ctcttttta atactttcca ttatcacaaa cttaaaatat    43740
ttatacttgg ttattgtaaa aatatataaa ttataaaaat aaaattataa gtgtattatt    43800
ccctataggc acatttcaat ttctaagcaa aatcttgttt ttgcttttaa tggctctact    43860
ttttttaaac tattacccctt gtcttattat tgttttacta gtgcatttaa ctagaccttt    43920
aagatattgg gggttttttgg tgtgtttcaa atttgtataa tagacattgc tctatgtaag    43980
aagataatca atacttacgg acttatataa aagttagcac ttttccttcc tattgaaaat    44040
tgtctggaat tctaaaatac aatttttaaaa caaattggat tcatcaaatg gtagaagaca    44100
gtaatttatt tttgatggga tggtttactg tgagaatcta atatataaac ttccttgatt    44160
tcccataaaa cttccagtaa gcattttaa gtataatttt cctcaaattt cttctgaaga    44220
attcactgat tttaacatat cactgacagt aaggcagtaa aaaaggggg gaaggtgttt    44280
actgcctttt gtataaaccc aaggaacctt gaaatttaca acttaaattt gagtcacagt    44340
ctagatttca tttcttctgt agcttgaatg caattaatag aactttgaac tcataatttg    44400
tgcatagctc ttttggtctc tttccttccc ccaatttata gttttcatgt gtgtgttttt    44460
atttgtcttg tatcttttct cctatttgct atttatttga ttaactttttg aatctaagta    44520
tgtaagactg tccataccac tgtctgtcct gtgctctcca acacagtagc caccagcaac    44580
```

```
atgtgattgt tggtgctta aaaagcagct ggtctgagcg aagctgtcca tactgtaaat    44640
tatgcactgg atctcagaca cttggtagaa aaaagaatgt aaagtttact aatggcgtat    44700
aaattacttg ctgaaatgac aatagtttgg atatatcgtc atatcttgtc cccagtttat    44760
tagagttctt ctgtggggga aagaggagag agttactgac agtaaattct tctggttaga    44820
cagtggaggt gttgctgctg ttgctgctat cctccctgac ctgttttgtg tgctaataga    44880
ttccatggag agcaataact gaaagttgaa tttaggattg cttctggctt tgaggtttct    44940
gcctaatggc taaaggattt aaaatgtaaa ccagtatatt tatattactt gttttctttt    45000
taacttgtat ccttattaaa tttcattatt tagatggtga cagtagtgtt agtttagact    45060
tgaatatact cagatgtata aaggggccag gcaagtaaca aaggaatgaa ttcatcctat    45120
gttagacaat gtggaatgat acatgtgctg tgtaacaagt atatgccctc tctacagggt    45180
gggtaacctt attcctgttt agctgattat ggtcttacgg gtatatatgg acttgtgttg    45240
ccagatcttt cagatttcta agaagagcaa aaatctggat ttttaagaat cttaaacctc    45300
tcaattttta aatactgata agtaatgtaa aatttaaaaa tacttatgct ggtcaaacta    45360
aatatggctg tgttctgaat gctaccgctt ggtaacttca gacctaagag attgcttctt    45420
ggaaataaat acaggtttta ggtatttttag atgacctaat taaagtatac cagttatgaa    45480
gagaggcttg gtaagcgcct gttgatgaat ggcttttaag ttttacacct tttagagaat    45540
attaatctga aagtagtgaa taattgtctt ttagtttgtt ttgaaatact gttaacagtt    45600
tcagtgtact ttttgagtat atatttctag cgtactctta tatatggaag ttattctgct    45660 ccttatttt tcttacatgc ttttctgtag ttattttgat atgaattgtt ttcctgaaca    45720
tttagaaaaa ggtttgtgtc agattgcttg tctcatctca cagagccccc ccgttctggt    45780
gtgtgtactg ttcagaagta tgatgggttg ttttctgaga tttcctggct ctgttccct    45840 ccccccactt tcatctagac ttacttttc ctttatctct tctgtccctc tcctgcttgg    45900
ctgaaattcc actcccagca gtttctctag tgtgagccct gtgtttggag agttcacagg    45960
agctccagga ttctctagcc ccgggcctca ctgtaggcct gccttgcact caccaagtcc    46020
tggagaggac taaatacttc ccaatttcag ctgctatatc cagttcacac acagcgcttc    46080
cagtgaatac ctgtgggctg tttgggattc tcttgttctc agattgctca gatgctctgt    46140
ggcttctctc tgctttcttc aacagatact gataatatct agtgcttgag gttggatgct    46200
acttggagtg gttcatagag aatactttc cacctagtta tgttgtaaat gtttcccatg    46260 ggttttttgga tttgctatct gcttgctgtg tttgtgtgtg ttggggggcag agggaatcag    46320 gaaggtctag aactgctgct tctatcctcc cagaaaatcc agatgcacta aattgataac    46380
ctgatgagtg gtggcaaaaa gtcagacagt catgttttgaa taggtttaca aattatattt    46440
aagaaaaata ttattttttc tataaaggta gggaaaaggc taagcagtca ttcactgctt    46500
cttaataaaa attctttacc agaaaaaaaa aatcatagaa aacttcaaga aaagaattg    46560 attcagctca gtgttgaaag tggtttgtat tcctggcact ttatactccc actcccaacc    46620
agagacacat tgtttcagcc acaataggtt acatcactaa ccttttttgg gttttgtaaa    46680
ccattaagga ttacatgaat taccatgtaa tcctgttcag acttggtaag acatttactg    46740
aatattgctt gttcttattc cctagatata aataaaataa taacacttta ttcaaaagag    46800
ctccatggag taatatttac taagggccag gttgctcagt tttatgcaca gaaaggcaat    46860
acagtgttga aatacacatc tgtttcaagt tcccatatct ataagacact tctctctctt    46920
```

```
taaacttaaa ggaaaatatg tatgcacact tatatggatt tacaacagta cagtgatctg    46980
aatttcggaa cttaactttc agtataaaaa gtttagttct ctgccacacg gaatttcagc    47040
cgtatgcttg tgtaatgtat ataaagattt aaaaaaatag atgggattat ttaaactaaa    47100
aaaagatgtg gaagttactc ctaagtgtaa atactatgtt ctatgacatt aatatatata    47160
ccttattttc tcttaatttc tatttgaagg tctcagccaa tttcttctcc agtcatcctc    47220
cagtttggtc atgcagagac tcttcttcca ctgctttctc tcatgggcta cttcaaagac    47280
aaggaacccc taacagcgta caattacaaa aaacaaatgc atcggaagtt ccgaagtggt    47340
ctcattgtac cttatgcctc gaacctgata tttgtgcttt accactgtga aaatgctaag    47400
actcctaaag aacaattccg agtgcagatg ttattaaatg aaaaggtgtt acctttggct    47460
tactcacaag aaactgtttc attttatgaa gatctgaaga accactacaa ggacatcctt    47520
cagagttgtc aaaccagtga agaatgtgaa ttagcaaggg ctaacagtac atctgatgaa    47580
ctatgagtaa ctgaagaaca ttttaattc tttaggaatc tgcaatgagt gattacatgc     47640
ttgtaatagg taggcaattc cttgattaca ggaagctttt atattacttg agtatttctg    47700
tcttttcaca gaaaaacatt gggtttctct ctgggtttgg acatgaaatg taagaaaaga    47760
tttttcactg gagcagctct cttaaggaga aacaaatcta tttagagaaa cagctggccc    47820
tgcaaatgtt tacagaaatg aaattcttcc tacttatata agaaatctca cactgagata    47880
gaattgtgat tcataataa cacttgaaaa gtgctggagt aacaaaatat ctcagttgga     47940
ccatccttaa cttgattgaa ctgtctagga actttacaga ttgttctgca gttctctctt    48000
cttttcctca ggtaggacag ctctagcatt ttcttaatca ggaatattgt ggtaagctgg    48060
gagtatcact ctggaagaaa gtaacatctc cagatgagaa tttgaaacaa gaaacagagt    48120
gttgtaaaag gacaccttca ctgaagcaag tcggaaagta caatgaaaat aaatattttt    48180
ggtatttatt tatgaaatat ttgaacattt tttcaataat tccttttac ttctaggaag     48240 tctcaaaaga ccatcttaaa ttattatatg tttggacaat tagcaacaag tcagatagtt    48300
agaatcgaag ttttttcaaat ccattgctta gctaacttt tcattctgtc acttggcttc    48360 gattttttata ttttcctatt atatgaaatg tatcttttgg ttgtttgatt tttctttctt   48420
tctttgtaaa tagttctgag ttctgtcaaa tgccgtgaaa gtatttgcta taataaagaa    48480
aattcttgtg actttactac caggactttt ctcttcccca tgtcaaaata caatcaataa    48540
ttgatggtaa aagtttggaa attcaagca                                      48569

<210> SEQ ID NO 7
<211> LENGTH: 23545
<212> TYPE: DNA
<213> ORGANISM: Homo sapiens

<400> SEQUENCE: 7
gattctgggc caagatggca gcaatgagga aggcgcttcc gcggcgactg gtgggcttgg       60
cgtccctccg ggctgtaagt gccccgagcc gccgaggcgg cggccctgca ggcactctga     120
ctgtcagggt tgggggcttg gcccgtggtg actgctctct tagaggcgag gccggacagc     180
tctcaggcca gagtcgggag ggcgttggag tcctggaccc tcccttttcc cctcaaatcc     240
tttgaagggg atgggaaaac tgaggtccgg agaggtggag tgacttgtct gggtcatgga    300
gacctgggac gccatcctag gtgccctgat tccccgccca gggcccttc cgatgaccct      360 ggccccttc tccctctaat tgaacttcag acctctccaa ctcttcatta gtgaaaatca     420
agaacacgct tccatttcct tcgtctccat ttccaactgt tgttgctttt agagatgctt    480
```

```
ggggaactat cccagcctac cgagcgggac ttgcgttgat tggagccaag ctgtgattcc    540
cttggaattg cactttgatc ctgttcgatc ctgatgtttt ccctctccc attctcagcg     600 cagaaaaagt gtgggagacg tagctgtatg gagcagaaaa aataaaagct gaagctaggg    660
tgtcccaata gttctgccac tttctagact taatgacata gttatttact ttctctaaac    720
ctcagctctt tcgtctgtaa aacggacaac attcccttgg ggttgttttg gaaattagag    780
aaaatgtaag taacacatct ggcagtgttc tggctcctaa taagtgatca gtcggtggtg    840 gtattttac cttagggagt tgagaaggag ttataactgt atagagggaa aaatacactc      900
ctggcactgg gtccctctca gaaagccacg ttaatatctt tacttggcca ttcacctgca    960
ccacctgctc atgtgtaaaa tgaagatggc aattccaact tggaaagtta aacgcaatag    1020
tagatattaa taagctttta agaaatattt ggtgtaatga gatggccctc catgggttc     1080 caagcatagg aaccagtatt agtattaggc ctagatatgg gttcaagtcc aagctctgtc    1140
actttctaat tgtgattttt gggtaacctt tctgaggctt agtttcttca cctacggagt    1200
tgggataata atagtccctg gcctgtagtt taacactggg tttagtcagt attcgctgtt    1260
ggtgttgatg caggtacacc atacctcagg acactgtggc acagtacttg tgtggttagg    1320
gggaccctct ctgagcagag ctttacagag gaggaacggg atgtttaacc aggagaagac    1380
tgtggaccga acgaacggtg gtaaagaggc aacagtggcc cagaggttag gagcttgtgc    1440
tctagagcca cactgccagg tttagatatt gcctcagtga gtaactcccc atgtcacctc    1500
gggaagatta cttaatctct ttgggtctca gatttctttt cttttctttc tttttttttt    1560
tcctgagacg gtgtcttgct ctgtcatctg tcacccagac tggagtgcag tggctcaatc    1620
tcagctcact gcaacctctg cctcccaggt tcaagcgatt cttctgcctc agcctcccaa    1680
gtggggcctt agatttctta cagtaaaatg gggatgatga tagttcctac ctgataagat    1740
tgttgagagg acagtatggg ttaatatgta aatggctcac caggcgtggt ggctcatgcc    1800
tataatccta gcactttggg aggctgaggt gggtggatca cttgaggtcg ggagttcggg    1860
accagcctgg ccaacctggt gaaatcctgt ctctactaaa atacaaaaaa ttagccaggt    1920
gtggtggtgc gcacctgtag tcccagctac tcgggaggct gaggcaggag aatcacttga    1980
acctgggagg tgaaggttgc agtgagccaa gatcgcgcca ctgctctcca gcctggagac    2040
agaatgagac tgtatctcaa ataaataaat aaataaataa atatgtaaat ggctcttgta    2100
tgtgcctggc aaatattaag tgtttaaaaa ctgaattatt atgtgaagag ctgttacggg    2160
gaaggaagga agtggaattg agtttataat gttctaataa aagcagcttg gaagcaggtt    2220
ttagaagctt tttttttttt tttttttttt gagatgaaga agtctcgctc ttgtacccca    2280
ggctggagta caatggcacg atctcagctc actgcaacct cctcctcctg ggttcaagca    2340
attctcctgc ctcagcctcc cgagtagctg ggattgcagg cacctgctgc catgcctagc    2400
taatttatgt gttttagta gagatagggc ttcaccatgt tggctaggct ggtctcgaac     2460
ttctgacctc aggtgatctg cccacctcgg cctcccaaag tgctgggatt acaggcgtga    2520
gccaccacgc ttggcctgaa gcaggtttta gattatttca gcaacactca actgttattt    2580
atcgagcccc tattatgtcc cagggcctta gaaatacagc attgaataaa acaaagtccc    2640
tgtctcatga aacttatgtt ccagtgagat agttttaggg tgatatacta gcagaggctg    2700
aacatccctg ttgagggag attcaagttg cagggacctt ccaacttagc ctgttgacgt     2760
catgaaattc aatggctcat cgccttagtc tctaagaaag cttgttggct aaaacaaggc    2820
```

| | |
|---|---|
| cagtcaggtg agttgtacat gttccagctg cttcctagca gggaattcct gggggacttc | 2880 |
| aggggttga gatccttagc ggatcacaca gtgtgccttc cgctttgcct cgttgtagta | 2940 |
| tatttatcca gattaaatct gtaaaacaaa gttgatttga aaagttacag tatcaagaca | 3000 |
| ggtagaggaa agaggaaaaa aaagtattg tgttacttga tagggaagac taagattttg | 3060 |
| agctgacttt atatagagga gactcagggc attttgtaaa aactgtcttc agctactggg | 3120 |
| ggtgtcacct cccttagac ccatgcttgt catcacccag cctatgactg taacagaaga | 3180 |
| gagccctcct gcatctcgcc catacccga aaagtccagg actgactact cctccccaca | 3240 |
| ctcagtaatt gctctcttct gggacagctg tgtccttcat ggtttatgtg ttatttaat | 3300 |
| aactttaaag agtggctact ttgtaccaaa cacggtgcca aacactaggg atgaagtgga | 3360 |
| gttgagacag acaaggtccc tcaaagagct tatgttctac tggaagagac attgagtagg | 3420 |
| cattctttat cgtgctttga aggaaataat tatagctctg caatagcgaa ataatgggg | 3480 |
| gtgggaggaa tggcagcttt gcaaagggtg gtcagaggaa gcctctctgc aactgaaaga | 3540 |
| tgagagagag atgtaagaac agccagtttt tttaaaaaaa gccagatgag gaaccctggg | 3600 |
| gcagagggaa gagaaggcag ggagcttagc aacctgttgg gtggaggttg ggagtggaca | 3660 |
| gtaggggcga gtgatgattc caggaggtca gaggaggcaa ctcatacagt cttttcttt | 3720 |
| cttaattgga aagcatcaag tgacatatag agtcatttaa ttttttttt tgagacaggg | 3780 |
| tctcgctctg ttgcccaggc tggagtgtag tggcacagtc atagctcact gcaggctcaa | 3840 |
| ccttctgggc tcaagcgatt ctcccacctc agcctcttga gtagctggga ctacatgtcc | 3900 |
| attccaccac acctggctaa tttttctatt tttagtagag acggggtttc ttcatcatgt | 3960 |
| tggccaggct gatctcgaac ctctggcctc aagtgatctg cctgccttgg cctcccaaag | 4020 |
| tgctgggatt acaggcatga gccaccgtgc ctggcctttt tttatttttt ttggaaatgg | 4080 |
| agtcttcctc tgtcgcccaa ggtggagtac agtggcacga tcttggctca ttgcaacttc | 4140 |
| cacctccctg gttcaagcaa ttctcctgcc tcagcctctt gagtagctgg agttacaggc | 4200 |
| gtgcaccacc acacccggct attttttgtg tattttagt agagatgggg tttcaccatg | 4260 |
| ttggtcaggc tggtctcaaa ctcccgacct caagtgatcg cccgcttcgg cctcccaaag | 4320 |
| tactgggatt acaggcatga gccactgccc cccgcaatac ctggcctttt taaactactt | 4380 |
| ctaacataca tacagcagca tacagagtcc tataggccat ggtgaatagg tgaaatggct | 4440 |
| caatgaagtt ctggcttatg cagtagggta catgcgatgc ctttgacaga gatggaaagg | 4500 |
| atggagtcag atgggcttta ggagaaatta gagttctgtt tcgggactgc tatatgaaga | 4560 |
| gatgcgaata gagctgtcag gtaggcagtg gaaaaggagt ctggacttca ggggagaacc | 4620 |
| ggtactggaa ggatgaatct cttgcttgtt cctgttacta agtgaaatat tctttttgtt | 4680 |
| cttaattcta aaatagacca aatgtgaatt aaatggtgag aaatatttct tcttgtctca | 4740 |
| ttattagtga agatagatcc attctttcat attggtctcc ctgggaattg tgcaatctc | 4800 |
| ttcctcatac ttttgtttc ctcttttaaa ccaaaggtca gcacctcatc tatgggcact | 4860 |
| ttaccaaagc gggtgaaaat tgtggaagtt ggtccccgag atggactaca aaatgaaaag | 4920 |
| gtaaagttgg aaatgagcca aaaaacagt ttttcaagc atctgctttg agtattacgt | 4980 |
| gtgataggtg caatggcagt tgacagagct atgcaagatg tgattcctct gcacaagtta | 5040 |
| ggggagagta gaggaggcca aacagggaca gacacctgtg acagttaaat gatctaaaat | 5100 |
| ggtgggcaa gctggatggg tggctcatgc ctgtcatccc taattacttg ggaggctgag | 5160 |
| gtgggaggat ggcttgagcc caggagtttg agaccagtct gggcaatata gcaagactct | 5220 |

```
atcttattaa aaaatatatg tatatatata aactgaatgg tggtgcaaca ggtttggtgt   5280
ccccaggtcc acagcccagt ggggtggggt agacccagca attccatgta aggggattta   5340
tccaaagcaa gtcacgaagg ccaaatgtag agatttagcc ttgggggtgt tccttacaaa   5400
cctgtttggt aagcacagaa cagttggaaa caacttaaat atttagtatg aggaaagttg   5460
ggtcagatac actatggact ttttataaaa tgaaatatta tgaagccatt aataacatag   5520
gtatatataa agtgactcaa gcagtttata aaatagtaca tgtgactggg catggtggtg   5580
gctcatgcct gtaatcccag cacttcagga ggctgaggca gagcacgatt ctgtctccaa   5640
acaaaaacaa atagtgcatg tgcgcgtacg cacgcgcgcg tgtgtgtgtg tgtgtttttg   5700
ggagatggca tctcactctg tcacccaggc tggagtgcaa tggcgcaatc tcggctcacc   5760
tcaacctcct cctcccgggt tcaagtgatt ctcctgcctc agcctcccga atagctagga   5820
ttacaggccc ctgccaccat gcccagctaa tttttgtatt tttagtagag atggggtttc   5880
accaggttgg ccgggctggt cttgaactcc cgacctcagg tgatccacct gcctcagcct   5940
cccaaagtgc tgggattaca ggcatgagcc aatgcgcctg gccatgtatt ttttaatctt   6000
aacactttta tgtaagaaaa aagtttatat atgtatggga gcatttatct agactaggac   6060
ctagaccagc actttctgtg aagatggaaa tattctggac ctgagctttt ccatgtggtg   6120
gccactatac ccatgtggcc cttgagaact tgagatgtga ctagtgtggc caaggaattg   6180
tattttatt tttatacaat ttttattaaa tttaaataac cacatgtgac tagtgacata   6240
ttgggctgca cagatctaga aagttacaca ccagggtgtt aatagcgtta tcactgggag   6300
attctaaggg tggttttctt ttgttttttgg catgtttttc tgaaagaatc atatattgat   6360
tattttttca ataagaaaag ctttttttctt tttctctttt tttttttttt tttttttttt   6420
tttagcacgt ccatcctagc tttaatagtg agtgcttgtt ggaaacaata gtgtgtaagt   6480
tcccgaaggg cagaatcctg tctgttctgc ttctgcttac tgctatatcc ccggcaccta   6540
gcacaatgcc tgcaacatgg agggctttca aaaattattt gacaggctgg gcatgatggc   6600
tcatgcctgt aatactggca ctttgggagg ctgaggcagg cagatcacct gaggtcagga   6660
gtttgagacc agcctggcca acatggtgaa acccatctc tactaaaata aatgagctgg   6720
ggtggtggca tgcttgtgta atcccatcta ctctggaggc tgaggcagga gaatcgcttg   6780
aacccggaag gcggaggtcg cagtgagctg agattgtgcc actgcactcc actctgggca   6840
atacagtgag actccatctc aaaaaaaaaa aaatttgtg gaaagattaa gttagagcag   6900
tgggagagaa actggagaag gcaggcaagg ggaggaccta gcgagaagga cctggagtat   6960
ttttgtgtgt tcttttttgtt tgagacaggg tcttgctctg tgtcactcag tgcagtggca   7020
caatcattgc tcactgcagc ctcgacttcc caggctccag tgatccacct cagcctcctg   7080
agtagctgga tcacagacac gtgccaccac gcctggctaa ttttttgtatt ttttgtagag   7140
agggggtttc gccatgttgc ccaggctggt ctcaaactcc taagcttaaa tgatctgcct   7200
gtctcagcct cccaaagtgc tgggattaca ggcgtgagcc aatgtgtccg cctggacctg   7260
gagttcttag aattttttgc gtaatcctgt aaatattagg gagccataga aagcttttga   7320
tgcaagaaa tggaaggttg gaagctgcat tttaggagga ttcctgtgta agatgaatta   7380
gtggcttgag actatgccat gttatataca ggataatgat ggtagatttg gaaagaggaa   7440
tccatggaat ctgttgagct actggacatg gtggggagga agataaagaa gctatacgct   7500
gaacacatga ggctgaagtc ctatgccaat tgggagacag aagcgaggag ggtgtgatac   7560
```

```
tttgggggcc ccatcccata ctccccagag ggttagtcat ctctgccctt tcaggccatc     7620
acacattgct ctcagtttgt ttatgatggg attataaatt aacacacatt tacttacggg     7680
aaagcctgca tggcagaata atgtttctat gtaaataact ccttttcagg tgagaagctg     7740
catccactgc aaaaaattat ctatagtact tgaactaaca ggtactgcat tttgaggctg     7800
ttttgttact aactttgctg ccttggtgtt tctctctcca ctatagaata tcgtatctac     7860
tccagtgaaa atcaagctga tagacatgct ttctgaagca ggactctctg ttatagaaac     7920
caccagcttt gtgtctccta agtgggttcc ccaggtgagc cctagccctc aatgaaaggc     7980
ctttctctag ggatgaaaag ttttgcattt gcctttgaag caagtagaag ttgagaacat     8040
aggtttccaa gcccctggct ttgagaggtc tcaggtgatt catagcactg tgttgcagca     8100
aaagaacatg acccaggatt cagggccttg ggttcagtct tggctctgct ctgacttgct     8160
cagtgacatt gctaaggcct tcccctcctc agtgttagag atgacctctt ctagccctaa     8220
agtctaaaac cctctatgcc tgtctgtggt ttctttgttt gtaaagagg aagactgaca      8280 actcctgctt cacaaagata gttaagtgaa gaagaaacat cctgttacaa aggagtgctt     8340
aacacagagc tgagctcagt gcctggccca gagtacattc tcaataaatg gctggtagta     8400
gtattcctgc tgtttctgca tatgtaaagc tggcagtatg ggccatatgg agaaattggg     8460
atctcagcca aaccaagggc ccttctgagc catcagcagt caaacaaaca gtaaaagtat     8520
tggagagact cagctctgca gaaggaatta ctcgctaaga gttctggaga acagaggttt     8580
tgtgatgaaa aggttttctc taactgaact ctctgtctgc tcttggtgat gacttggcaa     8640
tgtctccctt ggttcctaga tgggtgacca cactgaagtc ttgaagggca ttcagaagtt     8700
tcctggcatc aactacccag tcctgacccc aaatttgaaa ggcttcgagg cagcggtaag     8760
aggatagctt gttggtgggg gctcctgaaa tgagattgat ggcattggtc cctgccttgt     8820
cttggcgcct cagtcccctg tcctgggatg tccatctgaa tagcttgtct gtcagccaga     8880
ccctggggca aacctggccc tgccactcac tgctctgtga tcttgacaag ttgacaagcc     8940
tataaaatag ggctaaatga tagtacctga agttgtgagc atttcagaag ataggatgca     9000
tgtacattgc ttagcaagag ccagataaaa ggtaactgct taataaatgt tagctctttt     9060
gattatccac ttctttagag aaatgtaacc aaactctcca caagagtttc aacagtagtt     9120
gctggcatct gccaactttc ttacaatttt agacaagaac atctttggag gcgttggttc     9180
tgtatttagg caaaaacctt ttttggctg ggcacagtgg ctcacaccta taatcccagc      9240
actttgggag gctgaggccg gagaacagct tgaggccaga agcttgagac cagcctgagc     9300
aacataagga gaccttgtct ctacaaaaaa aaaaaaaaa atcaattagc tggctgtgat      9360
ggcatgcacc tgtagtccta gctactcggg agactgaggc acaggatggc ttgagactag     9420
gagttcgagg ctgcagtgag ccatgataat accgctgcac tcttccagcc tgggtgacac     9480
agcaagaaaa aaaaaaagc ttttctcaa gagtgacttc cagggtggtg atggcagtgg      9540
tggtggtttc cttggggaaa atcaaagttt ttttttttt aattaagaga aattactgtg      9600
tttgtttcct agtgctactg taagaaagca ctacaggccg ggcgcggtgg ctcacgcctg     9660
taatcccagc actttgggag accagggcgg gcggatcatg aggtcaggag atcgagacca     9720
tcctggctaa cacgatgaaa cccgtctct actaaaaata caaaaaatta gccaggcttg      9780
gtggcaggta cctgtaatcc tagctactca ggaggctgag gcaggagaat cacttgaacc     9840
cggaaggcgg aggttgcagt gagccaagat catgccactg cattccagcc tgggtgacag     9900
agcaagactt tgtctcaaaa aaagaaaaaa gaaaaaaaaa aagaaagcac tacaaattgg     9960
```

```
gtggcttaaa aacaacagaa atttattctc tcacagtctg gaggccagaa gtcccaaatc    10020
aaggtgtcag caggattggt tccttctgag gcctctggga gaatctgtcc tatgcctctc    10080
tgctggggtc tggtggtggc cagcagtcct tggcattgcc tggcttgtag atgcatctct    10140
ccagtctttg cctccgtttt cccagggcca ccttttctgt gtctctgtgt cttcacttgg    10200
ccatcttttg ttttttgtttt ttttagacag agtcttgctc tgtcgcccag gctggagtac    10260
agtggcatga tctcggctca ctgcaagctc cacctcccag gttcaagtga ttctcccacc    10320
tcagcctccc gagtagctgg gactacaggc gtgtgccacc acgaccggct aattttttgt    10380 attttttagta gagatggggt ttcactgtgt tagccaggat ggtctcgatc tcctgacctc    10440
atgatctgcc cgcctcggcc tcccaaagtg ctgtgattac aagcgtgagc cactgcgccc    10500
ggctggccat ctttttttaa ggtcaccagt cgtatgggat tagggccca ccctattcca    10560 gtatggcttc atcttaacta atgatatctg caatgacgct gtttccaaat aaggtcacat    10620
tctgaggtgc tgggttttaa tccttcaaca tatatttta ggaggacaca attcaaccca    10680
taacattcac ataacataaa atttaccttta agagaaattt tttgctactc tgtgtcagtg    10740
ttctttaaag agaaaagtgc tggccgggca tgatggctga cacctgtaat ctcagcactt    10800
tgggaggctg aggtgggtgg atcacaaggt caggagttcg aaaccagcct gaccaacatg    10860
gtgaaacgct gtctctacta aaaatacaaa aattagccgg gcgtggtggt gggctcctgt    10920
aatcccagct actcaggagg ctgaggcagg agaatcgctt gaacccagga ggtggaggtt    10980
gcagtgagcc gagatcatgc cactgcactc cagcctgggc aacaaagcaa gactccatct    11040
caaacaaaaa aagagaaaag tgctgaaagg agttcacctg gatgttggca ggttgctgct    11100
ggagccaagg aagtagtcat ctttggagct gcctcagagc tcttcaccaa gaagaacatc    11160
aattgttcca tagaggagag ttttcagagg tttgacgcaa tcctgaaggc agcgcagtca    11220
gccaatattt ctgtgcgggg gtgagtcaga gcacattggt atcctttcct ctgtaccgtt    11280
ctggaatggg gctagactct gactcaagtg gtcctcctgc cacaaacttc ttatcctggg    11340
tgggggcagc ctgagctcca cacctagaca tcttttccca aataagtgtg gtcagaagaa    11400
atcctaggaa gtactttctc tcaaacctga attttgggtc agtttaccag ctagccatga    11460
tagcatgcgc ctgtagtcct agcaacttgg gagactgagg cagaggatgg cttgagacca    11520
ggagtttgag gctgcagtga gccatgatag caccactgct atcatgctaa aggaatctag    11580
caggacagga cactaacggg tttgtggagg tcagttgagt cctggctttta tcactagctc    11640 ttcacacatc cctggagaat taacctaggct tctatgtttc caacatcaca tctctaatat    11700
cagtggttcc aggcattgtg tgtgtattat ctataataat tgaaacctca caatagccca    11760
gcagggagta ggttatcctc actttataaa ttacaaaacc gaggcccagg aagggcgaat    11820
actctactgt aaggtcacac tgctgtgcaa attgcagcca gaggccgggc atggtggctc    11880
acacctgtaa tccagcacct tgggaggac aaggcaggtg gatcacctga ggtcaagagt    11940
tcaagaccag cctggccgac atggtgaaac cccatctcta ctaaaaatac aaaaattagc    12000
tgggcgtggt agtggataga aaccccgtct ttactaaaaa tacaaaaatt agctgtaatt    12060
ccatctactt gggaggctga ggcaggagaa tcacttgaat ctgggaggcg gaggttgtgg    12120
tgagccgaga tcacaccact gtactccggc ctgggtgaca gagcaaaact ccatctcaaa    12180 aaaaaaaaa aaaaaaaaa aacattgcag ccagaatgat cgttgaaaag tgcacatctg    12240
ggctgaacat ggtggctcat gcctgtaatc ccagcacttt gggaggccga ggcgggcaga    12300
```

```
tcacctgagg taaggagttt gaaaccagcc tggccaacat ggggaaaccc catctctact    12360
aaaaatacaa aaattagccg ggcgtagtgg catgcacctg taatcccagc tactcaggag    12420
gctgaggcgg gagaatcact tgaacccagg aggcagaggt tgcagtgagc caagatcacg    12480
ccactgcact ccagcctagg tgacagagtg agactctgtc tcaaaaacaa aaaccaaaaa    12540
aaccccacaa aagtgcacat ctgatcacat ccctcctggt taaaaagctt tcagtgacta    12600
atcaagtgca gacttttta  tgaggtttac aaaccctgca tgatttggtc ccggctcttt    12660
tctgtagccg taccgttcaa gttcccttct ggcccctgct tcctcttcat ggtacactcc    12720
agcccaactg gaacttcttt ctgtttgtca catgcctcca ctcttgcctc tgggcctttg    12780
cacgtgctct ctctagactc agaacaacct tccttgggag gccaaggtgg gcaggttgct    12840
tcagcccagg agtttgtgac tggcttgggc ctgggcaaca tggtgaaacc ccagctctac    12900
aaaaaaaaag ccaggtgtgg ttgcatgtgc ctgtagtccc agctactcag gaggctaagg    12960
tgggaagatc acctgagcct gggaggtcca agctgaagtg agccaaaatc atgccactgc    13020
acaccagcat gggtgaaaga gtaagactct gtctccaaaa aataaagaac acttcctcca    13080
catcatgctt ctcggggata actcctgctc atccttcagg tcttcttgtg ggagtcagtt    13140
cctctgagaa gctgctccag tccttcagct ggagttagtg cccttctctg gaccccatg     13200
gtgtcgggac atcctctaaa tgtagcactt agctgcttgt taaattccct ccctgcccca    13260
ccccactaga ccgtgcactc catgagggca agcccacat  ctctcccagt ccctggggtg    13320
ctccactctc ccagcttggg gcctagccac agtgggcact cagtcactga cgggcaggtg    13380
gatgaatggg gaagcaggtg ctccagtaac attgggccca ctcccagatc tgtgtctttc    13440
taagcatctc tcttacctt  ttcttgctca gcagtggttg gagaataagt gggagcatca    13500
aaatggaaaa gtacactgag atctttgagt ctgaaattat ttatctgttg aacatttatt    13560
atgcctctta atatgcagaa tttgcttgac tctaaagggt tttaaagaca gctcccaaaa    13620
gggcaggtgg gaatagaagt cacctacatc ccaaatccac cctccttacc atagccctaa    13680
gacccatgat cagacctgtg cccaccttgc tgacctcctc atctcatact tccttttccc    13740
ttgctctgtc tgcctcagct gtcctttgtt ctgtctggag catgcctggc tcttctgtct    13800
cagggctttg cccaggtctt ccctctgcct ggaatgctct tctcacagac caccccggc    13860
tcctctcggc tccagcatcc tgtcctcaga gggatctttc ctggaccctc actagttggc    13920
ctcctccact tgttcctatc atttcccatc tttcctctgt ggcacatcac ttctgagatt    13980
ttctccatta cttacttggt tgctttttta ttggccatct ccctaacttg agataagctc    14040
tgagagggca ggaaccttat cagtcttgcc cactgctctg tgccagtgcc tggcacatag    14100
caggcaactc agtaaacatc aggtgaataa atgaatgaat gaatcctcta gcatctcact    14160
ggggcagctc atcccttggt cctcaggcca gcccagcctg ttactgactc atatccaact    14220
cagctcttgt tctgagtttg gttttaccca gtctttggtc tccttttgga gtactggccc    14280
cagctcctct ggcacgtagt tttgctccat ctccccacct tacaacccag ctgcttactc    14340
tccttgccct ctctagctcc tcctccgctt attgtaaatc cttggctgcc tctcctgagg    14400
cctgtgcaac ttctgcttcc tcaattgtag gtccattgtc ccccagttcc ctgccattgc    14460
tctctactgc ctcctcctgg cactgaattg taccatccct gcccttactc cgcccagctg    14520
caggtgttga ttgcacactg atcagaaatg tgtgttaaac agccctgcct cagttctgct    14580
agccaaaaag ctcaggacac tgacctcatt cctcccctgt cttcccacag gtacgtctcc    14640
tgtgctcttg gctgcccctta tgaagggaag atctccccag ctaaagtagc tgaggtgtgt    14700
```

```
gcatgtgtca gggcgggggg tttggtgagg gttggccacc ttgtctgccc ctgagcgcat   14760
aggttcctct ccccacccett tctggcaggt tcctgacttc attcattcac ccagctcctt   14820
cattaagctc ctgctgtgag cacagccctg cacttgctcc ctagaggccc ccctcctagc   14880
cgaacatgta gtccttgaag cccctggcct ctatccagcc tgaaaacctc caattcagtt   14940
tccagtctgg tcgttgaggt gattctctga ggaggggctc cttacccagg agttcccata   15000
gttccttgta gtgattgaaa ggccacaacc ctgatgtcct ctgaacagtc accaggtcaa   15060
cactgagaag aacatggcat gggaattgag tttgaccagc ccaagaactt atgtcattta   15120
gtcctcaaaa ccactgtgca aatttggtat tattattccc ttttacagtt gagaaaactg   15180
acactaaata acttgccaca caggttacaa atggtgaaat caggtatcaa accccatttt   15240
ttctctctcc aaagcccact tcttcccagg atactttgtg gcatccagat aggtggaatg   15300
gtaacagtag caactgtttc ttgagagcag ctgccctgct ccaggtctta gcctcagttg   15360
ccacaatcct tgccgtatga ccaaagggtc atcaccattt ttcagaagca gaaattgaag   15420
ctcagaaaag tgaagttgct tgccaaggcc cacagctagt gaacagcaga actaggactt   15480
taacccagca tctcgtgact tcaaaggcct gctccttccc ctgcaccctg ctgccccta    15540 aaggccagcc actgccgccc cacactctgc agggccactg gggaagcgac gtcaccattt   15600
catttattta gcagatcact ggtgtcttct ggtcccettt ccctgccaca tccctctgca   15660
ccttgtccag cagccccgtg tgggcagcag ctccttgggt gaggccatct tttttaagt    15720 tcaccagtcg tatgggatta ggggcccacc ctattccagt atggcttatt ccaattggac   15780
ccatattgga cctattccaa tatggaccca ttttgcagtg gttttagaga tgtgcaaatg   15840
ggcttccaaa aatttaaata gtgatgtacc tctattaaaa aatataacta ttggccgggc   15900
acggtggctc acgcctgtaa tcccagcact ttgggaggct gagatgggca gatcacaagg   15960
tcaggagatc gagaccatcc tggctaacat ggtgcaaccc cgtctctact aaaaatacaa   16020
aaaattagcc gggggtggtg gtgggcgccg gtagtcccag ctactcggga ggctgagaaa   16080
ggagaatggc gtgaacccgg gaggcggagc ttgcagtgag ctgagattgc gccaccgcac   16140
tccagcctgg gcaacagagg gagactccat ctaaaaaaaa aaaaaaaaaa atatatatat   16200
atatatatat atggactatt gattggccgg gtatggtggc tcatgactgt aatcccagca   16260
cttcgggagg ccgaagcatg tggatcacct gaggtcagga gttcaagacc agcctggcca   16320
acatggtgaa actccgtctc tactaaaaat acaaaaaata gtggggcgtg gtggtaggtg   16380
cctatgatcc cagctacttg ggagactgag acaggagaat cacttgaacc caggaggcag   16440
agcttgcagt gagccgagat tgtgccactg cactccagcc tgggcgacag agtgagactc   16500
tgtctcaaaa aatatatata tgtaaaatat atacattttt atacatatgg tccaagctac   16560
ttgggaggct gaggtgggag gattgcttga gtctgagagg ccaaggttgc agtaagccga   16620
gatcacacca ctgcactcta gccgaatgac agagtgagac ccgtctcaa aaaaaaaaa    16680 aaaaaagaa aaaaatata actagcatct cagacccatg atttcatgga ttttattgct    16740
gaggataaaa cgacatggaa ggaatcaact tcactgattc cagcacctgg gtctgacagt   16800
atgatgtgac agccgtaagt gagactgaag tctgaggggc acaggtaggg aggaaagcac   16860 ggggggttgga gcttcaggac tgtgggctgg ctccagcggc tggctctgcc ccttacgcct   16920
cagtctcctg atcatagatt gaggatcatc attcccagtt ggagtggtga ggagcatgta   16980
atccagtagg aactgagtgc gtcataccca gaagtgttct gcccaggcaa aggcccctc    17040
```

```
ttctgagtgc atggatcccc tggctggtgg attctgtatc ctccaagtgc ctgcttgctt   17100
ccttaggtca ccaagaagtt ctactcaatg ggctgctacg agatctccct gggggacacc   17160
attggtgtgg gcaccccagg gatcatgaaa gacatgctat ctgctgtcat gcaggaagtg   17220
cctctggctg ccctggctgt ccactgccat gacacctatg gtcaagccct ggccaacacc   17280
ttgatggccc tgcaggtaat caaaagcata tgcccattct cccaaaggtc acggtgggca   17340
ggacagcttg ttatcattta ttctttcagc aaacatttac tgatgccagt atgccaggtt   17400
ccaagctggc aatggtggac acagtcatgg tgaccctgcc cagatgtgaa gtgtacagct   17460
ctgtgttggg gagacagtca agggagttac atggcaatcc cactgcatta tgacagatgc   17520
catgaaggga ggaagcatgg ggctcaggaa gcctagaggg gccccatccc agctgaggag   17580
atctgggagg atttgcaaaa gaggcctcag tgaagcttga agaacataaa gtaagctgct   17640
gttgagggaa gaggaaagat gactaggcag aattgcacct caggactgat gtggggttca   17700
gggaggactc atacaatata cagggttttc agtgtgcggg tgtgtagcag aagcagatga   17760
ggaagcagga ggtagagaag ctagcagagg tcactcagag ggagaggctt taatgccgtt   17820
ccccacagat tgagctaaga cctcagatta gtttcctttg aggtttgctt ctcgtgggct   17880
ggtccagaat ggagatccat tggctggcag ccagatagaa ggagcattct tagtgtctga   17940
ccacagctac cttgctgtag cattggccta accttccatc tctaggatag tgatggcagt   18000
tccagccact tttttttttcc tctcaattat cccctagagg ttcgtgtcta agccaggtga   18060
gtctgttatg ttctgggtcg gtttcctcag agttgtggct gtcaaggtta aggttcgtag   18120
ttctgtggtc tcctcatttt tcagcttact gtgataccct gccctggttc ctgggctttc   18180
cttcagctca tgcgtttccc agccaggcag acaggaagag tgacttcctc tcctatgcct   18240
tgccaggcag gtaaagggga attctgcaca gctgaggtga gtctgaggca aaacttcatc   18300
ctgatcacgc tcaggacact cctgctcctc tgtgcttctc tgtttcatgg cagtgatatc   18360
tcagaatccc cttttgaaa atttatcagg gaacaggttg agctgtgtga cgtctggcag   18420
tagcttcctc tgacctccct cttccatcag ttacttcgga aatatggatc gatgtgccag   18480
gttaagtgct gacttagaca atggtaacaa gacccaatcc ctgccctctg ggagctcatg   18540
ttatggtggg tggggaagac agatggaaga ttacaggcgt gtaaatagca cattgtaaga   18600
ccatttattc acctattaaa acctaaccta acggtgccta gtgtgctagg cactgttctc   18660
agcattaagg attcagctgt gaccaaaaca gagtctctgc cctcatgagg ctgacactct   18720
agtactatga gacagataat aaataaacaa acatacagca ggccaggtgt tcataaacac   18780
tgtggagaaa aaatgaagca ggttaaggca gtgccaggcc tttctgtaga gtggcctcac   18840
tcagaaggta gcatttgaga gagacctgag ggaagcgagg gagtgagccc tgcggatccc   18900
tagcagggag gggagggaa gggagcccca cccaggaaag caggcgcaga gccctgaggg   18960
aggagtgtgc ttgctgtgtt cagggatcag gaggaggcat gtggcgggag cagtgtgact   19020
gaggagaggg gggcagagat gtcagggtta gaggaaggcc agatcggggg ccttgtagga   19080
ctttgactct ttcagactga gctgggaagc taacagagag tcttgagcag ggcgcgggag   19140
ggagatgatc tgaaatgttc cgtttgagag gctcctcggc tgggcacagt ggctcacacc   19200
tgtaatccca gcactttggg aggctgaggc aggtggatca cttgaggtca ggagttttga   19260
gaccagcctg gccaacatgg tgaaaccctg tctcaactaa aaatataaaa attagctggg   19320
cgtggtggcg tgagcctgta atcccagcta tttgcgaggc tgaggcatga gaatcacttg   19380
agcccgggag gtggaggttg cagtgatttg cagtgagctg agatggcgcc agtgcactcc   19440
```

```
agcctaggca acagagtgag acttcttatc aaaaaaaaaa aagaggctcc tctgggtgct    19500
gtgtagagaa tacactgtag agagaagaac cagtttggag cctacagcaa tccaggtgag    19560
agacatggca aggaggcctg gagggcagag gtgcgtgacc ggatctcagc agttcgtgtt    19620
ctgatctgtg aagctcgaga catctatagg caggtgtgtt aacctgggtg cagttaactg    19680
ggagtgagtg gagatagaga agctgtctga ggaatgagca gtaagggctc caaccgagat    19740
cagggaggtg aggaagagcc agcaaagact ggatcgaggc ctcaggagag gctagagcac    19800
taggaggaaa accaagggat gtggagccct ggaagccaca tggagaaggt gtccaagatg    19860
atgcggctag tcaagtgcaa agatgaagag acttgacctt tgtacttagc tacatggagg    19920
ccaccagtgg ccttgactag agctgtttca gtggaggagt tgtgggacg caaacctgtt    19980 tcgaatgggt tcaaatgaga atggtagatg ttaaatggga acagctcttt tgagggactt    20040
tgctttgaat gggggggaaag aaattggagg ttagagggtt ccaaaaaggt ttgtaaaaga    20100
tgggagagat cgcaggctgt gtgaagatga cccagtggag gggagtaaca ggttgcagca    20160
gagagggaga gacttactgg agcacatcct gaagcaggtg ggaatgggcc tcacgccaag    20220 gtggagggt tggccttggc taggagctca gggtccatct caggcagcat gagggacagt    20280
gggtctgtag gcccagatgt aggcaggtgg gtagatgtga tggtgggaat caatggagac    20340
atctcttgat tgcatccatt tccataaagc agcagatgag aatgaggatg gggaaggggg    20400
tgatagaggt ttaagaagag aggagaaagt gaaatagtca tttgggatag tgggaggtga    20460
ctgacctggg aagatgggat gtggccctcg tgtggcaagg ccctgactga gtgagagtag    20520
cctggaggtg gtgggggta agtgggggg gggtaataaa tgaatcacag taaacaacag    20580
gggtctgaaa tctcagcagt gggaggggt taggctggtg atcagaaaag gtctccctga    20640
gcaggtggct ttcagactgg aacctaaaga atgagagttc accatgaaag gaaagatact    20700
gctggcagag gaaacagttt aacagaaact aaaaggagaa gcactgtctc tttctgtggg    20760
attgtcatgt caacagaatc ataagccaaa gcaaagaatg actctagaat ttcaggcaac    20820
agacgattgg gaggtttgca aggctcatct ctgtggcctc ttgtcccag caacaactgt    20880 gtttcaccat ccttatgttt ctagatggga gtgagtgtcg tggactcttc tgtggcagga    20940
cttggaggct gtccctacgc acaggggca tcaggaaact tggccacaga agacctggtc    21000
tacatgctag agggcttggg cattcacacg gtaagcccac ccaccccctg gtggcgacag    21060
ccccgaactg accaggggc ctgaagctga gaacaaaagt ggatggggt atttggggtt    21120 gttaaggtgc tgaggagtaa agaggggaaag ggttagccag gcgcagtggc tcatgcctgt    21180
aatctcagca cttggggagg ctgaggcagg agggtcactt gagcccagga gtttgaggct    21240
gcagtgagct atgatcctgc cagtgtactc cagcctgggt gaaacagcaa gaccctatct    21300
cttcaaaaca aaacaaaaga ggggaagggt gttggggatt atggatattt gatctaatat    21360
tttaatgttt gtgagagtag ggttgagtga ggccacacgc atgggcataa gaaggctgga    21420
gtgtcagggt gactttgaca gttcagtcct aggagacacc aggaacatgg aagggccct    21480 gggaagggtc aggttcatga cctgaaatga gtcagttctc tcttggcttt gttttgttct    21540
ctgtaaaatg aggacagtag cgttagacag ctcaccaggg atccgccaga gtccaccagg    21600
gccctcagtg gcgggacgga agcagaatag catctgtgct taaagatcag atggaactgg    21660
gtttaaagcc tactcctgcc actcccaggc tatgagacct cagacaaatt atttcatctc    21720
tctgaaccta agaaatggga ataataatgc catccatctc atggagccat tgtgaggatt    21780
```

```
aagtaagaaa acgtacgtag agggccaggc gcacgcctgt aatcccagca ctttgggaag  21840
ccaaggcggg tggatcacct gaggtcaaga gtttgagacc agcctggcca atatggtgaa  21900
acactgtctc cactaacaat agaaaaattg ctgggcacgg tggctcacgc ccgtaatccc  21960
agcactttgg gaggccaggg tgggcagatc acctgaggtc aggagttcga gaccagcttg  22020
gccgacatgg tgaaacccca tctctactaa aaatacaaaa attagctggg tgtggtggca  22080
cgcacctgta atcccagcta ctcgggagac tgaggcagga gaattgcttg aacccaggag  22140
tcagaggttg cagtgagcca agatcacgcc actgtactcc agcctggcga cacagtgaga  22200
ctccctctca aaaaaagaa aagaaaaatt agctgggtgt ggtggcacac acctgtaacc  22260
ccagctactc gggaggctga ggcaggagaa tcacttgaac ccgggaggca gaggttgcag  22320
tgagctgaga gcgtgccatt gcactccagc ctgggcgaca agagcaaact ctgtctccaa  22380 aaaaaaaag aaagaaaagt tatgtagaat gcttatcaca gagctgagca cagagtgcac  22440
ttcagcaaat atgagctact gtatgaacag agggtttctg tctggccctt tcagttggtg  22500
tttttatccc tccctctctg cctcacaatt gtcacttgaa tatcagtttt ttacctctgt  22560
gggccaggcc ctgtgctggg ccctgaagag ggagtactga acaagactga taagatctgt  22620
gccctggtag tggcactaca aaccatgaca gagattgggc atcttacatg aggggagtc   22680 agaggaataa cccaggtgcc agacagacag gagctcacag gcagctggtg ccccgctgtc  22740
aaggaaaaag cctgttttatc ttcacccttta cttttcagta tcacagttgt ctgtccatgc  22800
tgatgttttc cctggtgttg agggcatacc atgacttacc gcatcctcta acttgtttct  22860
caaagggtgt gaatctccag aagcttctgg aagctgaaaa cttatctgt caagccctga   22920 acagaaaaac tagctccaaa gtggctcagg ctacctgtaa actctgagcc ccttgcccac  22980
ctgaagccct ggggatgatg tggaaatagg ggcacacaca gatgattcat ggatggggac  23040
atggaaatga gaataggtta aatggtgcag gtacctcata gccagctcta cacagaggtc  23100
tctcctggca gaaagcaggc gaagggcagg aggagctgct tggcagaagg acctcctgcc  23160
cagacctgag gagtgagagg cttttgagggc tgaagtctcc cttttgttacg gaccctggcc  23220 caggagttga atgcctgagg acgtgtggga accccgttcc ctacttagca tgatccttga  23280
gtctcctctc tggatggaat ccgcgagctg gccacctggc caccctctac acggctccac  23340
cctgccatgg ccgtggggcc cttgctctct gacttctcag gacacaggtc atggaggttc  23400
ttcccaagct ggcagaggcc atttgtggaa agtggagagc tacgtggtgg ccgtctgcca  23460
actccagcat ctctggaaaa tctccacgct gaatgtgatt tttgaaaaca gcttatgtaa  23520
ttaaaggttg aatggcacat cataa                                         23545
```